(12) United States Patent
Nakagawa et al.

(10) Patent No.: US 9,012,458 B2
(45) Date of Patent: Apr. 21, 2015

(54) ANTITUMOR AGENT USING COMPOUNDS HAVING KINASE INHIBITORY EFFECT IN COMBINATION

(75) Inventors: Takayuki Nakagawa, Tsukuba (JP); Tomohiro Matsushima, Tsukuba (JP); Yasuhiro Funahashi, Andover, MA (US)

(73) Assignee: Eisai R&D Management Co., Ltd., Tokyo (JP)

( * ) Notice: Subject to any disclaimer, the term of this patent is extended or adjusted under 35 U.S.C. 154(b) by 17 days.

(21) Appl. No.: 13/805,826

(22) PCT Filed: Jun. 23, 2011

(86) PCT No.: PCT/JP2011/064430
§ 371 (c)(1),
(2), (4) Date: Jan. 28, 2013

(87) PCT Pub. No.: WO2011/162343
PCT Pub. Date: Dec. 29, 2011

(65) Prior Publication Data
US 2013/0123274 A1    May 16, 2013

(30) Foreign Application Priority Data

Jun. 25, 2010 (JP) ................ P2010-145030
Dec. 8, 2010 (JP) ................ P2010-273921

(51) Int. Cl.
| | | |
|---|---|---|
| A61K 31/497 | (2006.01) | |
| A61K 31/496 | (2006.01) | |
| A61K 31/4427 | (2006.01) | |
| A61K 31/4545 | (2006.01) | |
| A61K 31/47 | (2006.01) | |

(52) U.S. Cl.
CPC ........ *A61K 31/496* (2013.01); *A61K 31/4427* (2013.01); *A61K 31/4545* (2013.01); *A61K 31/47* (2013.01)

(58) Field of Classification Search
USPC .................................. 514/253.12
See application file for complete search history.

(56) References Cited

U.S. PATENT DOCUMENTS

| | | |
|---|---|---|
| 4,526,988 A | 7/1985 | Hertel |
| 4,563,417 A | 1/1986 | Albarella et al. |
| 4,582,789 A | 4/1986 | Sheldon, III et al. |
| 4,742,003 A | 5/1988 | Derynck et al. |
| 4,764,454 A | 8/1988 | Ichijima et al. |
| 5,180,818 A | 1/1993 | Cech et al. |
| 5,445,934 A | 8/1995 | Fodor et al. |
| 5,464,826 A | 11/1995 | Grindey et al. |
| 5,487,889 A | 1/1996 | Eckert et al. |
| 5,624,937 A | 4/1997 | Reel et al. |
| 5,650,376 A | 7/1997 | Badaye et al. |
| 5,656,454 A | 8/1997 | Lee et al. |
| 5,658,374 A | 8/1997 | Glover |

(Continued)

FOREIGN PATENT DOCUMENTS

| | | |
|---|---|---|
| CN | 1473041 | 2/2004 |
| CN | 1478078 | 2/2004 |

(Continued)

OTHER PUBLICATIONS

Nakagawa et al. Cancer Science Jan. (2010) 101(1) 210-215.*

(Continued)

*Primary Examiner* — Shirley V Gembeh
(74) *Attorney, Agent, or Firm* — Fish & Richardson P.C.

(57) ABSTRACT

An antitumor agent for combined use of a compound or pharmaceutically acceptable salt thereof represented by Formula (I) and a compound or pharmaceutically acceptable salt thereof represented by Formula (II) exhibits an excellent antitumor effect compared to cases where these are individually used, and exhibits antitumor effects against various cancer types:

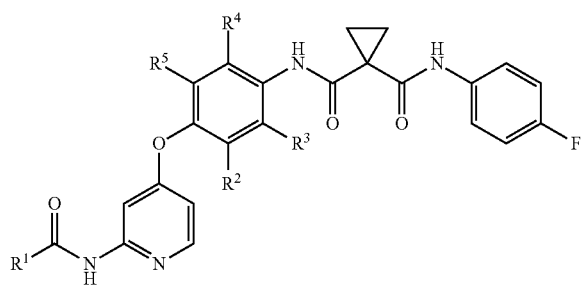

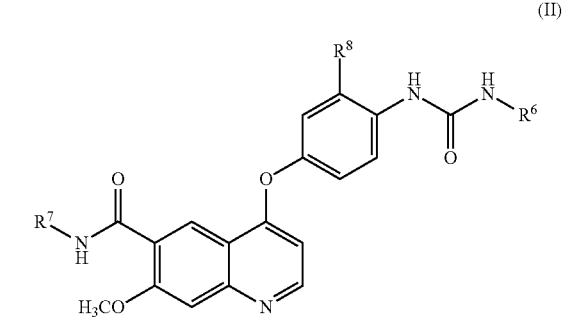

wherein $R^1$ is azetidinyl and the like, $R^2$ to $R^5$ is a hydrogen atom or a halogen atom, $R^6$ is $C_{3-8}$ cycloalkyl and the like, $R^7$ is a hydrogen atom and the like, and $R^8$ is a halogen atom and the like.

9 Claims, 5 Drawing Sheets

(56) References Cited

U.S. PATENT DOCUMENTS

| | | |
|---|---|---|
| 5,733,913 A | 3/1998 | Blankley et al. |
| 5,747,651 A | 5/1998 | Lemischka |
| 5,750,376 A | 5/1998 | Weiss et al. |
| 5,770,599 A | 6/1998 | Gibson |
| 5,792,783 A | 8/1998 | Tang et al. |
| 5,891,996 A | 4/1999 | Mateo de Acosta del Rio et al. |
| 5,948,438 A | 9/1999 | Staniforth et al. |
| 6,027,880 A | 2/2000 | Cronin et al. |
| 6,057,100 A | 5/2000 | Heyneker |
| 6,143,764 A | 11/2000 | Kubo et al. |
| 6,156,501 A | 12/2000 | McGall et al. |
| 6,156,522 A | 12/2000 | Keay et al. |
| 6,217,866 B1 | 4/2001 | Schlessinger et al. |
| 6,261,776 B1 | 7/2001 | Pirrung et al. |
| 6,346,398 B1 | 2/2002 | Pavco et al. |
| 6,476,040 B1 | 11/2002 | Norris et al. |
| 6,524,583 B2 | 2/2003 | Thorpe et al. |
| 6,534,535 B1 | 3/2003 | Zhu et al. |
| 6,576,424 B2 | 6/2003 | Fodor et al. |
| 6,676,941 B2 | 1/2004 | Thorpe et al. |
| 6,762,180 B1 | 7/2004 | Roth et al. |
| 6,797,823 B1 | 9/2004 | Kubo et al. |
| 6,811,779 B2 | 11/2004 | Rockwell et al. |
| 6,812,341 B1 | 11/2004 | Conrad |
| 6,821,987 B2 | 11/2004 | Kubo et al. |
| 7,005,430 B2 | 2/2006 | Ueno et al. |
| 7,101,663 B2 | 9/2006 | Godfrey et al. |
| 7,135,466 B2 | 11/2006 | Sakai et al. |
| 7,169,789 B2 | 1/2007 | Kubo et al. |
| 7,211,587 B2 | 5/2007 | Kubo et al |
| 7,253,286 B2 | 8/2007 | Funahashi et al. |
| 7,435,590 B2 | 10/2008 | Komurasaki |
| 7,485,658 B2 | 2/2009 | Bolger et al. |
| 7,495,104 B2 | 2/2009 | Miwa et al. |
| 7,547,703 B2 | 6/2009 | Roth et al. |
| 7,550,483 B2 | 6/2009 | Sakaguchi et al. |
| 7,612,092 B2 | 11/2009 | Funahashi et al. |
| 7,612,208 B2 | 11/2009 | Matsushima et al. |
| 7,725,303 B2 | 5/2010 | Tramontana |
| 7,790,885 B2 | 9/2010 | Nagai et al. |
| 7,855,290 B2 | 12/2010 | Matsushima et al. |
| 7,973,160 B2 | 7/2011 | Funahashi et al. |
| 7,994,159 B2 | 8/2011 | Yamamoto et al. |
| 8,288,538 B2 | 10/2012 | Matsushima et al. |
| 8,372,981 B2 | 2/2013 | Funahashi et al. |
| 8,377,938 B2 | 2/2013 | Matsushima et al. |
| 8,580,254 B2 * | 11/2013 | Adam et al. ............... 424/130.1 |
| 2002/0010203 A1 | 1/2002 | Lipson et al. |
| 2002/0040127 A1 | 4/2002 | Jiang et al. |
| 2003/0013208 A1 | 1/2003 | Jendoubi |
| 2003/0087907 A1 | 5/2003 | Kubo et al. |
| 2003/0113713 A1 | 6/2003 | Glezer et al. |
| 2003/0215523 A1 | 11/2003 | Ozawa et al. |
| 2004/0009965 A1 | 1/2004 | Collins et al. |
| 2004/0034026 A1 | 2/2004 | Wood et al. |
| 2004/0034832 A1 | 2/2004 | Taylor et al. |
| 2004/0053908 A1 | 3/2004 | Funahashi et al. |
| 2004/0086915 A1 | 5/2004 | Lin et al. |
| 2004/0132727 A1 | 7/2004 | Sakai et al. |
| 2004/0152759 A1 | 8/2004 | Abrams et al. |
| 2004/0167134 A1 | 8/2004 | Bruns et al. |
| 2004/0171068 A1 | 9/2004 | Wehland et al. |
| 2004/0191254 A1 | 9/2004 | Fagin |
| 2004/0229876 A1 | 11/2004 | Kubo et al. |
| 2004/0242506 A1 | 12/2004 | Barges Causeret et al. |
| 2004/0253205 A1 | 12/2004 | Yamamoto et al. |
| 2004/0259834 A1 | 12/2004 | Kasprzyk et al. |
| 2005/0014727 A1 | 1/2005 | Muller et al. |
| 2005/0049264 A1 | 3/2005 | Miwa et al. |
| 2005/0119303 A1 | 6/2005 | Wakabayashi et al. |
| 2005/0176802 A1 | 8/2005 | Tang et al. |
| 2005/0187236 A1 | 8/2005 | Tsuruoka et al. |
| 2005/0209452 A1 | 9/2005 | Bornsen et al. |
| 2005/0272688 A1 | 12/2005 | Higgins et al. |
| 2005/0277652 A1 | 12/2005 | Matsushima et al. |
| 2006/0004017 A1 | 1/2006 | Stokes et al. |
| 2006/0004029 A1 | 1/2006 | Tsuruoka et al. |
| 2006/0057195 A1 | 3/2006 | Nonomura et al. |
| 2006/0079494 A1 | 4/2006 | Santi et al. |
| 2006/0135486 A1 | 6/2006 | Owa et al. |
| 2006/0160832 A1 | 7/2006 | Funahashi et al. |
| 2006/0178399 A1 | 8/2006 | Nishizawa et al. |
| 2006/0189629 A1 | 8/2006 | Bolger et al. |
| 2006/0252777 A1 | 11/2006 | Kim et al. |
| 2006/0292192 A1 | 12/2006 | Hasenzahl et al. |
| 2007/0004773 A1 | 1/2007 | Sakaguchi et al. |
| 2007/0027318 A1 | 2/2007 | Kubo et al. |
| 2007/0032521 A1 | 2/2007 | Moussy et al. |
| 2007/0037849 A1 | 2/2007 | Naito et al. |
| 2007/0078159 A1 | 4/2007 | Matsushima |
| 2007/0117842 A1 | 5/2007 | Arimoto et al. |
| 2007/0214604 A1 | 9/2007 | Yi |
| 2008/0207617 A1 | 8/2008 | Miwa et al. |
| 2008/0214604 A1 | 9/2008 | Furitsu et al. |
| 2008/0241835 A1 | 10/2008 | Mehraban et al. |
| 2008/0286282 A1 | 11/2008 | Semba et al. |
| 2009/0047278 A1 | 2/2009 | Owa et al. |
| 2009/0047365 A1 | 2/2009 | Owa et al. |
| 2009/0053236 A1 * | 2/2009 | Yamamoto ............. 424/158.1 |
| 2009/0202541 A1 | 8/2009 | Bruns et al. |
| 2009/0209580 A1 | 8/2009 | Matsui |
| 2009/0247576 A1 | 10/2009 | Kamata et al. |
| 2009/0264464 A1 | 10/2009 | Yamamoto et al. |
| 2009/0304694 A1 | 12/2009 | Oliner et al. |
| 2010/0048503 A1 | 2/2010 | Yamamoto |
| 2010/0048620 A1 | 2/2010 | Yamamoto |
| 2010/0092490 A1 | 4/2010 | Uenaka et al. |
| 2010/0105031 A1 | 4/2010 | Matsui et al. |
| 2010/0239688 A1 | 9/2010 | Yamamoto |
| 2010/0324087 A1 | 12/2010 | Yamamoto |
| 2011/0020410 A1 | 1/2011 | Nonomura et al. |
| 2011/0118470 A1 | 5/2011 | Funahashi et al. |
| 2011/0158983 A1 | 6/2011 | Bascomb et al. |
| 2011/0207756 A1 | 8/2011 | Matsui |
| 2011/0293615 A1 | 12/2011 | Yamamoto |
| 2012/0077842 A1 | 3/2012 | Bando |
| 2012/0207753 A1 | 8/2012 | Yu et al. |
| 2012/0219522 A1 | 8/2012 | Xi |
| 2012/0244209 A1 | 9/2012 | Roth et al. |
| 2012/0263677 A1 | 10/2012 | Eagle et al. |
| 2012/0283206 A1 | 11/2012 | Bruns et al. |
| 2013/0296365 A1 | 11/2013 | Bando |

FOREIGN PATENT DOCUMENTS

| | | |
|---|---|---|
| CN | 1890220 | 1/2007 |
| CN | 101001629 | 7/2007 |
| CN | 101029022 | 9/2007 |
| CN | 101198590 | 6/2008 |
| CN | 101316590 | 12/2008 |
| CN | 101454286 | 6/2009 |
| CN | 101454311 | 6/2009 |
| CN | 101616671 | 12/2009 |
| CN | 102470133 | 5/2012 |
| EP | 0 203 126 | 12/1986 |
| EP | 0 297 580 | 1/1989 |
| EP | 0 405 425 | 1/1991 |
| EP | 0 602 851 | 6/1994 |
| EP | 0 684 820 | 12/1995 |
| EP | 0 712 863 | 5/1996 |
| EP | 0 795 556 | 9/1997 |
| EP | 0 837 063 | 4/1998 |
| EP | 0 870 842 | 10/1998 |
| EP | 0 930 305 | 7/1999 |
| EP | 0 930 310 | 7/1999 |
| EP | 1 029 853 | 8/2000 |
| EP | 1 044 969 | 10/2000 |
| EP | 0 543 942 | 1/2001 |
| EP | 1 153 920 | 11/2001 |
| EP | 1382604 | 1/2004 |
| EP | 1 411 046 | 4/2004 |
| EP | 1 415 987 | 5/2004 |
| EP | 1 447 045 | 8/2004 |
| EP | 1 447 405 | 8/2004 |

(56) References Cited

FOREIGN PATENT DOCUMENTS

| | | |
|---|---|---|
| EP | 1 473 043 | 11/2004 |
| EP | 1 506 962 | 2/2005 |
| EP | 1 522 540 | 4/2005 |
| EP | 1 535 910 | 6/2005 |
| EP | 1 552 833 | 7/2005 |
| EP | 1 566 379 | 8/2005 |
| EP | 1 604 665 | 12/2005 |
| EP | 1 331 005 | 4/2006 |
| EP | 1 683 785 | 7/2006 |
| EP | 1 698 623 | 9/2006 |
| EP | 1 719 763 | 11/2006 |
| EP | 1 777 218 | 4/2007 |
| EP | 1 797 877 | 6/2007 |
| EP | 1 797 881 | 6/2007 |
| EP | 1 859 793 | 11/2007 |
| EP | 1 859 797 | 11/2007 |
| EP | 1 889 836 | 2/2008 |
| EP | 1 894 918 | 3/2008 |
| EP | 1 925 676 | 5/2008 |
| EP | 1 925 941 | 5/2008 |
| EP | 1 949 902 | 7/2008 |
| EP | 1 964 837 | 9/2008 |
| EP | 2 058 302 | 5/2009 |
| EP | 2 116 246 | 11/2009 |
| EP | 2 119 707 | 11/2009 |
| EP | 2 133 094 | 12/2009 |
| EP | 2 133 095 | 12/2009 |
| EP | 2 218 712 | 8/2010 |
| GB | 2253848 | 9/1992 |
| IL | 148756 | 10/2007 |
| IN | 236500 | 11/2009 |
| JP | 63-028427 | 6/1988 |
| JP | 1-022874 | 1/1989 |
| JP | 2-291295 | 12/1990 |
| JP | 4-341454 | 11/1992 |
| JP | 6-153952 | 6/1994 |
| JP | 7-176103 | 7/1995 |
| JP | 8-045927 | 2/1996 |
| JP | 8-048078 | 2/1996 |
| JP | 9-023885 | 1/1997 |
| JP | 9-234074 | 9/1997 |
| JP | 3088018 | 6/1998 |
| JP | 11-501343 | 2/1999 |
| JP | 11-143429 | 5/1999 |
| JP | 11-158149 | 6/1999 |
| JP | 11-322596 | 11/1999 |
| JP | 3040486 | 5/2000 |
| JP | 3420549 | 10/2000 |
| JP | 2000-325080 | 11/2000 |
| JP | 2000-328080 | 11/2000 |
| JP | 2001-131071 | 5/2001 |
| JP | 2002-003365 | 1/2002 |
| JP | 2002-114710 | 4/2002 |
| JP | 2002-536414 | 10/2002 |
| JP | 2003-012668 | 1/2003 |
| JP | 2003-026576 | 1/2003 |
| JP | 2003-525595 | 9/2003 |
| JP | 2004-513964 | 5/2004 |
| JP | 2004-155773 | 6/2004 |
| JP | 2004-531549 | 10/2004 |
| JP | 2005-501074 | 1/2005 |
| JP | 2005-504111 | 2/2005 |
| JP | 2005-520834 | 7/2005 |
| JP | 2005-272474 | 10/2005 |
| JP | 3712393 | 11/2005 |
| JP | 2006-508981 | 3/2006 |
| JP | 2006-515884 | 6/2006 |
| JP | 2007-153894 | 6/2007 |
| KR | 2003-40552 | 5/2003 |
| KR | 10-0589032 | 11/2005 |
| WO | WO 86/03222 | 6/1986 |
| WO | WO 92/20642 | 11/1992 |
| WO | WO 94/09010 | 4/1994 |
| WO | WO 95/15758 | 6/1995 |
| WO | WO 95/17181 | 6/1995 |
| WO | WO 95/19774 | 7/1995 |
| WO | WO 96/09294 | 3/1996 |
| WO | WO 96/26997 | 9/1996 |
| WO | WO 96/30347 | 10/1996 |
| WO | WO 96/33980 | 10/1996 |
| WO | WO 96/39145 | 12/1996 |
| WO | WO 96/40142 | 12/1996 |
| WO | WO 97/03069 | 1/1997 |
| WO | WO 97/13760 | 4/1997 |
| WO | WO 97/13771 | 4/1997 |
| WO | WO 97/17329 | 5/1997 |
| WO | WO 97/21437 | 6/1997 |
| WO | WO 97/38984 | 10/1997 |
| WO | WO 97/48693 | 12/1997 |
| WO | WO 98/00134 | 1/1998 |
| WO | WO 98/02434 | 1/1998 |
| WO | WO 98/02437 | 1/1998 |
| WO | WO 98/02438 | 1/1998 |
| WO | WO 98/13350 | 4/1998 |
| WO | WO 98/14437 | 4/1998 |
| WO | WO 98/23613 | 6/1998 |
| WO | WO 98/32436 | 7/1998 |
| WO | WO 98/35958 | 8/1998 |
| WO | WO 98/37079 | 8/1998 |
| WO | WO 98/50346 | 11/1998 |
| WO | WO 98/52558 | 11/1998 |
| WO | WO 99/00357 | 1/1999 |
| WO | WO 99/32106 | 7/1999 |
| WO | WO 99/32110 | 7/1999 |
| WO | WO 99/32111 | 7/1999 |
| WO | WO 99/32436 | 7/1999 |
| WO | WO 99/35132 | 7/1999 |
| WO | WO 99/35146 | 7/1999 |
| WO | WO 99/43654 | 9/1999 |
| WO | WO 99/62890 | 12/1999 |
| WO | WO 00/31048 | 6/2000 |
| WO | WO 00/42012 | 7/2000 |
| WO | WO 00/43366 | 7/2000 |
| WO | WO 00/43384 | 7/2000 |
| WO | WO 00/44728 | 8/2000 |
| WO | WO 00/47212 | 8/2000 |
| WO | WO 00/50405 | 8/2000 |
| WO | WO 00/71097 | 11/2000 |
| WO | WO 01/02369 | 1/2001 |
| WO | WO 01/23375 | 4/2001 |
| WO | WO 01/27081 | 4/2001 |
| WO | WO 01/32926 | 5/2001 |
| WO | WO 01/36403 | 5/2001 |
| WO | WO 01/40217 | 6/2001 |
| WO | WO 01/45689 | 6/2001 |
| WO | WO 01/47890 | 7/2001 |
| WO | WO 01/47931 | 7/2001 |
| WO | WO 01/60814 | 8/2001 |
| WO | WO 02/16348 | 2/2002 |
| WO | WO 02/32872 | 4/2002 |
| WO | WO 02/36117 | 5/2002 |
| WO | WO 02/41882 | 5/2002 |
| WO | WO 02/44156 | 6/2002 |
| WO | WO 02/072578 | 9/2002 |
| WO | WO 02/080975 | 10/2002 |
| WO | WO 02/088110 | 11/2002 |
| WO | WO 02/092091 | 11/2002 |
| WO | WO 02/096361 | 12/2002 |
| WO | WO 03/000660 | 1/2003 |
| WO | WO 03/006462 | 1/2003 |
| WO | WO 03/013529 | 2/2003 |
| WO | WO 03/024386 | 3/2003 |
| WO | WO 03/027102 | 3/2003 |
| WO | WO 03/028711 | 4/2003 |
| WO | WO 03/033472 | 4/2003 |
| WO | WO 03/050090 | 6/2003 |
| WO | WO 03/074045 | 9/2003 |
| WO | WO 03/079020 | 9/2003 |
| WO | WO 03/087026 | 10/2003 |
| WO | WO 03/099771 | 12/2003 |
| WO | WO 2004/006862 | 1/2004 |
| WO | WO 2004/020434 | 3/2004 |
| WO | WO 2004/032872 | 4/2004 |
| WO | WO 2004/032937 | 4/2004 |

(56) References Cited

FOREIGN PATENT DOCUMENTS

| | | |
|---|---|---|
| WO | WO 2004/035052 | 4/2004 |
| WO | WO 2004/039782 | 5/2004 |
| WO | WO 2004/041308 | 5/2004 |
| WO | WO 2004/043472 | 5/2004 |
| WO | WO 2004/045523 | 6/2004 |
| WO | WO 2004/064730 | 8/2004 |
| WO | WO 2004/076412 | 9/2004 |
| WO | WO 2004/078144 | 9/2004 |
| WO | WO 2004/080462 | 9/2004 |
| WO | WO 2004/080966 | 9/2004 |
| WO | WO 2004/089286 | 10/2004 |
| WO | WO 2004/101526 | 11/2004 |
| WO | WO 2005/004870 | 1/2005 |
| WO | WO 2005/021537 | 3/2005 |
| WO | WO 2005/027972 | 3/2005 |
| WO | WO 2005/030140 | 4/2005 |
| WO | WO 2005/044788 | 5/2005 |
| WO | WO 2005/051366 | 6/2005 |
| WO | WO 2005/056764 | 6/2005 |
| WO | WO 2005/063713 | 7/2005 |
| WO | WO 2005/082854 | 9/2005 |
| WO | WO 2005/082855 | 9/2005 |
| WO | WO 2005/092896 | 10/2005 |
| WO | WO 2005/117867 | 12/2005 |
| WO | WO 2005/117887 | 12/2005 |
| WO | WO 2006/004636 | 1/2006 |
| WO | WO 2006/014325 | 2/2006 |
| WO | WO 2006/030826 | 3/2006 |
| WO | WO 2006/030941 | 3/2006 |
| WO | WO 2006/030947 | 3/2006 |
| WO | WO 2006/036941 | 4/2006 |
| WO | WO 2006/062984 | 6/2006 |
| WO | WO 2006/090930 | 8/2006 |
| WO | WO 2006/090931 | 8/2006 |
| WO | WO 2006/137474 | 12/2006 |
| WO | 2007/000347 | 1/2007 |
| WO | WO 2007/014335 | 2/2007 |
| WO | WO 2007/015569 | 2/2007 |
| WO | WO 2007/015578 | 2/2007 |
| WO | WO 2007/023768 | 3/2007 |
| WO | WO 2007/040565 | 4/2007 |
| WO | WO 2007/052849 | 5/2007 |
| WO | WO 2007/052850 | 5/2007 |
| WO | WO 2007/061127 | 5/2007 |
| WO | WO 2007/061130 | 5/2007 |
| WO | WO 2007/136103 | 11/2007 |
| WO | WO 2008/023698 | 2/2008 |
| WO | WO 2008/026577 | 3/2008 |
| WO | WO 2008/026748 | 3/2008 |
| WO | WO 2008/088088 | 7/2008 |
| WO | WO 2008/093855 | 8/2008 |
| WO | WO 2008/102870 | 8/2008 |
| WO | WO 2009/060945 | 5/2009 |
| WO | WO 2009/077874 | 6/2009 |
| WO | WO 2009/096377 | 8/2009 |
| WO | WO 2009/140549 | 11/2009 |

OTHER PUBLICATIONS

Almarsson et al., "High-Throughput Surveys of Crystal Form Diversity of Highly Polymorphic Pharmaceutical Compounds," Crystal Growth & Design, Sep. 10, 2003, 3(6):927-933.
Amendment filed in KR App. Ser. No. 10-2008-7027527, dated Jan. 27, 2014, 12 pages (with English translation).
Amendment filed in KR App. Ser. No. 10-2009-7017694, dated Feb. 28, 2014, 7 pages.
Appeal for Reversal in CO App. Ser. No. 12-022608, dated Jan. 28, 2014, 17 pages (with English translation).
Argument Brief filed in KR App. Ser. No. 10-2008-7029577, dated Feb. 27, 2014, 30 pages (with English translation).
Argument filed in KR App. Ser. No. 10-2009-7017694, dated Feb. 28, 2014, 48 pages.
Forbes et al., "Dissolution kinetics and solubilities of p-aminosalicylic acid and its salts," International Journal of Pharmaceutics, 126:199-208 (1995).
Montalbetti and Falque, "Tetrahedron report No. 740: Amide bond formation and peptide coupling," Tetrahedron, 2005, 61:10827-10852.
Notice of Allowance in CA App. Ser. No. 2661333, dated Dec. 19, 2013, 1 page.
Notice of Allowance in KR App. Ser. No. 10-2008-7027527, dated Mar. 3, 2014, 4 pages (with English translation).
Notice of Allowance in U.S. Appl. No. 12/524,754, dated Feb. 13, 2014, 18 pages.
Notice of Allowance in U.S. Appl. No. 12/741,682, dated Feb. 7, 2014, 11 pages.
Notice of Allowance in U.S. Appl. No. 13/083,338, dated Feb. 6, 2014, 15 pages.
Notice of Allowance in U.S. Appl. No. 13/205,328, dated Jan. 30, 2014, 11 pages.
Office Action in CA App. Ser. No. 2676796, dated Dec. 30, 2013, 5 pages.
Office Action in CN App. Ser. No. 200680020317.5, dated Mar. 4, 2014, 13 pages (with English translation).
Office Action in EP App. Ser. No. 04807580.8, dated Mar. 18, 2014, 12 pages.
Office Action in EP App. Ser. No. 08704376.6, dated Feb. 24, 2014, 4 pages.
Office Action in KR App. Ser. No. 10-2009-7017694, dated Jan. 29, 2014, 26 pages (with English translation).
Office Action in PH App. Ser. No. 1-2011-502441, dated Feb. 19, 2014, 2 pages.
Office Action in U.S. Appl. No. 11/662,425, dated Feb. 27, 2014, 152 pages.
Office Action in U.S. Appl. No. 11/997,543, dated Mar. 11, 2014, 20 pages.
Office Action in U.S. Appl. No. 12/039,381, dated Jan. 9, 2014, 16 pages.
Office Action in U.S. Appl. No. 13/983,891, dated Jan. 22, 2014, 11 pages.
O'Reilly et al., "Hydrolysis of tert-Butyl Methyl Ether (MTBE) in Dilute Aqueous Acid," Environ. Sci. Technol., 2001, 35:3954-3961.
Patel et al., "The effect of excipients on the stability of levothyroxine sodium pentahydrate tablets," Int'l J Pharm., 2003, 264:35-43.
Response filed in PH App. Ser. No. 1-2011-502441, dated Feb. 28, 2014, 4 pages.
Response to Office Action in CA App. Ser. No. 2661333, dated Nov. 12, 2013, 18 pages.
Response to Office Action in CN App. Ser. No. 200680020317.5 filed on Jan. 9, 2014, 7 pages (with English translation).
Response to Office Action in CN App. Ser. No. 201180030568.2 filed on Jan. 13, 2014, 46 pages (with English translation).
Response to Office Action in MX App. Ser. No. MX/a/2010/008187, dated Feb. 17, 2014, 7 pages (with English translation).
Response to Office Action in MX App. Ser. No. MX/a/2012/002011 filed on Jan. 16, 2014, 20 pages (with English translation).
Response to Office Action in RU App. Ser. No. 2013139556, dated Dec. 25, 2013, 10 pages (with English translation).
Response to Office Action in U.S. Appl. No. 13/983,891, dated Feb. 27, 2014, 6 pages.
Response to the Office Action issued for IN App. Ser. No. 6415/CHENP/2008 filed on Jan. 17, 2014, 16 pages.
Search Report in EP App. Ser. No. 11798224.9, dated Mar. 21, 2014, 1 page.
Search Report in EP App. Ser. No. 11798224.9, dated Mar. 4, 2014, 6 pages.
Stahl and Wermuth, "Handbook of Pharmaceutical Salts: Properties, selection, and use," 2002, pp. 117-122.
Submission documents re RCE filed in U.S. Appl. No. 12/741,682, dated Jan. 17, 2014, 1 page.
Submission documents re RCE in U.S. Appl. No. 12/439,339, dated Jan. 27, 2014, 1 page.
Submission documents re RCE in U.S. Appl. No. 12/524,754 filed on Feb. 3, 2014, 1 page.
Winkler et al., "Kinetics of vascular normalization by VEGFR2 blockade governs brain tumor response to radiation: Role of oxygenation, angiopoietin-1, and matrix metalloproteinases," Cancer Cell, Dec. 2004, 6:553-563.

(56) References Cited

OTHER PUBLICATIONS

Written Submission regarding hearing in IN App. Ser. No. 1571/CHENP/2007 filed on Jan. 23, 2014, 8 pages.
Zhang et al., "Synergic antiproliferative effect of DNA methyltransferase inhibitor in combination with anticancer drugs in gastric carcinoma," Cancer Sci., Sep. 2006, 97(9):938-944.
Amendment filed in KR App. Ser. No. 10-2008-7029472, dated May 1, 2014, 14 pages (with English translation).
Amendment filed in KR App. Ser. No. 10-2009-7005657, dated May 7, 2014, 15 pages (with English translation).
International Preliminary Report on Patentability in PCT App. Ser. No. PCT/US2012/040183, dated Apr. 3, 2014, 9 pages.
Nakazawa et al., "Maximizing the efficacy of anti-angiogenesis cancer therapy: A multi-targeting strategy by tyrosine kinase inhibitors," AACR Annual Meeting 2014, Presentation Abstract and Poster, Apr. 5-9, 2014, 2 pages.
Notice of Allowance in UA App. Ser. No. a201203132, dated Mar. 21, 2014, 6 pages.
Notice of Allowance in U.S. Appl. No. 12/439,339, dated Apr. 1, 2014, 17 pages.
Notice of Allowance in U.S. Appl. No. 12/741,682, dated May 15, 2014, 13 pages.
Notice of Allowance in U.S. Appl. No. 13/205,328, dated May 8, 2014, 10 pages.
Notice of Allowance in U.S. Appl. No. 13/983,891, dated Mar. 20, 2014, 9 pages.
Notice of Allowance in VN App. Ser. No. 1-2011-03484, dated Apr. 28, 2014, 2 pages.
Office Action in CN App. Ser. No. 201180030568.2, dated Mar. 24, 2014, 8 pages (with English translation).
Office Action in CN App. Ser. No. 201280010427.9, dated Mar. 31, 2014, 11 pages (with English translation).
Office Action in IL App. Ser. No. 227777, dated Mar. 12, 2014, 5 pages (with English translation).
Office Action in JP App. Ser. No. P2009-540099, dated Mar. 25, 2014, 6 pages (with English translation).
Office Action in KR App. Ser. No. 10-2008-7029472, dated Mar. 28, 2014, 6 pages (with English translation).
Office Action in KR App. Ser. No. 10-2009-7005657, dated Mar. 28, 2014, 6 pages (with English translation).
Office Action in MX App. Ser. No. MX/a/2012/014776, dated Apr. 4, 2014, 22 pages (with English Translation).
Office Action in U.S. Appl. No. 13/923,858, dated Apr. 18, 2014, 64 pages.
Office Action in U.S. Appl. No. 14/002,018, dated Apr. 14, 2014, 28 pages.
Response filed in VN App. Ser. No. 1-2011-03484, dated Feb. 28, 2014, 40 pages (with English translation).
Response to Office Action filed in EP App. Ser. No. 04807580.8, dated May 16, 2014, 13 pages.
Response to Office Action in EP App. Ser. No. 08704376.6, dated Apr. 30, 2014, 73 pages.
Response to Office Action in JP App. Ser. No. P2009-540099, dated Apr. 28, 2014, 9 pages (with English Translation).
Response to Office Action in SG App. Ser. No. 201108602-2, dated May 22, 2014, 37 pages.
Response to Office Action in U.S. Appl. No. 12/039,381, dated Apr. 3, 2014, 7 pages.
Shumaker et al., "Effect of lenvatinib (E7080) on the QTc interval: results from a thorough QT study in healthy volunteers," Cancer Chemother Pharmacol., published online Mar. 23, 2014, 9 pages.
Submission Documents re RCE filed in U.S. Appl. No. 12/741,682, dated May 6, 2014, 1 page.
Submission Documents re RCE filed in U.S. Appl. No. 13/083,338, dated May 6, 2014, 1 page.
Submission documents re RCE in U.S. Appl. No. 13/205,328, dated Apr. 28, 2014, 1 page.

"Clinical Trial: AMG 706 20040273 Thyroid Cancer Study: Stage 4 Cancer Treatments, Chat w/a Cancer Info Expert About Stage 4 Cancer Treatment Options," accessed from www.CancerCenter.com, 4 pages (2005).
"Arzneimittelwirkungen Lehrbuch der Pharmakologie und Toxikologie," Ernst Mutschler Ed Mutschler E et al., Arzneimittelwirkungen Lehrbuch der Pharmakologie und Toxikologie, Wissenschaftliche Verlagsgesellschaft, Stuttgart, Jan. 1, 1999, p1-p5, XP007919509 (English translation).
"Chapter 2.2 Loslichkeit, Losungsgeschwindigkeit, Loslichkeitsverbesserung," Rudolf Voigt Ed—Voigt R et al., Pharmazeutische Technologie fuer Studium and Beruf, DT. Apotheker-Verl, Stuttgart; DE, Jan. 1, 2000, p40-p52, XP008143620 (English translation).
AACR American Association Cancer Research, 92nd Annual Meeting, 42:583, Mar. 24-28, 2001, New Orleans, LA, USA, 3126.
AACR American Association Cancer Research, 96th Annual Meeting, 46:1407, (Abstract 5981), Anaheim, Orange County CA USA Apr. 16-20, 2005.
AACR American Association Cancer Research, 96th Annual Meeting, 46 (Abstract 3033), Anaheim, Orange County CA USA Apr. 16-20, 2005.
AACR American Association Cancer Research., 93nd Annual Meeting, 43:1080, Apr. 6-10, 2002, San Francisco, CA, USA, 5347.
AACR American Association Cancer Research., 96th Annual Meeting, 46, (Abstract 2031), Anaheim, Orange County, CA, USA Apr. 2005.
Abrams et al., SU11248 Inhibits KIT and Platelet-derived Growth Factor Receptor Beta in Preclinical Models of Human Small Cell Lung Lung *Cancer Molecular Cancer Therapeutics.*, 2: 471-478, 2003.
Abuzar et al., "Synthesis of some new 7-chloro-4-substituted quinolines as potential antiparasitic agents," *Eur. J. Med. Chem.*, 21(1):5-8 (1986).
Advisory Action for U.S. Appl. No. 12/092,539 issued on Jun. 28, 2011.
Agarwal et al., "Binding of discoidin domain receptor 2 to collagen I: an atomic force microscopy investigation," *Biochemistry*, 41(37):11091-11098 (2002).
Am. Assoc. Cancer Research, Abstract 5353, 2005.
Amended description filed after receipt of search report for EP Patent App. No. 10809938.3, filed Sep. 14, 2010.
Amended description filed after receipt of search report for EP Patent App. No. 10809938.3, filed Dec. 8, 2011.
Amendment after Allowance filed on Jan. 4, 2011 for CA App. Ser. No. 2426461.
Amendment and Response to Final Office Action under 37 C.F.R. §1.116 for U.S. Appl. No. 12/092,539, filed on Jun. 15, 2011.
Amendment and Response to Final Office Action under 37 C.F.R. §1.116 for U.S. Appl. No. 12/864,817, filed on Dec. 5, 2011.
Amendment and Response to Non-Final Office Action for U.S. Appl. No. 11/997,543, filed on Aug. 19, 2011.
Amendment and Response to Office Action under 37 C.F.R. § 1.111 dated Apr. 2, 2013 for U.S. Appl. No. 13/083,338.
Amendment and Response to Office Action under 37 C.F.R. §1.111 for U.S. Appl. No. 11/997,719, filed on Dec. 23, 2010.
Amendment and Response to Office Action under 37 C.F.R. §1.111 for U.S. Appl. No. 12/092,539, filed on Mar. 11, 2011.
Amendment and Response to Office Action under 37 C.F.R. §1.111 for U.S. Appl. No. 12/741,682, filed on Jul. 30, 2012.
Amendment and Response to Office Action under 37 C.F.R. §1.111 for U.S. Appl. No. 12/864,817, filed on Aug. 9, 2011.
Amendment and Response to Office Action under 37 C.F.R. §1.111 for U.S. Appl. No. 12/439,339, filed on Feb. 7, 2012.
Amendment and Response to Office Action under 37 C.F.R. §1.111 for U.S. Appl. No. 12/524,754, filed on Feb. 17, 2012.
Amendment and Response to Office Action under 37 C.F.R. §1.111 for U.S. Appl. No. 13/205,328, filed on Apr. 11, 2012.
Amendment and Response to Office Action under 37 C.F.R. §1.116 for U.S. Appl. No. 11/997,543, filed on Jan. 9, 2012.
Amendment and Response to Office Action under 37 C.F.R. §1.116 for U.S. Appl. No. 12/439,339, filed on Jul. 30, 2012.

(56) References Cited

OTHER PUBLICATIONS

Amendment filed on Apr. 11, 2006 for CN App. Ser. No. 01819710.8 (with English translation).
Amendment filed on Apr. 17, 2002 for TW App. Ser. No. 90125928 (with English translation).
Amendment filed on Apr. 19, 2005 for JP App. Ser. No. 2002-536056 (with English translation).
Amendment filed on Aug. 17, 2004 for ZA App. Ser. No. 2003/3567.
Amendment filed on Aug. 4, 2004 for ZA App. Ser. No. 2003/3567.
Amendment filed on Dec. 12, 2011 for JO Patent App. No. 55/2011 (with English translation).
Amendment filed on Dec. 15, 2011 for VN App. Ser. No. 1-2011-03484 (with English translation).
Amendment filed on Dec. 22, 2011 for ZA App. Ser. No. 2011/08697.
Amendment filed on Feb. 9, 2011 for TW App. Ser. No. 100104281.
Amendment filed on Jan. 11, 2010 for CN App. Ser. No. 200580026468.7 (with English translation).
Amendment filed on Jan. 26, 2010 for CN App. Ser. No. 200710007097.9 (with English translation).
Amendment filed on Jul. 2, 2009 for CN App. Ser. No. 200710007097.9 (with English translation).
Amendment filed on Jun. 22, 2010 for CN App. Ser. No. 200710007097.9 (with English translation).
Amendment filed on Mar. 20, 2012 for KR Patent App. No. 10-2012-7003846.
Amendment filed on Mar. 23, 2009 for JP App. Ser. No. 2005-124034 (with English translation).
Amendment filed on Mar. 6, 2006 for KR App. Ser. No. 10-2003-7005506 (with English translation).
Amendment filed on Mar. 7, 2005 for JP App. Ser. No. 2002-536056 (with English translation).
Amendment filed on Mar. 8, 2006 for KR App. Ser. No. 10-2005-7020292 (with English translation).
Amendment filed on May 10, 2012 for JP Patent Application No. 2011-527665.
Amendment filed on May 21, 2009 for JP App. Ser. No. 2005-124034 (with English translation).
Amendment filed on May 28, 2003 for CN App. Ser. No. 01819710.8 (with English translation).
Amendment filed on Nov. 19, 2009 for CN App. Ser. No. 200710007097.9 (with English translation).
Amendment filed on Nov. 24, 2011 for KR App. Ser. No. 10-2007-7001347 (with English translation).
Amendment filed on Oct. 25, 2005 for KR App. Ser. No. 10-2003-7005506 (with English translation).
Amendment filed on Oct. 28, 2011 for LB Patent App. No. 9292.
Amendment filed on Oct. 9, 2006 for CN App. Ser. No. 01819710.8 (with English translation).
Amendment filed on Sep. 13, 2005 for CN App. Ser. No. 01819710.8 (with English translation).
Amendment filed on Sep. 23, 2009 for CN App. Ser. No. 200580026468.7 (with English translation).
Amendment for New Zealand Patent Application No. 598291 dated Jan. 30, 2013.
Amendments received before examination for EP App. Ser. No. 01976786.2, dated Sep. 10, 2004.
Amendments to the specification filed on Mar. 26, 2012 for AU Patent Appl. No. 2010285740.
American Association for Cancer Research, "Redefining the Frontiers of Science," 94th Annual Meeting, vol. 44, 2nd Edition, Washington Convention Center, Washington, DC (Jul. 11-14, 2003).
Amino et al., "YM-231146, a Novel Orally Sioavailable Inhibitor of Vascular Endothelial Growth Factor Receptor-2, Is Effective against Paclitaxel Resistant Tumors", Biological and Pharmaceutical Bulletin. 28:2096-2101, 200.
Anderson et al., "Preparation of Water -soluble Compounds through Salt Formation. The Practice of Medicinal Chemistry," *Technomics*, 347-349 and 355-356 (Sep. 25, 1999).

Anonymous, "Scientific Discussion," EMEA, URL: htttp://www.ema.europa.eu/docs/en_GB/document_library/EPARScientific_Discussion/human/000406/WC500022203.pdf, 1-61 (2004) (XP007918143).
Approval of request for amendments for EP App. Ser. No. 04025700.8, dated Mar. 13, 2008.
Argument Brief filed on Mar. 6, 2006 for KR App. Ser. No. 10-2003-7005506 (with English translation).
Argument Brief filed on Mar. 8, 2006 for KR App. Ser. No. 10-2005-7020292 (with English translation).
Argument Brief filed on Nov. 24, 2011 for KR App. Ser. No. 10-2007-7001347 (with English translation).
Argument Brief filed on Oct. 25, 2005 for KR App. Ser. No. 10-2003-7005506 (with English translation).
Argument filed on Apr. 19, 2005 for JP App. Ser. No. 2002-536056 (with English translation).
Argument filed on Mar. 23, 2009 for JP App. Ser. No. 2005-124034 (with English translation).
Argument filed on May 21, 2009 for JP App. Ser. No. 2005-124034 (with English translation).
Asano et al , "Inhibition of Tumor Growth and Metastasis by an Immunoneutralizing Monoclonal Antibody to Human Vascular Endothelial Growth Factor/Vascular Permeability Factor121", Cancer Research., 55, 5296-5301, 1995.
*Asu no Shinyaku* ("The New Drugs of Tomorrow"), editing/printing by Technomics, Inc., 81-83 (Dec. 2006) (English translation), 14 pages.
Australian Office Action for App. Ser. No. 2008205847, issued on Apr. 11, 2012.
Australian Office Action for App. Ser. No. 2008211952, issued on Apr. 3, 2012.
Australian Office Action for Application No. 2006309551 issued on Feb. 2, 2012.
Australian Office Action for Application No. AU2006309551 issued on Apr. 28, 2011.
Australian Response to Office Action for Application No. 2006309551 filed on Jan. 27, 2012.
Bainbridge et al., "A peptide encoded by exon 6 of VEGF (EG3306) inhibits VEGF-induced angiogenesis in vitro and ischaemic retinal neovascularisation in vivo", Biochem Biophys Res Commun., 302, 793-799, 2003.
Baker et al., "Blockade of vascular endothelial growth factor receptor and epidermal growth factor receptor signaling for therapy of metastatic human pancreatic cancer," *Cancer Res.*, 62:1996-2003 (2002).
Bankston et al., "A Scaleable synthesis of BAY 43/9006: A Potent Raf Kinase Inhibitor for the Treatment of Cancer", Organic Process Res Dev., 6:777-81 (2002).
Bartsch et al., "A RET double mutation in the germline of a kindred with FMTC", Exp. Clin Endocrinol Diabetes, 108, 128-132, 2000.
Bastin et al., "Salt Selection and Optimisation Procedures for Pharmaceutical New Chemical Entities," *Organic Process Research & Development*, 4(5):427-435 (2000) (XP002228592).
Beebe et al., "Pharmacological Characterization of CP-547,632, a Novel Vascular Endothelial Growth Factor Receptor-2 Tyrosine Kinase Inhibitor for Cancer Therapyl", Cancer Research. 63:7301-9, 2003.
Bellone et al., "Growth Stimulation of Colorectal Carcinoma Cells via the c-kit Receptor is Inhibited by TGF-β-1," *Journal of Cellular Physiology*, 172:1-11 (1997).
Benjamin et al., "Selective ablation of immature blood vessels in established human tumors follows vascular endothelial growth factor withdrawal," *J. Clin. Invest.*, 103(2):159-165 (1999).
Berdel et al., "Recombinant Human Stem Cell Factor Stimulates Growth of a Human Glioblastoma Cell Line Expressing c-kit Protooncogene," *Cancer Res.*, 52:3498-3502 (1992).
Berge et al., "Pharmaceutical Salts," *Journal of Pharmaceutical Sciences*, 66(1):1-19 (Jan. 1977) (XP002550655).
Bergers et al., "Benefits of targeting both pericytes and endothelial cells in the tumor vasculature with kinase inhibitors," *J. Clin. Invest.*, 111(9):1287-1295 (2003).
Bernex et al., "Spatial and temporal patterns of c-kit-expressing cells in WlacZ/+ and WlacZ/WlacZ mouse embryos", Development 122:3023-3033 (1996).

(56) References Cited

OTHER PUBLICATIONS

Blume-Jensen et al., "Activation of the Human c-kit Product by Ligand-Induced Dimerization Mediates Circular Actin Reorganization and Chemotaxis," *The EMBO Journal*, 10(13):4121-4128 (1991).
Boissan et al., "c-Kit and c-kit mutations in mastocytosis and other hematological diseases," *J. Leukocyte Biol.*, 67:135-148 (2000).
Bold et al., "New anilinophthalazines as potent and orally well absorbed inhibitors of the VEGF receptor tyrosine kinases useful as antagonists of tumor-driven angiogenesis", Journal of Medicinal Chemistry., 43:2310-2323 (2000).
Bradley Anderson et al., "Preparation of Water-soluble Compounds through Salt Formation", The Practice of Medicinal Chemistry, *Technomics*, pp. 347-349, 355-356 (1999).
Bramhall, S., "The Matrix Metalloproteinases and Their Inhibitors in Pancreatic Cancer", International J. Pancreatol., 21, 1-12, 1997.
Brief communication to applicant for EP App. Ser. No. 01976786.2, dated Sep. 9, 2005.
Bruns et al., "Effect of the vascular endothelial growth factor receptor-2 antibody DC101 plus gemcitabine on growth, metastasis and angiogenesis of human pancreatic cancer growing orthotopically in nude mice," *J. Cancer*, 102:101-108 (2002).
Bussolino et al., "Role of Soluble Mediators in Angiogenesis," *Eur. J. Cancer*, 32A(14):2401-2412 (1996).
Cairns et al., "New antiallergic pyrano[3,2g]quinoline-2,8-dicarboxylic acids with potential for the topical treatment of asthma," *J. Med. Chem.*, 28(12):1832-1842 (1985).
Canadian Office Action for App. Ser. No. 2426461, dated Dec. 6, 2007.
Canadian Office Action for App. Ser. No. 2426461, dated Feb. 10, 2010.
Canadian Office Action for App. Ser. No. 2426461, dated May 8, 2009.
Canadian Office Action for App. Ser. No. 2426461, dated Nov. 20, 2008.
CancerCare, "Types of Lung Cancer," Cancer Care, Inc [online] [retrieved on Nov. 12, 2009]. Retrieved from the Internet: www.lungcancer.org/reading/types.php?printable=true (2009).
Cappellen et al., "Frequent activating mutations of FGFR3 in human bladder and cervix carcinomas," *Nat. Genet.*, 23:18-20 (1999).
Carlomagno et al., "BAY 43-9006 inhibition of oncogenic RET mutants," *J. Natl. Cancer Inst.*, 98(5):326-34 (2006).
Carlomagno et al., "ZD6474, an orally available inhibitor of KDR tyrosine kinase activity, efficiently blocks oncogenic RET kinases," *Cancer Res.*, 62:7284-7290 (2002).
Carter et al, "Inhibition of drug-resistant mutants of ABL, KIT and EGF receptor kinases", Proceedings of the National Academy of Sciences of the United States of America., 102, 11011-11016, 2005.
Cell Technology, Supplementary Volume, "Bio-Experiment Illustrated vol. 5, No Fear of Proteins", Visual Laboratory Notebook Series, Section 6, Immunostaining, pp. 127-163, Shujunsha, Co., Ltd., 1997 (Japanese).
Chen et al., "FGFR3 as a therapeutic target of the small molecule inhibitor PKC412 in hematopoietic malignancies," *Oncogene*, 24:8259-8267 (2005).
Chesi et al., "Activated fibroblast growth factor receptor 3 is an oncogene that contributes to tumor progression in multiple myeloma," *Blood*, 97:729-736 (2001).
Chesi et al., "Frequent translocation t(4;14)(p16.3;q32.3) in multiple myeloma is associated with increased expression and activating mutations of fibroblast growth factor receptor 3," *Nat. Genet.*, 16:260-264 (1997).
Chinese Office Action for App. Ser. No. 200580026468.7, issued on Jun. 26, 2009.
Chinese Office Action for App. Ser. No. 200710007097.9, issued on Mar. 6, 2009.
Chinese Office Action for App. Ser. No. 200780017371.9, issued on Mar. 7, 2012 (with English translation).
Chinese Office Action for App. Ser. No. 200880002425.9, issued on Mar. 7, 2012 (with English translation).
Chinese Office Action for App. Ser. No. 200880003336.6, issued on May 24, 2011(with English translation).
Chinese Office Action for App. Ser. No. 200880115011.7, issued on Feb. 20, 2012 (with English translation).
Chinese Office Action for App. Ser. No. 201080030508.6, issued on Nov. 30, 2012 (with English translation).
Chinese Office Action for Application No. 200680041355.9 issued on Mar. 5, 2010 with English translation.
Chinese Office Action for Application No. 200680041355.9 issued on Aug. 24, 2010 with English translation.
Chinese Response to Office Action for Application No. 200680041355.9 filed on Jul. 19, 2010 with English translation.
Chinese Response to Office Action for Application No. 200680041355.9 filed on Nov. 8, 2010 with English translation.
Ciardiello et al., "ZD1839 (IRESSA), an EGFR-selective tyrosine kinase inhibitor, enhances taxane activity in bcl-2 overexpressing, multidrug-resistant MCF-7 ADR human breast cancer cells," *Int. J. Cancer*, 98:463-469 (2002).
Clark et al., "Safety and Pharmacokinetics of the Dual Action Raf Kinase and Vascular Endothelial Growth Factor Receptor Inhibitor, BAY43-9006, in Patients with Advanced Refractory Solid Tumors ," *Clin. Cancer Res.*, 11:5472-5480 (2005).
ClinicalTrials.gov, "A Study of E7080 Alone, and in Combination With Everolimus in Subjects With Unresectable Advanced or Metastatic Renal Cell Carcinoma Following One Prior Vascular Endothelial Growth Factor (VEGF)-Targeted Treatment," National Institutes of Health, Food and Drug Administration, National Library of Medicine, [online] [retrieved on Sep. 27, 2010]. Retrieved from the Internet: http://clinicaltrials.gov/ct2/show/NCT01136733, (May 26, 2010).
CN200780032071.8 Office Action issued on Oct. 13, 2010 with English translation.
CN200780032071.8 Response to Office Action filed on Feb. 16, 2011 with English translation.
Cohen et al., "Expression of Stem Cell Factor and c-kit in Human Neuroblastoma," Blood, 84(10):3465-3472 (1994).
Communication about intention to grant a European patent for EP App. Ser. No. 01976786.2, dated Sep. 4, 2006.
Communication about intention to grant a European patent for EP App. Ser. No. 04025700.8, dated Oct. 15, 2007.
Communication about intention to grant a European patent for EP App. Ser. No. 05783232.1, dated Nov. 20, 2008.
Communication about intention to grant a European patent for EP App. Ser. No. 06023078.6, dated Jul. 18, 2008.
Communication from the Examining Division for EP App. Ser. No. 01976786.2, dated Aug. 17, 2005.
Communication from the Examining Division for EP App. Ser. No. 01976786.2, dated Sep. 19, 2005.
Communication from the Examining Division for EP App. Ser. No. 01976786.2, dated Mar. 21, 2006.
Communication from the Examining Division for EP App. Ser. No. 04025700.8, dated Apr. 10, 2006.
Communication from the Examining Division for EP App. Ser. No. 04025700.8, dated Oct. 23, 2006.
Communication from the Examining Division for EP App. Ser. No. 05783232.1, dated Feb. 7, 2008.
Communication from the Examining Division for EP App. Ser. No. 06023078.6, dated Aug. 2, 2007.
Communication from the Examining Division for EP App. Ser. No. 06023078.6, dated Sep. 26, 2007.
Communication regarding the expiry of opposition period for EP App. Ser. No. 01976786.2, dated Jan. 4, 2008.
Communication regarding the expiry of opposition period for EP App. Ser. No. 04025700.8, dated May 7, 2009.
Communication regarding the expiry of opposition period for EP App. Ser. No. 05783232.1, dated Feb. 19, 2010.
Communication regarding the expiry of opposition period for EP App. Ser. No. 06023078.6, dated Nov. 4, 2009.
Continuation Patent Application, Preliminary Amendment and Information Disclosure Statement filed Jun. 21, 2013, Jun. 24, 2013 and Jun. 25, 2013 in U.S. Appl. No. 13/923,858, 97 pages.
Corbin et al., "Sensitivity of oncogenic KIT mutants to the kinase inhibitors MLN518 and PD180970", *Blood.*, 104, 3754-3757, 2004.

(56) References Cited

OTHER PUBLICATIONS

Croom et al., "Imatinib mesylate," *Drugs*, 63(5):513-522 (2003).
Da Silva et al., "A novel germ-line point mutation in RET exon 8 (Gly(533)Cys) in a large kindred with familial medullary thyroid carcinoma," *J. Clin. Endocrinol. Metab.*, 88:5438-5443 (2003).
David et al., "A Phase I Trial of the Epidermal Growth Factor Receptor (EGFR)-Directed Bispecific Antibody (BsAB) MDX-447 in Patients with Solid Tumors. (Meeting abstract).", ASCO 18: 433, Abstract 1999.
De Lange et al., "Phase II trial of cisplatin and gemcitabine in patients with advanced gastric cancer," *Annals of Oncology*, 15:484-488 (2004).
Decision to grant a European patent for EP App. Ser. No. 01976786.2, dated Feb. 1, 2007.
Decision to grant a European patent for EP App. Ser. No. 04025700.8, dated Jun. 5, 2008.
Decision to grant a European patent for EP App. Ser. No. 05783232.1, dated Mar. 19, 2009.
Decision to grant a European patent for EP App. Ser. No. 06023078.6, dated Dec. 4, 2008.
Deficiencies in sequence listing for EP App. Ser. No. 06023078.6, dated Dec. 5, 2006.
Deplanque et al., "Anti-Angiogenic Agents: Clinical Trial Design and Therapies in Development," *European Journal of Cancer*, 36:1713-1724 (2000).
Dermer, "Another Anniversary for the War on Cancer," *Bio/Technology*, 12:320 (1994).
Di Raimondo et al., "Antiogenic Factors in multiple myeloma: higher levels in bone than in peripheral blood," *Haematologica*, 85:800-805 (2000).
Dias et al., "IL-12 Regulates VEGF and MMPs in a Murine Breast Cancer Model", International J. Cancer., 78, 361-5, 1998.
DiLorenzo et al., "Targeted Therapy in the Treatment of Metastatic Renal Cell Cancer," *Oncology*, 77(suppl 1):122-131 (2009).
Dourisboure et al, "Penetrance and Clinical Manifestations of Non-Hotspot Germ line RET Mutation, C630R, in a Family with Medullary Thyroid Carcinoma", Thyroid, 15, 668-671, 2005.
Dvorakova et al., "Exon 5 of the RET proto-oncogene: A newly detected risk exon for familial medullary thyroid carcinoma, a novel germ-line mutation Gly321Arg", Journal of Endocrinological Investigation, 28, 905-909, 2005.
El-Abseri et al., "Chemoprevention of UV Light-Induced Skin Tumorigenesis by Inhibition of the Epidermal Growth Factor Receptor", Cancer Research., 64, 3958-3965, 2004.
Elisei et al., "Identification of a novel point mutation in the RET gene (Ala883Thr), which is associated with medullary thyroid carcinoma phenotype only in homozygous condition," *J. Clin. Endocrinol. Metab.*, 89:5823-5827 (2004).
Emanuel et al., "A Vascular Endothelial Growth Factor Receptor-2 Kinase Inhibitor Potentiates the Activity of the Conventional Chemotherapeutic Agents Paclitaxel and Doxorubicin in Tumor Xenograft Models", Molecular Pharmacology., 66, 635-647, 2004.
EP Communication under Rule 71(3) EPC for Application No. 06832529.9 issued on Nov. 25, 2011.
EP07806561.2 Office Action issued on Dec. 9, 2011.
EP07806561.2 Office Actions issued on Jan. 19 and Feb. 7, 2011.
EP07806561.2 Response to Office Action filed on Aug. 9, 2011.
Erber et al., "Combined inhibition of VEGF and PDGF signaling enforces tumor vessel regression by interfering with pericyte-mediated endothelial cell survival mechanisms," *FASEB J.*, 18(2):338-340 (2004).
European Office Action for App. Ser. No. 04719054.1, issued on Oct. 30, 2009.
European Office Action for App. Ser. No. 04807580.8, issued on Apr. 18, 2011.
European Office Action for App. Ser. No. 04807580.8, issued on Dec. 3, 2010.
European Office Action for App. Ser. No. 04807580.8, issued on Oct. 25, 2011.
European Office Action for App. Ser. No. 04818213.3, issued on Feb. 2, 2012.
European Office Action for App. Ser. No. 07743994.1, issued on Oct. 10, 2012.
European Office Action for App. Ser. No. 4025700.8, issued on Apr. 10, 2006.
European Office Action for Application No. 06832529.9 issued on Oct. 15, 2009.
European Office Action for Application No. 06832529.9 issued on Sep. 12, 2011.
European Response to Office Action for Application No. 06832529.9 filed on Apr. 22, 2010.
European Response to Office Action for Application No. 06832529.9 filed on Oct. 4, 2011.
European Search Report directed at application No. 06768437.3, issued on Oct. 11, 2010.
European Search Report directed at application No. 06782407.8, issued on Jul. 23, 2010.
European Search Report directed at application No. 06832529.9, issued on Jul. 29, 2009.
European Search Report directed at application No. 06833681.7, issued on Nov. 24, 2010.
European Search Report directed at application No. 07743994.1, issued on May 4, 2010.
European Search Report directed at application No. 07806561.2, issued on Jan. 19, 2011.
European Search Report directed at application No. 10015141.4, issued on Sep. 9, 2011.
European Search Report for App. Ser. No. 03791389.4, issued on Jul. 7, 2011.
European Search Report for App. Ser. No. 04025700.8, dated Jan. 13, 2005.
European Search Report for App. Ser. No. 04719054.1, issued on Apr. 17, 2009.
European Search Report for App. Ser. No. 04818213.3, issued on Jul. 30, 2007.
European Search Report for App. Ser. No. 05783232.1, issued on Sep. 7, 2007.
European Search Report for App. Ser. No. 06023078.6, issued on Mar. 16, 2007.
European Search Report for App. Ser. No. 06767145.3, issued on May 23, 2011.
European Search Report for App. Ser. No. 10809938.3, issued on Jan. 2, 2013.
Examination Report dated Feb. 18, 2005 for NZ App. Ser. No. 525324.
Examination Report dated Feb. 21, 2008 for AU App. Ser. No. 2006203099.
Examination Report dated Jan. 30, 2013 for AU App. Ser. No. 2009210098.
Examination Report dated Mar. 26, 2008 for AU App. Ser. No. 2006236039.
Examination Report dated May 4, 2006 for AU App. Ser. No. 2001295986.
Examination Report dated Nov. 24, 2012 for AU App. Ser. No. 2008325608.
Examination Report dated Oct. 13, 2003 for NZ App. Ser. No. 525324.
Examination Report dated Sep. 2, 2004 for NZ App. Ser. No. 525324.
Examination Report dated Sep. 20, 2005 for AU App. Ser. No. 2001295986.
Experimental Medicine, Supplementary Volume, "A New Handbook of Genetic Engineering", Section 4, YODOSHA, 2003(Japanese).
Explanation of Circumstances Concerning Accelerated Examination filed May 10, 2012 for JP Patent Application No. 2011-527665.
Extended European Search Report dated Feb. 21, 2013 for EP App. Ser. No. 12195436.6, 8 pages.
Final Office Action for U.S. Appl. No. 12/092,539 issued on May 9, 2011.
Final Rejection dated May 21, 2013 for JP App. Ser. No. P2008-532141, 4 pages (with English translation).
Folkman et al., "Angiogenesis," *The Journal of Biological Chemistry*, 267(16): 10931-10934 (1992).

(56) References Cited

OTHER PUBLICATIONS

Folkman et al., "Clinical Applications of Research on Angiogenesis," *The New England Journal of Medicine*, 333(26):1757-1763 (1995).
Folkman et al., "What is the Evidence That Tumors are Angiogenesis Dependent?," *Journal of the National Cancer Institute*, 82(1):4-6 (1990).
Folkman, "New Perspective in Clinical Oncology From Angiogenesis Research," *J. Eur. J Cancer*, 32A(4):2534-2539 (1996).
Fong et al., "SU5416 Is a Potent and Selective Inhibitor of the Vascular Endothelial Growth Factor Receptor (Flk-1/KDR) That Inhibits Tyrosine Kinase Catalysis, Tumor Vascularization, and Growth of Multiple Tumor Types", Cancer Research., 59, 99-106, 1999.
Formality Requirement dated Jun. 18, 2003 for PH App. Ser. No. 1-2003-500266.
Freshney, R. Ian, "Culture of Animal Cells, a Manual of Basic Technique," Alan R. Liss, New York, 29-32 (1983).
Fugazzola et al., "Molecular and biochemical analysis of RET/PTC4, a novel oncogenic rearrangement between RET and ELE1 genes, in a post-Chernobyl papillary thyroid cancer", Oncogene, 13, 1093-1097, 1996.
Funahashi et al., "P-2123, Lenvatinib treatment of differentiated thyroid cancer (DTC): Analysis to identify biomarkers associated with response," The 71$^{st}$ Annual Meeting of the Japanese Cancer Association, Sep. 19-21, 2012, p. 339.
Furitsu et al., "Identification of Mutations in the Coding Sequence of the Proto-Oncogene c-kit in a Human Mast Cell Leukemia Cell Line Causing Ligand-Independent Activation of c-kit Product," *J. Clin. Invest.*, 92:1736-1744 (1993).
Furitsu et al., "Stable medicinal compositions of quinolinecarboxamide derivative," Database Caplus Chemical Abstracts Service, Columbus, OH, US (2006) (XP002520305).
Furuta et al., "Synthesis and Biological Evaluation of Selective Inhibitors of PDGF Receptor Auto Phosphorylation," #64, *American Chemical Society, 226$^{th}$ ACS National Meeting*, New York, NY (Sep. 7-11, 2003).
Gall-Istok et al., "Notes on the Synthesis of 4-Amino-6,7-Di-Sec-Butoxyquinoline, -6,7-Methylene-Dioxyquinoline and its N-Alkylaminoacetyl Derivatives," *Acta Chimica Hungarica*, 112(2):241-247 (1983).
Gardner et al., "In Vitro Activity Sorghum-Selective Fluorophenyl Urea Herbicides," *Pesticide Biochemistry and Physiology*, 24(3):285-297 (1985).
Gatzemeier et al., "Phase III comparative study of high-dose cisplatin versus a combination of paclitaxel and cisplatin in patients with advanced non-small-cell lung cancer," *J. Clin. Oncol.*, 18(19):3390-3399 (2000).
Genitourinary Cancers, Prostate Cancer Genitourinary, http://www.merkmanuals.com/professional/print/sec17/ch241/ch241e.html Mar. 16, 2011.
Giles, "The vascular endothelial growth factor (VEGF) signaling pathway: a therapeutic target in patients with hematologic malignancies," *Oncologist*, 6(suppl 5):32-39 (2001).
Gingrich et al., "A New Class of Potent Vascular Endothelial Growth Factor Receptor Tyrosine . . . Clinical Candidate CEP-7055", Journal of Medicinal Chemistry., 46: 5375-88, 2003.
Golkar et al., "Mastocytosis," *Lancet*, 349:1379-1385 (1997).
Gould, "Salt Selection for Basic Drugs," *International Journal of Pharmaceutics*, 33:201-217, (1986) (XP025813036).
Guo et al., "Expression of gastric cancer-associated MG7 antigen in gastric cancer, precancerous lesions and *H. pylori*-associated gasteric diseases", *Word J. Gastroenterol*, 8(6):1009-101 (2002).
Guo et al., "In Vitro Pharmacological Characterization of TKI-28, a Broad-Spectrum Tyrosine Kinase Inhibitor with Anti-Tumor and Anti-Angiogenic Effects", Cancer Biol Ther., 4, p. 1125-1132, 2005.
Gura, "Cancer Models Systems for Identifying new drugs are often faulty," *Science*, 278:1041-1042 (1997).

Gutheil et al., Targeted Antiangiogenic Therapy for Cancer Using Vitaxin: A Humanized Monoclonal Antibody to the Integrin alphavbeta3 1 Clinical Cancer Research., 6, 3056-61, 2000.
Haleblian,"Characterization of habits and crystalline modification of solids and their pharmaceutical applications," *J. Pharm. Sci.*, 64(8):1269-1288 (1975).
Haller, "Chemotherapy for advanced pancreatic cancer," *Int. J Radiation Oncol. Biol. Phys.*, 56:16-23 (2003).
Hamby et al., "Structure-Activity Relationships for a Novel Series of Pyrido[2,3-d]pyrimidine Tyrosine Kinase Inhibitors", *Journal of Medicinal Chemistry.*, 40, 2296-2303, 1997.
Hamel et al., "The Road Less Travelled: c-kit and Stem Cell Factor," *Journal of Neuro-Oncology*, 35:327-333 (1997).
Hara et al., "Amplification of c-myc, K-sam, and c-met in Gastric Cancers: Detection by Fluorescence in Situ Hybridization", Laboratory Investigation, 78, 1143-1153, 1998.
Hattori et al., "Immunohistochemical detection of K-sam protein in stomach cancer," *Clin. Cancer Res.*, 2(8):1373-1381 (1996).
Hayamo et al., "Pericytes in experimental MDA-MB231 tumor angiogenesis," *Histochemistry and Cell Biology*, 117(6):527-534, Abstract (Jun. 2002).
Hayek et al., "An in Vivo Model for Study of the Angiogenic Effects of Basic Fibroblast Growth Factor," *Biochemical and Biophysical Research Communications*, 147(2):876-880 (1987).
Heinemann, V., et al., "Comparison of the Cellular Pharmacokinetics and Toxicity of . . . 1-beta-d-Arabinofuranosylcytosine", Cancer Research, 48, 4024-4031, 1988.
Heinrich et al., "Inhibition of c-kit receptor tyrosine kinase activity by STI 571, a selective tyrosine kinase inhibitor," *Blood*, 96(3):925-932 (2000) (XP001097629).
Heinrich et al., "Inhibition of KIT tyrosine kinase activity: a novel molecular approach to the treatment of KIT-positive malignancies," *J. Clin. Oncol.*, 20(6):1692-1703 (2002).
Hennequin et al., "Design and Structure-Activity Relationship of a New Class of Potent VEGF Receptor Tyrosine Kinase Inhibitors", Journal of Medicinal Chemistry., 42: 5369-5389, 1999Wedge.
Hennequin et al., "Novel 4-Anilinoquinazolines with C-7 Basic Side Chains: Design and Structure Activity Relationship of a Series of Potent, Orally Active, VEGF Receptor Tyrosine Kinase Inhibitors", Journal of Medicine Chemistry 45:1300-1312 (2002).
Hertel LW., et al., "Evaluation of the Antitumor Activity of Gemcitabine (2',2' -Difluoro-2'-deoxycytidine)", Cancer Research, 50, 4417-4422, 1990.
Hibi et al., "Coexpression of the Stem Cell Factor and the c-kit Genes in Small-Cell Lung Cancer," *Oncogene*, 6:2291-2296 (1991).
Highlights of Prescribing Information: GLEEVEC® (imatinib mesylate) Tablets for Oral Use (Initial U.S. Approval 2001; Label Revised Jan. 2012).
Hines et al., "Coexpression of the c-kit and Stem Cell Factor Genes in Breast Carcinomas," *Cell Growth & Differentiation*, 6:769-779 (1995).
Hogaboam et al., "Novel Role of Transmembrane SCF for Mast Cell Activation and Eotaxin Production in Mast Cell-Fibroblast Interactions," *J. Immunol.*, 160:6166-6171 (1998).
Hori et al., "Suppression of Solid Tumor Growth by Immunoneutralizing Monoclonal Antibody against Human Basic Fibroblast Growth Factor", Cancer Research., 51, 6180-4, 1991.
Hurwitz et al., "Bevacizumab plus irinotecan, fluorouracil, and leucovorin for metastatic colorectal cancer," *N. Engl. J. Med.*, 350(23):2335-2342 (2004).
Huston et al., "Protein engineering of antibody binding sites: Recovery of specific activity in an anti-digoxin single-chain Fv analogue produced in *Escherichia coli*", *Proc. Natl. Acad. Sci. USA* 85: 5879-83, 1988.
Ikeda et al., "Changes in Phenotype and Proliferative Potential of Human Acute Myeloblastic Leukemia Cells in Culture with Stem Cell Factor," *Experimental Hematology*, 21:1686-1694 (1993).
Ikeda et al., "Expression and Functional Role of the Proto-Oncogene c-kit in Acute Myeloblastic Leukemia Cells," *Blood*, 78(11):2962-2968 (1991).
Inai et al., "Inhibition of vascular endothelial growth factor (VEGF) signaling in cancer causes loss of endothelial fenestrations, regres-

(56) References Cited

OTHER PUBLICATIONS sion of tumor vessels, and appearance of basement membrane ghosts," *American Journal of Pathology*, 165:35-52 (2004).
Indian Office Action for App. Ser. No. 1571/CHENP/2007, issued on Oct. 30, 2012.
Indian Office Action for U.S. App. Ser. No. 383/CHENP/2008, issued on May 3, 2012.
Information about decision on request for EP App. Ser. No. 06023078.6, dated Mar. 21, 2007.
Inoue et al., "Molecular Target Therapy Targeting Angiogenesis Pathways," *The Nishinihon Journal of Urology*, 66:425-432 (2004).
International Preliminary Report on Patentability for App. Ser. No. PCT/JP01/09221, dated Jan. 8, 2003.
International Preliminary Report on Patentability for App. Ser. No. PCT/JP2004/003087, issued on Feb. 13, 2006.
International Preliminary Report on Patentability for App. Ser. No. PCT/JP2005/016941, dated on Mar. 20, 2007.
International Preliminary Report on Patentability for App. Ser. No. PCT/JP2006/312487, issued on Jan. 10, 2008.
International Preliminary Report on Patentability for App. Ser. No. PCT/JP2010/063804, issued on Mar. 13, 2012.
International Preliminary Report on Patentability for App. Ser. No. PCT/JP2011/064430, dated Jan. 24, 2013, 6 pages.
International Search Repo rt for App. Ser. No. PCT/JP2008/051024, issued on Apr. 1, 2008.
International Search Report for App. Ser. No. PCT/JP01/09221, issued on Jan. 15, 2002.
International Search Report for App. Ser. No. PCT/JP2004/003087, issued on Jul. 13, 2004.
International Search Report for App. Ser. No. PCT/JP2005/016941, dated on Nov. 15, 2005.
International Search Report for App. Ser. No. PCT/JP2006/315563, issued on Sep. 5, 2006.
International Search Report for App. Ser. No. PCT/JP2006/315698, issued on Oct. 17, 2006.
International Search Report for App. Ser. No. PCT/JP2006/322514, issued on Jan. 23, 2007.
International Search Report for App. Ser. No. PCT/JP2006/323881, issued on Jan. 23, 2007.
International Search Report for App. Ser. No. PCT/JP2007/060560, issued on Sep. 11, 2007.
International Search Report for App. Ser. No. PCT/JP2007/063525, issued on Sep. 4, 2007.
International Search Report for App. Ser. No. PCT/JP2007/067088, issued on Nov. 20, 2007.
International Search Report for App. Ser. No. PCT/JP2008/051697, issued on Mar. 4, 2008.
International Search Report for App. Ser. No. PCT/JP2008/070321, issued on Jun. 20, 2009.
International Search Report for App. Ser. No. PCT/JP2009/051244, issued on Mar. 24, 2009.
International Search Report for App. Ser. No. PCT/JP2010/063804, issued on Sep. 14, 2010.
Invitation to declare maintenance of the application for EP App. Ser. No. 01976786.2, dated Jul. 12, 2004.
Invitation to declare maintenance of the application for EP App. Ser. No. 05783232.1, dated Sep. 25, 2007.
Invitation to declare maintenance of the application for EP App. Ser. No. 06023078.6, dated May 2, 2007.
IPRP (PCT/JP2007/067088) dated Mar. 3, 2009 with English translation.
Israeli Office Action for App. Ser. No. 155447, issued on Oct. 16, 2007 (with English translation).
Israeli Office Action for App. Ser. No. 189677, issued on Feb. 18, 2009 (with English translation).
Israeli Office Action for App. Ser. No. 195282, issued on Feb. 5, 2012 (with English translation).
Israeli Office Action for App. Ser. No. 199907, issued on Apr. 22, 2012 (with English translation).
Itoh et al., "Preferential alternative splicing in cancer generates a K-sam messenger RNA with higher transforming activity," *Cancer Res.*, 54:3237-3241 (1994).
Jakeman et al., "Developmental Expression of Binding Sites and Messenger Ribonucleic Acid for Vascular Endothelial Growth Factor Suggests a Role for This Protein in Vasculogenesis and Angiogenesis," *Endocrinology*, 133(2):848-859 (1993).
Japanese Allowance for App. Ser. No. P2005-515330, issued on Apr. 21, 2009.
Japanese Allowance for App. Ser. No. P2005-516605, issued on Dec. 7, 2010.
Japanese Office Action dated Apr. 11, 2005 for App. Ser. No. 2002-536056 (with English translation).
Japanese Office Action for App. Ser. No. 2007-522356, issued on Feb. 8, 2011.
Japanese Office Action for App. Ser. No. P2005-516605, issued on Nov. 4, 2009.
Japanese Office Action for App. Ser. No. P2005-516605, issued on Jun. 1, 2010.
Japanese Office Action for App. Ser. No. P2008-516724, issued on Oct. 9, 2012 (with English translation).
Jhiang, "The RET proto-oncogene inn human cancers," *Oncogene*, 19:5590-5597 (2000).
Jimenez et al., "Pheochromocytoma and medullary thyroid carcinoma: a new genotype-phenotype correlation of the RET protooncogene 891 germline mutation," *J Clin. Endocrinol. Metab.*, 89:4142-4145 (2004).
Johnson et al., "Paclitaxel plus carboplatin in advanced non-small-cell lung cancer: a phase II trial," *J. Clin. Oncol.*, 14(7):2054-2060 (1996).
Jung et al., "Effects of combination anti-vascular endothelial growth factor receptor and anti-epidermal growth factor receptor therapies on the growth of gastric cancer in a nude mouse model," *Eur. J Cancer*, 38:1133-1140 (2002).
Juurikivi et al., "Inhibition of c-kit tyrosine kinase by imatinib mesylate induces apoptosis in mast cells in rheumatoid synovia: a potential approach to the treatment of arthritis," *Ann Rheum. Dis.*, 64:1126-1131 (2005).
Kanai et al., "Current status and future perspective of molecular targeted therapy for hepatocellular carcinoma," *Journal of the Japanese Society of Gastroenterology*, 106:1727-1735 (2009) (English translation).
Kanakura et al., "Expression, Function and Activation of the Proto-Oncogene c-kit Product in Human Leukemia Cells," *Leukemia and Lymphorma*, 10:35-41 (1993).
Kashuk et al., "Phenotype-genotype correlation in Hirschsprung disease is illuminated by comparative analysis of the RET protein sequence," *PNAS*, 102(25):8949-8954 (2005).
Kawano et al., "Presentation Abstract, Abstract Number; 1619, Combination of VEGFR inhibitor lenvatinib (E7080) and Met/EphB4inhibitor golvatinib (E7050) overcomes VEGFR inhibitor—resistant tumor vascular", Annual Meeting 2013, Walter E. Washington Convention Center, Washington, D.C., Apr. 6-10, 2013, 1 page.
Kay et al., "Eosinophils and Eosinophil-Associated Cytokines in Allergic Inflammation," *Int. Arch. Allergy Immunol.*, 113:196-199 (1997).
Kelly et al., "Randomized phase III trial of paclitaxel plus carboplatin versus vinorelbine plus cisplatin in the treatment of patients with advanced non--small-cell lung cancer: a Southwest Oncology Group trial," *J. Clin. Oncol.*, 19(13):3210-3218 (2001).
Kim et al., "A phase II study of irinotecan plus cisplatin for patients with advanced stage IIIB or IV NSCLC previously treated with nonplatinum-based chemotherapy," *Cancer*, 107(4):799-805 (2006).
Kim et al., "An orally administered multitarget tyrosine kinase inhibitor, SU11248, is a novel potent inhibitor of thyroid oncogenic RET/papillary thyroid cancer kinases," *J. Clin. Endocrinol. Metlab.*, 91(10):4070-4076 (2006).
Kinlaw et al., "Multiple endocrine neoplasia 2A due to a unique C6095 RET mutation presents with pheochromocytoma and reduced penetrance of medullary thyroid carcinoma", Clin Endocrinol, 69, 676-682, 2005.

(56) References Cited

OTHER PUBLICATIONS

Kitamura et al., "Regulation of Development, Survival and Neoplastic Growth of Mast Cells through the c-kit Receptor," *Int. Arch Allergy Immunol.*, 107:54-56 (1995).

Kitteringham et al., "A Simple Method for the Synthesis of Unsymmetrical Ureas," *Synthetic Communications*, 30(11):1937-1943 (2000).

Kleespies et al., "Tyrosine kinase inhibitors and gemcitabine: New treatment options in pancreatic cancer,?" *Drug Resistance Updates*, 9:1-18 (2006).

Ko, "Stomach Cancer," Cancer Supportive Care.com [published online Feb. 2003], [retrieved on Dec. 28, 2011]. Retrieved from the Internet: http://web.archive.org/web/20030224212825/http://www.cancersupportivecare.com/stomach.html.

Kolibaba et al., "Protein Tyrosine Kinases and Cancer," *Biochimica et Biophysica Acta*, 1333:F217-F248 (1997).

Korean Office Action for App. Ser. No. 10-2003-7005506, issued on Jan. 5, 2006 (with English translation).

Korean Office Action for App. Ser. No. 10-2005-7020292, issued on Dec. 8, 2005 (with English translation).

Korean Office Action for App. Ser. No. 10-2006-7013993, issued on Jul. 31, 2007 (with English translation).

Korean Office Action for App. Ser. No. 10-2007-7001347, issued on Sep. 28, 2011 (with English translation).

Korean Office Action for App. Ser. No. 10-2007-7001347, issued on Apr. 27, 2012 (with English translation).

Kotva et al., "Substances with Antineoplastic Activity, LIII. N-(δ-(4-Pyrrolo[2,3-d]Pyrimidinylthio) Valeryl]} Amino Acids and Analogous Derivatives of Di-and Triglycine," *Collection Czechoslov. Chem. Commun.*, 38:1438-1444 (1973).

Koyama et al, "Anti-tumor effect of E7080, a novel angiogenesis inhibitor". *Folia Pharmacol. Jpn.* 132, Therapeutic Agents Series (28), Molecular Target Drugs-1-1, Apr. 18, 2008, pp. 100-104—21 total pages (with English Translation).

Kruckeberg et al., "Pyrosequencing Technology as a Method for the Diagnosis of Multiple Endocrine Neoplasia Type 2", Clinical Chemistry, 50, 522-529, 2004.

Krystal et al., "Indolinone Tyrosine Kinase Inhibitors Block Kit Activation and Growth of Small Cell Lung Cancer Cells", Cancer Research., 61, 3660-3668, 2001.

Kubo et al., "a novel series of 4-phenoxyquinolines: potent and highly selective inhibitors of pdgf receptor autophosphorylation", Bioorganic and Medicinal Chemistry., 48, 1359-1366, 2005.

Kubo et al., "Novel Potent Orally Active Selective VEGFR-2 Tyrosine Kinase Inhibitors: . . . ureas", Journal of Medicinal Chemistry., 48, 1359-1366, 2005.

Laird et al., "SU6668 is a Potent Antiangiogenic and Antitumor Agent That Induces Regression of Established Tumors1", Cancer Research., 60, 4152-4160, 2000.

Lasota et al., "Mutations in Exons 9 and 13 of KIT Gene Are Rare Events in Gastrointestinal Stromal Tumors," *American Journal of Pathology*, 157(4):1091-1095 (2000).

LeDoussal et al. "bispecific-antibody-mediated targeting of radiolabeled bivalent haptens: theoretical, experimental and clinical results", Int. J. Cancer Suppl. 7: 58-62, 1992.

Lee et al., "In vivoTargetModulation and Biological Activity of CHIR-258, aMultitargeted Growth Factor Receptor Kinase Inhibitor, in Colon CancerModels", Clinical Cancer Research., 11, 3633-3641, 2005.

Lesueur et al., "Polymorphisms in RET and its coreceptors and ligands as genetic modifiers of multiple endocrine neoplasia type 2A," *Cancer Res.*, 66:1177-1180 (2006).

Lev et al., "A Specific Combination of Substrates is Involved in Signal Transduction by the Kit-Encoded Receptor," *The EMBO Journal*, 10(3):647-654 (1991).

Li et al., "Abrogation of c-kit/Steel factor-dependent tumorigenesis by kinase defective mutants of the c-kit receptor: c-kit kinase defective mutants as candidate tools for cancer gene therapy," *Cancer Res.*, 56:4343-4346 (1996) (XP002522473).

Lin et al., "The vascular endothelial growth factor receptor tyrosine kinase inhibitor PTK787/ZK222584 inhibits growth and migration of multiple myeloma cells in the bone marrow microenvironment," *Cancer Res.*, 62(17):5019-5026 (2002).

Liu et al., "Structure of Human Methionine Aminopeptidase-2 Complexed with Fumagillin", Science., 282, 1324-1327, 1998.

Logie et al., "Activating mutations of the tyrosine kinase receptor FGFR3 are associated with benign skin tumors in mice and humans," *Human Mol. Genet.*, 14:1153-1160 (2005).

Longley et al., "Altered Metabolism of Mast-Cell Growth Factor (c-kit Ligand) in Cutaneous Mastocytosis," *The New England Journal of Medicine*, 328(18):1302-1307 (1993).

Longley et al., "Classes of c-KIT activating mutations: proposed mechanisms of action and implications for disease classification and therapy," *Leuk. Res.*, 25:571-576 (2001).

Longley et al., "Somatic c-KIT Activating Mutation in Urticaria Pigmentosa and Aggressive Mastocytosis: Establishment of Clonality in a Human Mast Cell Neoplasm," *Nature Genetics*, 12:312-314 (1996).

Lukacs et al., "Stem Cell Factor (c-kit Ligand) Influences Eosinophil Recruitment and Histamine Levels in Allergic Airway Inflammation," *J. Immunol.*, 156:3945-3951 (1996).

M. Behr et al., Improved Treatment of Medullary Thyroid Cancer in a Nude Mouse Model by Combined Radioimmunochemotherapy: Doxorubicin Potentiates the Therapeutic Efficacy of Radiolabeled Antibodies in a Radioresistant Tumor Type, 57 Cancer Res. 5309-5319 (Dec. 1, 1997).

Maintenance of the application for EP App. Ser. No. 01976786.2, dated Sep. 6, 2004.

Maintenance of the application for EP App. Ser. No. 05783232.1, dated Nov. 9, 2007.

Maintenance of the application for EP App. Ser. No. 06023078.6, dated Jun. 19, 2007.

Masferrer et al., "COX-2 Inhibitors a New Class of Antiangiogenic Agents", Annals of N.Y. Acad. Science., 889:84-6, 1999.

Matsui et al., "E7080 (ER-203492-00), a Novel VEGF Receptor )Tyrosine Kinase Inhibitor-I. Characterization as an Angiogenesis Inhibitor," Abstract # 51, *AACR*, Washington, USA (Jul. 11-14 2003).

Matsui et al., "E7080, a novel inhibitor that targets multiple kinases, has potent antitumor activities against stem cell factor producing human small cell lung cancer H146, based on angionenesis inhibition," *Int. J. Cancer*, 122:664-671 (2008).

Matsui et al., "E7080, a novel multi-receptor Tyrosine Kinase Inhibitor, inhibited in vitro / in vivo VEGF- and SCF-driven angiogenesis SCLC cell line," Abstract #146, *EORTC-NCI-AACR*, Geneva, Switzerland (Sep. 28-Oct. 1, 2004).

Matsui et al., "E7080, a novel multi-targeted tyrosine kinase inhibitor, exhibits anti-angiogenic activity via inhibition of KIT signaling in a small cell lung cancer xenograft model," *Eur. J Cancer*, 2(8):47 (2004).

Matsui et al., "Quantitative analysis of the profile of tumor vessels may be useful as predictive biomarkers for E7080," Abstract #4631, *98th AACR annual meeting*, Los Angeles, CA, (Apr. 14-18, 2007).

Matsui et al., "VEGFRs inhibitor E7080 inhibits lymph node metastasis of human breast carcinoma, by preventing murine lymphatic endothelial cells from lymphangiogenesis," Abstract #PD12-8, *18th EORTC-NCI-AACR Symposium on "Molecular Targets and Cancer Therapeutics,"* Prague, Czech Republic (Nov. 7-10, 2006).

McCarty et al., "ZD6474, a vascular endothelial growth factor receptor tyrosine kinase inhibitor with additional activity against epidermal growth factor receptor tyrosine kinase, inhibits orthotopic growth and angiogenesis of gastric cancer," *Mol. Cancer Ther.*, 3(9):1041-1048 (2004).

McCulloch et al., "*Astragalus*-based Chinese herbs and platinum-based chemotherapy for advanced non-small-cell lung cancer: meta-analysis of randomized trials," *J. Clin. Oncol.*, 24(3):419-430 (2006).

Meltzer, "The Pharmacological Basis for the Treatment of Perennial Allergic Rhinitis and Non-Allergic Rhinitis with Topical Corticosteroids," *Allergy*, 52:33-40 (1997).

Memorandum in Response to Office Action dated Apr. 8, 2013 for IL App. Ser. No. 197141, 18 pages (with English translation).

Mendel et al., "In vivo antitumor activity of SU11248, a novel tyrosine kinase inhibitor targeting vascular endothelial growth factor

(56) References Cited

OTHER PUBLICATIONS and platelet-derived growth factor receptors: determination of a pharmacokinetic/pharmacodynamic relationship," *Clin. Cancer Res.*, 9:327-337 (2003).

Metcalfe et al., "Lineage Commitment in the Progeny of Murine Hematopoietic Preprogenitor Cells: Influence of Thrombopoietin and Interleukin 5," *Proc. Nat'l Acad. Sci. USA*, 95:6408-6412 (1998).

Metcalfe et al., "Mast cells," *Physiol. Rev.*, 77(4):1033-1079 (1997).

Metcalfe, "Classification and Diagnosis of Mastocytosis: Current Status," *J. Invest. Dermatol.*, 96:2S-4S (1991).

Micke et al., "Characterization of c-kit expression in small cell lung cancer: prognostic and therapeutic implications," *Clin. Cancer Res.*, 9:188-194 (2003).

Miller et al., "Paclitaxel plus bevacizumab versus paclitaxel alone for metastatic breast cancer," *N. Engl. J. Med.*, 357(26):2666-2676 (2007).

Millstein and Cuello, "Hybrid hybridomas and their use in immunohistochemistry", Nature 305: 537-9, 1983.

Miyazaki et al., "Synthesis, Structure and Biological Activity Relationship of E7080 and its Derivatives as Novel and Potent Antiangiogenic Protein Tyrosine Kinase Inhibitors Including the VEGF Receptors, FGFR1 Receptor and PDGF Receptor," *AIMECS03*, Kyoto, Japan (Oct. 14-17, 2003) (Abstract).

Mohammadi et al., "Crystal structure of an angiogenesis inhibitor bound to the FGF receptor tyrosine kinase domain", EMBO J., 17, 5896-5904, 1998.

Mologni et al., "Inhibition of RET tyrosine kinase by SU5416," J Mol. Endocrinol., 37(2):199-212 (2006).

Morgan et al., "Dynamic contrast-enhanced magnetic resonance imaging as a biomarker for the pharmacological response of PTK787/Zk 222584, an inhibitor of the vascular endothelial growth factor receptor tyrosine kinases, in patients with advanced colorectal cancer and liver metastases: results from two phase I studies," *J. Clin. Oncol.*, 21(21):3955-3964 (2003).

Morikawa et al., "Angiogenesis and Pericytes, " *The Cell*, 37(4):164-168 (2005) (English translation).

Morris et al., "An Integrated Approach to the Selection of optimal Salt Form for a New Drug Candidate," *International Journal of Pharmaceutics*, 105:209-217 (1994) (XP023724810).

Myers et al., "The Preparation and SAR of 4-(Anilino), 4-(Phenoxy), and 4-(Thiophenoxy)-Quinazolines: Inhibitors of p56lck and EGF-R Tyrosine Kinase Activity," *Bioorgan. & Med. Chem. Letters*, 7:417-420 (1997).

Naclerio et al., "Rhinitis and Inhalant Allergens," *JAMA*, 278(22):1842-1848 (1997).

Nagata et al., "Elevated Expression of the Proto-Oncogene c-kit in Patients with Mastocytosis," *Leukemia*, 12:175-181 (1998).

Nakamura et al., "E7080 (ER-203492-00), a Novel VEGF Receptor Tyrosine Kinase Inhibitor-II. Effects on Growth of Human Tumor Xenografts and Life Span of Mice in Colon 38 Orthotopic Transplantation Model," Abstract #52, *AACR*, Toronto, Canada (Apr. 5-9, 2003).

Naruse et al., "Antitumor activity of the selective epidermal growth factor receptor-tyrosine kinase inhibitor (EGFR-TKI Iressa (ZD1839) in an EGFR-expressing multidrug-resistant cell line in vitro and in vivo," *Int. J. Cancer*, 98:310-315 (2002).

Naski et al., "Graded activation of fibroblast growth factor receptor 3 by mutations causing achondroplasia and thanatophoric dysplasia," *Nat. Genet.*, 13:233-237 (1996).

Natali et al., "Breast Cancer is Associated with Loss of the c-kit Oncogene Product," *Int. J. Cancer*, 52:713-717 (1992).

Nocka et al., "Expression of c-kit gene products in known cellular targets of W mutations in normal and W mutant mice—evidence for an impaired c-kit kinase in mutant mice," *Cold Spring Harbor Laboratory Press*, 3:816-826 (1989) (XP002522472).

Non-final Office Action dated May 23, 2013 for U.S. Appl. No. 12/439,339, 15 pages.

Noriyuki et al., "Anti-tumor effect of E7080, a novel angiogenesis inhibitor," Database BIOSIS [Online] Biosciences Information Service, Philadelphia, PA, US: Database accession No. PREV200800475929, Aug. 2008, XP002677323.

Notice of Acceptance dated Aug. 10, 2004 for ZA Patent App. No. 2003/3567.

Notice of Acceptance dated Aug. 3, 2006 for AU App. Ser. No. 2001295986.

Notice of Acceptance dated May 13, 2008 for AU App. Ser. No. 2006236039.

Notice of Acceptance of Complete Specification dated Mar. 4, 2005 for NZ App. Ser. No. 525324.

Notice of Allowability dated Nov. 28, 2007 for PH App. Ser. No. 1-2003-500266.

Notice of Allowance dated Apr. 19, 2005 for RU App. Ser. No. 2003114740 (with English translation).

Notice of Allowance dated Apr. 19, 2011 for JP App. Ser. No. 2007-522356.

Notice of Allowance dated Apr. 24, 2012 for U.S. Appl. No. 12/524,754.

Notice of Allowance dated Apr. 29, 2010 for AU App. Ser. No. 2005283422.

Notice of Allowance dated Aug. 2, 2005 for JP App. Ser. No. 2002-536056 (with English translation).

Notice of Allowance dated Aug. 7, 2012 for Japanese App. Ser. No. P2007-529565 (with English translation).

Notice of Allowance dated Dec. 15, 2006 for CN App. Ser. No. 01819710.8.

Notice of Allowance dated Dec. 26, 2007 for IL App. Ser. No. 155447 (with English translation).

Notice of Allowance dated Feb. 15, 2013 for NZ App. Ser. No. 598291.

Notice of Allowance dated Feb. 27, 2009 for U.S. Appl. No. 11/293,785.

Notice of Allowance dated Feb. 5, 2010 for CN App. Ser. No. 200580026468.7 (with English translation).

Notice of Allowance dated Jul. 17, 2012 for JP App. Ser. No. P2011-527665 (with English translation).

Notice of Allowance dated Jul. 21, 2009 for JP App. Ser. No. 2005-124034 (with English translation).

Notice of Allowance dated Jun. 10, 2013 in U.S. Appl. No. 13/205,328, 58 pages.

Notice of Allowance dated Jun. 13, 2006 for U.S. Appl. No. 10/420,466.

Notice of Allowance dated Jun. 20, 2012 for EP App. Ser. No. 06782407.8.

Notice of Allowance dated Jun. 25, 2012 for EP App. Ser. No. 07806561.2.

Notice of Allowance dated Jun. 3, 2008 for U.S. Appl. No. 11/293,785.

Notice of Allowance dated Jun. 4, 2013 for AU App. Ser. No. 2009210098, 3 pages.

Notice of Allowance dated Jun. 4, 2013 for U.S. Appl. No. 13/083,338, 57 pages.

Notice of Allowance dated Mar. 14, 2010 for IL App. Ser. No. 189677 (with English translation).

Notice of Allowance dated Mar. 16, 2007 for U.S. Appl. No. 10/420,466.

Notice of Allowance dated Mar. 21, 2013 for EP App. Ser. No. 07793075.8, 2 pages.

Notice of Allowance dated Mar. 22, 2012 for U.S. Appl. No. 12/986,638.

Notice of Allowance dated Mar. 8, 2013 for CA App. Ser. No. 2627598.

Notice of Allowance dated May 16, 2013 for EP App. Ser. No. 06796594.7, 2 pages.

Notice of Allowance dated May 18, 2009 for U.S. Appl. No. 11/293,785.

Notice of Allowance dated May 27, 2013 for CN App. Ser. No. 200980103218.7, 4 pages (with English translation).

Notice of Allowance dated May 6, 2013 for EP App. Ser. No. 04818213.3, 22 pages.

Notice of Allowance dated Nov. 14, 2011 for IL App. No. 181697 (with English translation).

(56) References Cited

OTHER PUBLICATIONS

Notice of Allowance dated Nov. 19, 2008 for U.S. Appl. No. 11/293,785.
Notice of Allowance dated Nov. 2, 2012 for EP App. Ser. No. 06782407.8.
Notice of Allowance dated Nov. 2, 2012 for EP App. Ser. No. 07806561.2.
Notice of Allowance dated Oct. 14, 2010 for CA App. Ser. No. 2426461.
Notice of Allowance dated Oct. 17, 2011 for CA App. Ser. No. 2579810.
Notice of Allowance dated Oct. 18, 2006 for MX App. Ser. No. PA/a/2003/003362 (with English translation).
Notice of Allowance dated Oct. 20, 2008 for TW App. Ser. No. 90125928 (with English translation).
Notice of Allowance dated Oct. 31, 2008 for NO App. Ser. No. 20031731 (with English translation).
Notice of Allowance dated Oct. 9, 2010 for CN App. Ser. No. 200710007097.9 (with English translation).
Notice of Allowance dated Oct. 9, 2012 for U.S. Appl. No. 12/524,754.
Notice of Allowance dated Sep. 12, 2005 for U.S. Appl. No. 10/420,466.
Notice of Allowance dated Sep. 20, 2011 for JP App. Ser. No. 2006-535174.
Notice of Allowance dated Sep. 25, 2012 for U.S. Appl. No. 12/986,638.
Notice of Allowance dated Sep. 4, 2012 in JP App. Ser. No. P2009-123432 (with English translation).
Notice of Allowance for JP App. Ser. No. 2008-516724, dated Jan. 22, 2013, 4 pages, with English translation.
Notice of Allowance for U.S. Appl. No. 12/524,754, dated Jan. 18, 2013, 9 pages.
Notice of Allowance for U.S. Appl. No. 12/741,682, dated Feb. 19, 2013, 65 pages.
Notice of Allowance for U.S. Appl. No. 12/524,754 dated Oct. 9, 2012.
Notice of decision for patent dated Apr. 17, 2006 for KR App. Ser. No. 10-2005-7020292, (with English translation).
Notice of decision for patent dated Jun. 12, 2006 for KR App. Ser. No. 10-2003-7005506 (with English translation).
Notice of Rejection dated May 20, 2013 for KR App. Ser. No. 10-2008-7013685, 10 pages (with English translation).
Notice Prior to Examination dated Jun. 29, 2008 for IL App. Ser. No. 189677 (with English translation).
Notice Prior to Examination dated Mar. 9, 2009 for IL App. Ser. No. 181697 (with English translation).
Notification dated Apr. 25, 2008 for PH App. Ser. No. 1-2003-500266.
Notification of Defects dated Apr. 10, 2013 in IL App. Ser. No. 195282, 4 pages.
Notification of Non-Compliant Amendment filed on Jan. 13, 2005 for U.S. Appl. No. 10/420,466.
Nugiel et al., "Synthesis and evaluation of indenopyrazoles as cyclin-dependent kinase inhibitors. 2. Probing the indeno ring substituent pattern," *J. Med. Chem.*, 45(24):5224-5232 (2002).
Nyati et al., "Radiosensitization by Pan ErbB Inhibitor CI-1033 in Vitro and in Vivo", Clinical Cancer Research., 10:691-700, 2004.
Observation dated Apr. 11, 2013 for CN App. Ser. No. 200880115011.7, 10 pages (with English translation).
Observations dated May 27, 2013 for CN App. Ser. No. 201080030508.6, 7 pages (with English translation).
Ocqueteau et al., Expression of the CD117 antigen (C-Kit) on normal and myelomatous plasma cells, *Br. J Haematol.*, 95:489-493 (1996).
Office Action dated Apr. 11, 2013 for IL App. Ser. No. 217197, 4 pages (with English translation).
Office Action dated Apr. 16, 2013 for CA App. Ser. No. 2652442, 2 pages.
Office Action dated Apr. 16, 2013 for EP App. Ser. No. 08846814.5, 5 pages.
Office Action dated Apr. 27, 2010 for CN App. Ser. No. 200710007097.9 (with English translation).
Office Action dated Apr. 28, 2009 for JP App. Ser. No. 2005-124034 (with English translation).
Office Action dated Apr. 8, 2013 for U.S. Appl. No. 11/997,719, 55 pages.
Office Action dated Apr. 9, 2013 for CN App. Ser. No. 201080030508.6 (with English translation).
Office Action dated Aug. 11, 2006 for CN App. Ser. No. 01819710.8 (with English translation).
Office Action dated Aug. 3, 2012 for CN App. Ser. No. 200680020317.5 (with English translation).
Office Action dated Aug. 8, 2003 for PH App. Ser. No. 1-2003-500266.
Office Action dated Dec. 20, 2010 for IL App. Ser. No. 181697 (with English translation).
Office Action dated Dec. 25, 2009 for CN App. Ser. No. 200710007097.9 (with English translation).
Office Action dated Feb. 10, 2006 for CN App. Ser. No. 01819710.8 (with English translation).
Office Action dated Jan. 2, 2013 for IL App. Ser. No. 175363.
Office Action dated Jan. 27, 2009 for JP App. Ser. No. 2005-124034 (with English translation).
Office Action dated Jul. 15, 2011 for CA App. Ser. No. 2579810.
Office Action dated Jul. 21, 2006 for PH App. Ser. No. 1-2003-500266.
Office Action dated Jul. 24, 2009 for CN App. Ser. No. 200710007096.4 (with English translation).
Office Action dated Jul. 27, 2005 for KR App. Ser. No. 10-2003-7005506 (with English translation).
Office Action dated Jun. 26, 2009 for CN App. Ser. No. 200580026468.7 (with English translation).
Office Action dated Jun. 27, 2007 for PH App. Ser. No. 1-2003-500266.
Office Action dated Jun. 5, 2012 for JP App. Ser. No. 2009-123432 (with English translation).
Office Action dated Jun. 7, 2006 for MX App. Ser. No. PA/a/2003/003362 (with English translation).
Office Action dated Mar. 14, 2013 for CN App. Ser. No. 200780017371.9 (with English translation).
Office Action dated Mar. 21, 2007 for PH App. Ser. No. 1-2003-500266.
Office Action dated Mar. 29, 2013 for U.S. Appl. No. 13/624,278, 67 page.
Office Action dated Mar. 6, 2009 for CN App. Ser. No. 200710007097.9 (with English translation).
Office Action dated Mar. 7, 2007 for NO App. Ser. No. 20031731 (with English translation).
Office Action dated May 13, 2005 for CN App. Ser. No. 01819710.8 (with English translation).
Office Action dated May 16, 2008 for NO App. Ser. No. 20031731 (with English translation).
Office Action dated May 3, 2013 for CA App. Ser. No. 2661702, 2 pages.
Office Action dated Nov. 13, 2012 for JP App. Ser. No. P2008-532141 (with English translation).
Office Action dated Nov. 20, 2009 for CN App. Ser. No. 200580026468.7 (with English translation).
Office Action dated Nov. 26, 2007 for MX App. Ser. No. PA/a/2005/013764 (with English translation).
Office Action dated Oct. 11, 2007 for TW App. Ser. No. 90125928 (with English translation).
Office Action dated Oct. 15, 2012 for IL App. Ser. No. 200090 (with English translation).
Office Action dated Oct. 15, 2012 for NZ App. Ser. No. 598291.
Office Action dated Oct. 4, 2005 for MX App. Ser. No. PA/a/2003/003362 (with English translation).
Office Action dated Oct. 4, 2007 for NO App. Ser. No. 20031731 (with English translation).
Office Action dated Sep. 11, 2009 for CN App. Ser. No. 200710007097.9 (with English translation).
Office Action dated Sep. 19, 2012 for CA App. Ser. No. 2627598.

(56) References Cited

OTHER PUBLICATIONS

Office Action dated Sep. 28, 2011 for KR App. Ser. No. 10-2007-7001347 (with English translation).
Office Action dated Sep. 28, 2012 for CN App. Ser. No. 200780017371.9 (with English translation).
Office Action dated Sep. 29, 2012 for CN App. Ser. No. 200980103218.7 (with English translation).
Office Action dated Sep. 5, 2008 for NO App. Ser. No. 20031731 (with English translation).
Office Action dated Sep. 5, 2012 for CN App. Ser. No. 200880003336.6 (with English translation).
Office Action dated Sep. 5, 2012 for CN App. Ser. No. 200880115011.7 (with English translation).
Office Action dated Sep. 7, 2007 for PH App. Ser. No. 1-2003-500266.
Office Action for IL App. Ser. No. 175363, dated Jan. 2, 2013, 2 pages, with English translation.
Office Action for IL App. Ser. No. 205512, dated Dec. 20, 2012, 8 pages, with English translation.
Office Action for IL App. Ser. No. 207089, dated Jan. 6, 2013, 5 pages (with English translation).
Office Action for JP App. Ser. No. 2008-556208, dated Jan. 22, 2013, 8 pages, with English translation.
Office Action for U.S. Appl. No. 13/083,338, dated Jan. 3, 2013, 9 pages.
Office Communication dated Sep. 13, 2004 for U.S. Appl. No. 10/420,466.
Office Letter Confirmation of Amendment After Allowance dated Jan. 11, 2011 for CA App. Ser. No. 2426461.
Office Letter re Notice of Allowance dated May 25, 2012 for ZA App. Ser. No. 201108697.
Official Letter and Notice of Allowance for AU App. Ser. No. 2008211952, dated Jul. 10, 2012.
Official Letter and Notice of Allowance for AU App. Ser. No. 2008325608, dated Feb. 27, 2013, 7 pages.
Official Letter dated Jun. 27, 2013 in CA App. Ser. No. 2661333, 2 pages.
Official Letter re Grant of Request for Correction of Specification for SG App. Ser. No. 201108602-2, dated Aug. 8, 2012.
Ohe et al., "Randomized phase III study of cisplatin plus irinotecan versus carboplatin plus paclitaxel, cisplatin plus gemcitabine, and cisplatin plus vinorelbine for advanced non-small-cell lung cancer: Four-Arm Cooperative Study in Japan," *Ann Oncol.*, 18(2):317-323 (2007).
Okayama et al., "Activation of Eosinophils with Cytokines Produced by Lung Mast Cells," *Int Arch Allergy Immunol.*, 114(suppl 1):75-77 (1997).
Okayama et al., "Human Lung Mast Cells are Enriched in the Capacity to Produce Granulocyte-Macrophage Colony-Stimulating Factor in Response to IgE-Dependent Stimulation," *Eur. J. Immunol.*, 28:708-715 (1998).
Okura et al., "Effects of monoclonal anti-c-kit antibody (ACK2) on melanocytes in newborn mice," *J. Invest. Dermatol.*, 105(3):322-328 (1995).
Olaso et al., "DDR2 receptor promotes MMP-2-mediated proliferation and invasion by hepatic stellate cells," *J. Clin. Invest.*, 108(9):1369-1378 (2001).
Ozols et al., "Phase III trial of carboplatin and paclitaxel compared with cisplatin and paclitaxel in patients with optimally resected stage III ovarian cancer: a Gynecologic Oncology Group study," *J. Clin. Oncol.*, 21(17):3194-3200 (2003).
Pakistani Office Action for App. Ser. No. 94/2011, issued on May 9, 2012.
Pandey et al., "Identification of Orally Active, Potent, and Selective 4-Piperazinylquinazolines as Antagonists of the Platelet-Derived Growth Factor Receptor Tyrosine Kinase Family", *Journal of Medicinal Chemistry.*, 45, 3772-3793, 2002.
Partial European Search Report for App. Ser. No. 01976786.2, dated Apr. 6, 2004.
Paterson et al., "Preclinical studies of fibroblast growth factor receptor 3 as a therapeutic target in multiple myeloma," *British Journal of Haematology*, 124:595-603 (2004).
Paz et al., "Development of angiogenesis inhibitors to vascular endothelial growth factor receptor 2. Current status and future perspective," *Frontiers in Bioscience*, 10:1415-1439 (May 1, 2005).
PCT/JP2006/322514 International Preliminary Report on Patentability issued on May 7, 2008.
PCT/JP2006/322516 International Preliminary Report on Patentability issued on May 7, 2008.
PCT/JP2006/322516 International Search Report issued on Jan. 23, 2007.
Petti et al., "Temporal quantitation of mutant Kit tyrosine kinase signaling attenuated by a novel thiophene kinase inhibitor OSI-930", Molecular Cancer Therapeutics., 4:1186-1197, 2005.
Plowright et al., "Ectopic expression of fibroblast growth factor receptor 3 promotes myeloma cell proliferation and prevents apoptosis," *Blood*, 95:992-998 (2000).
Podar et al., "GW654652, the pan-inhibitor of VEGF receptors, blocks the growth and migration of multiple myeloma cells in the bone marrow microenvironment", *Blood.*,103, 3474-3479, 2004.
Polverino et al, "AMG 706, an Oral, Multikinase Inhibitor that Selectively Targets Vascular Endothelial Growth Factor, Platelet - Derived Growth Factor, and Kit Receptors, Potently inhibits Angiogenesis and Induces Regression in Tumor Xenografts," Cancer Research, 66(17):8715-8721 (2006).
Preliminary Amendment and Response to Restriction Requirement in U.S. Appl. No. 12/439,339, filed on Aug. 10, 2011.
Preliminary Amendment and Response to Restriction Requirement in U.S. Appl. No. 13/083,338, filed on Apr. 30, 2012.
Preliminary Amendment dated Apr. 26, 2013 for U.S. Appl. No. 13/870,507, 10 pages.
Preliminary Amendment filed on Apr. 18, 2003 for U.S. Appl. No. 10/420,466.
Preliminary Amendment filed on Dec. 2, 2005 for U.S. Appl. No. 11/293,785.
Preliminary Amendment filed on Feb. 3, 2006 for U.S. Appl. No. 11/293,785.
Preliminary Amendment filed on May 23, 2003 for KR App. Ser. No. 10-2003-7005506 (with English translation).
Preliminary Amendment filed on Oct. 27, 2003 for U.S. Appl. No. 10/420,517.
Pritzker, "Cancer Biomarkers: Easier Said Than Done," *Clinical Chemistry*, 48(8):1147-1150 (2002).
Reasons for Reexamination dated Sep. 11, 2012 for CN App. Ser. No. 200680020317.5 (with English translation).
Reexamination filed on Nov. 25, 2004 for TW App. Ser. No. 90125928 (with English translation).
Registered dated Feb. 24, 2009 for PH App. Ser. No. 1-2003-500266.
Rejection dated Apr. 26, 2004 for TW App. Ser. No. 90125928 (with English translation).
Reply to communication from the Examining Division for EP App. Ser. No. 01976786.2, dated Jan. 25, 2006.
Reply to communication from the Examining Division for EP App. Ser. No. 01976786.2, dated Jul. 19, 2006.
Reply to communication from the Examining Division for EP App. Ser. No. 04025700.8, dated Sep. 12, 2006.
Reply to communication from the Examining Division for EP App. Ser. No. 04025700.8, dated Jan. 26, 2007.
Reply to communication from the Examining Division for EP App. Ser. No. 04025700.8, dated Feb. 15, 2007.
Reply to communication from the Examining Division for EP App. Ser. 06023078.6, dated Sep. 11, 2007.
Reply to communication from the Examining Division for EP App. Ser. 06023078.6, dated Feb. 4, 2008.
Reply to Examination Report dated Feb. 8, 2013 for EP App. Ser. No. 07743994.1, 4 pages.
Reply to official communication for EP App. Ser. No. 05783232.1, dated Apr. 30, 2008.
Reply to the invitation to remedy deficiencies for EP App. Ser. No. 06023078.6, dated Jan. 11, 2007.
Request for amendment of the text intended for grant and translation of claims for EP App. Ser. No. 04025700.8, dated Feb. 1, 2008.

(56) References Cited

OTHER PUBLICATIONS

Request for amendment of the text intended for grant and translation of claims for EP App. Ser. No. 06023078.6, dated Nov. 5, 2008.
Request for Continued Examination (RCE) transmittal for U.S. Appl. No. 12/864,817, filed on Dec. 22, 2011.
Request for Continued Examination and Information Disclosure Statement dated Apr. 15, 2013 for U.S. Appl. No. 12/254,754, 17 pages.
Request for Continued Examination and Information Disclosure Statement dated May 17, 2013 for U.S. Appl. No. 12/741,682, 16 pages.
Request for correction of errors in filed documents for EP App. Ser. No. 06023078.6, dated Feb. 13, 2007.
Request for Substantive Examination dated Apr. 15, 2013 for UA App. Ser. No. a201203132, 14 pages (with English translation).
Request for Substantive Examination dated Jun. 3, 2013 for ID App. Ser. No. W-00201201031, 6 pages (with English translation).
Request to Amend Complete Specification dated Feb. 15, 2013 for AU App. Ser. No. 2008325608, 23 pages.
Request to Amend Complete Specification dated May 9, 2013 for AU App. Ser. No. 2009210098, 22 pages.
Response filed on Apr. 11, 2006 for CN App. Ser. No. 01819710.8 (with English translation).
Response filed on Apr. 17, 2007 for PH App. Ser. No. 1-2003-500266.
Response filed on Apr. 27, 2006 for AU App. Ser. No. 2001295986.
Response filed on Apr. 30, 2008 for PH App. Ser. No. 1-2003-500266.
Response filed on Aug. 13, 2009 for CA App. Ser. No. 2426461.
Response filed on Aug. 14, 2006 for PH App. Ser. No. 1-2003-500266.
Response filed on Aug. 18, 2008 for NO App. Ser. No. 20031731 (with English translation).
Response filed on Aug. 21, 2006 for MX App. Ser. No. PA/a/2003/003362 (with English translation).
Response filed on Aug. 26, 2004 for NZ App. Ser. No. 525324.
Response filed on Aug. 5, 2003 for PH App. Ser. No. 1-2003-500266.
Response filed on Dec. 11, 2007 for TW App. Ser. No. 90125928 (with English translation).
Response filed on Dec. 15, 2005 for MX App. Ser. No. PA/a/2003/003362 (with English translation).
Response filed on Dec. 4, 2007 for IL App. Ser. No. 155447 (with English translation).
Response filed on Feb. 23, 2009 for CA App. Ser. No. 2426461.
Response filed on Feb. 26, 2008 for U.S. Appl. No. 11/293,785.
Response filed on Jan. 11, 2010 for CN App. Ser. No. 200580026468.7 (with English translation).
Response filed on Jan. 21, 2005 for NZ App. Ser. No. 525324.
Response filed on Jan. 26, 2010 for CN App. Ser. No. 200710007097.9 (with English translation).
Response filed on Jan. 26, 2011 for IL App. Ser. No. 181697 (with English translation).
Response filed on Jul. 1, 2005 for U.S. Appl. No. 10/420,466.
Response filed on Jul. 2, 2009 for CN App. Ser. No. 200710007097.9 (with English translation).
Response filed on Jul. 26, 2006 for AU App. Ser. No. 2001295986.
Response filed on Jul. 31, 2007 for PH App. Ser. No. 1-2003-500266.
Response filed on Jun. 22, 2010 for CN App. Ser. No. 200710007097.9 (with English translation).
Response filed on Mar. 17, 2005 for RU App. Ser. No. 2003114740 (with English translation).
Response filed on May 13, 2009 for IL App. Ser. No. 189677 (with English translation).
Response filed on May 16, 2008 for CA App. Ser. No. 2426461.
Response filed on May 20, 2010 for CA App. Ser. No. 2426461.
Response filed on May 7, 2008 for NO App. Ser. No. 20031731 (with English translation).
Response filed on May 8, 2008 for AU App. Ser. No. 2006236039.
Response filed on Nov. 19, 2009 for CN App. Ser. No. 200710007097.9 (with English translation).
Response filed on Nov. 30, 2004 for RU App. Ser. No. 2003114740 (with English translation).
Response filed on Oct. 13, 2008 for NO App. Ser. No. 20031731 (with English translation).
Response filed on Oct. 15, 2007 for PH App. Ser. No. 1-2003-500266.
Response filed on Oct. 8, 2004 for U.S. Appl. No. 10/420,466.
Response filed on Oct. 9, 2006 for CN App. Ser. No. 01819710.8 (with English translation).
Response filed on Sep. 10, 2007 for NO App. Ser. No. 20031731 (with English translation).
Response filed on Sep. 13, 2005 for CN App. Ser. No. 01819710.8 (with English translation).
Response filed on Sep. 15, 2003 for PH App. Ser. No. 1-2003-500266.
Response filed on Sep. 21, 2011 for CA App. Ser. No. 2579810.
Response filed on Sep. 23, 2009 for CN App. Ser. No. 200580026468.7 (with English translation).
Response filed on Sep. 8, 2003 for PH App. Ser. No. 1-2003-500266.
Response to Notice of Allowability filed on Dec. 13, 2007 for PH App. Ser. No. 1-2003-500266.
Response to Notice Prior to Examination filed on Apr. 22, 2009 for IL App. Ser. No. 181697 (with English translation).
Response to Notice Prior to Examination filed on Jan. 11, 2009 for IL App. Ser. No. 189677 (with English translation).
Response to Office Action dated Feb. 7, 2013 for CN App. Ser. No. 201080030508.6, 17 pages (with English translation).
Response to Office Action dated Jul. 5, 2012 for CN App. Ser. No. 200880115011.7 (with English translation).
Response to Office Action dated Nov. 30, 2012 for CN App. Ser. No. 200780017371.9, 4 pages (with English translation).
Response to Office Action filed on Jan. 25, 2013 for CA App. Ser. No. 2627598, 9 pages.
Response to Office Action filed on Jul. 11, 2012 for CN App. Ser. No. 200880003336.6 (with English translation).
Response to Office Action filed on May 29, 2012 for RU App. Ser. No. 2012103471 (with English translation).
Response to Office Action for Australian App. Ser. No. 2006309551, filed on Mar. 28, 2012.
Response to Office Action for CN200880115011.7 dated Nov. 20, 2012 with English translation.
Response to Office Action for Israeli App. Ser. No. 205512, filed on Mar. 11, 2012 (with English translation).
Response to Office Action for Israeli App. Ser. No. 207089, filed on Mar. 11, 2012, with English translation.
Response to Office Action for U.S. Appl. No. 13/322,961, dated Jan. 25, 2013, 22 pages.
Response to Office Action under 37 C.F.R. §1.111 for U.S. Appl. No. 12/523,495, filed on Dec. 7, 2011.
Response to Office Action under 37 C.F.R. §1.111 for U.S. Appl. No. 13/083,338, filed on Sep. 6, 2012.
Response to Restriction Requirement for U.S. Appl. No. 11/997,543, filed on Mar. 22, 2011.
Response to Restriction Requirement for U.S. Appl. No. 12/301,353, filed on Nov. 23, 2010.
Response to Restriction Requirement for U.S. Appl. No. 12/524,754, filed on Dec. 1, 2011.
Response to the European Search Report for European Application No. 06782407 filed on Nov. 8, 2010.
Restriction Requirement for U.S. Appl. No. 11/997,543, dated Feb. 23, 2011.
Restriction Requirement for U.S. Appl. No. 12/092,539, dated Oct. 29, 2010.
Restriction Requirement for U.S. Appl. No. 12/301,353, dated Oct. 29, 2010.
Restriction Requirement for U.S. Appl. No. 12/439,339, dated Jul. 29, 2011.
Restriction Requirement for U.S. Appl. No. 12/524,754, dated Nov. 3, 2011.
Roberts et al., "Antiangiogenic and Antitumor Activity of a Selective PDGFR Tyrosine Kinase Inhibitor, CP-673,451", Cancer Research., 65, 957-966, 2005.
Ruggeri et al., "CEP-7055: A Novel, Orally Active Pan Inhibitor of Vascular Endothelial Growth Factor Receptor Tyrosine Kinases with Potent Antiangiogenic Activity and Antitumor Efficacy in Preclinical Modelsl", Cancer Research., 63, 5978-5991, 2003.

(56) References Cited

OTHER PUBLICATIONS

Russian Office Action dated Apr. 11, 2012 for App. Ser. No. 2012103471, (with English translation).
Russian Office Action dated Jan. 19, 2005 for App. Ser. No. 2003114740 (with English translation).
Russian Office Action dated Jun. 29, 2004 for App. Ser. No. 2003114740 (with English translation).
Salmon et al., "Anti-angiogenic treatment of gastrointestinal malignancies," *Cancer Invest.*, 23(8):712-726 (2005).
Sandler et al., "Phase III trial of gemcitabine plus cisplatin versus cisplatin alone in patients with locally advanced or metastatic non-small-cell lung cancer," *J. Clin. Oncol.*, 18(1):122-130 (2000).
Santoro et al., "Drug insight: Small-molecule inhibitors of protein kinases in the treatment of thyroid cancer," *Nat. Clin. Pract. Endocrinol. Metab.*, 2(1):42-52 (2006).
Santoro et al., "Minireview: RET: normal and abnormal functions," *Endocrinology*, 145:5448-5451 (2004).
Santoro et al., "Molecular Mechanisms of RET Activation in Human Cancer," *Ann. N.Y. Academy of Sciences*, 963:116-121 (2002).
Scheijen et al., "Tryosine Kinase Oncogenes in Normal Hematopoiesis and Hematological Disease," *Oncogene*, 21:3314-3333 (2002).
Schlumberger et al., "A Phase 2 Trial of the Multi-Targeted Kinase Inhibitor Lenvatinib (E7080) in Advanced Medullary Thyroid Cancer (MTC)," 2012 ASCO Annual Meeting, Poster Presentation, Jun. 1-5, 2012.
Second Preliminary Amendment and Response to Restriction Requirement for U.S. Appl. No. 12/092,539, filed on Nov. 22, 2010.
Sekido et al., "Preferential Expression of c-kit Protooncogene Transcripts in Small Cell Lung Cancer," *Cancer Res.*, 51:2416-2418 (1991).
Shiang et al., "Mutations in the transmembrane domain of FGFR3 cause the most common genetic form of dwarfism, achondroplasia," *Cell.*, 78:335-342 (1994).
Shibata et al., "Rapid Communication Association of Epstein-Barr Virus with Undifferentiated Gastric Carcinomas with Intense Lymphoid Infiltration", American Journal of Pahthology 139(3):469-473 (1991).
Shimizu et al., "Orally active anti-proliferation agents: novel diphenylamine derivatives as FGF-R2 autophosphorylation inhibitors," *Bioorganic and Medicinal Chemistry Letters*, 14(4):875-879 (2004).
Siegel et al., "Sorafenib: Where Do We Go from Here?," *Hepatology*, 52:360-369 (2010).
Sihto et al., "KIT and platelet-derived growth factor receptor alpha tyrosine kinase gene mutations and KIT amplifications in human solid tumors," Journal of Clinical Oncology, 23(1):49-57 (2005).
Spacey et al., "Indolocarbazoles, Potent and Selective Inhibitors of Platelet-Derived Growth Factor Receptor Autophosphorylation," *Biochemical Pharmacology*, 55:261-271 (1998).
Strohmeyer et al., "Expression of the hst-1 and c-kit Protoonocogenes in Human Testicular Germ Cell Tumors," *Cancer Res.*, 51:1811-1816 (1991).
Submission Document(s) Before the Patent Office for IL App. Ser. No. 200090, dated Dec. 23, 2012, 16 pages, with English translation.
Submission Document Before the Patent Office dated Apr. 22, 2013 for IL App. Ser. No. 207089, 7 pages (with English translation).
Submission Document Before the Patent Office dated Mar. 14, 2013 for IL App. Ser. No. 205512, 12 pages (with English translation).
Submission Document Before the Patent Office for EP App. Ser. No. 8704376.6, dated Jan. 2, 2013, 22 pages.
Submission Document Before the Patent Office for EP App. Ser. No. 08846814.5, dated Jan. 3, 2013, 102 pages.
Submission Document Before the Patent Office for EP App. Ser. No. 03791389.4, dated Dec. 20, 2012, 4 pages.
Submission Document Before the Patent Office re Observation dated Feb. 16, 2013 for CN App. Ser. No. 200980103218.7, 8 pages (with English translation).
Submission Documents Before the Patent Office for KR App. Ser. No. 10-2009-7017694, dated Jan. 18, 2013, 22 pages, with English translation.
Submission of Amendments and Complete Specification dated Apr. 10, 2013 for IN App. Ser. No. 1571/CHENP/2007, 15 pages.
Submission of Document Before the Patent Office re Request for Voluntary Amendments dated Jan. 30, 2013 for NZ App. Ser. No. 598291, 8 pages.
Submission of Document re Claims filed in Response to Second Office Action for CN App. Ser. No. 200880115011.7, filed on Nov. 20, 2012.
Submission of Document re Request for Examination in CO App. Ser. No. 12-022608, submitted on Jun. 12, 2012.
Submission of Documents Before the Patent Office for IL App. Ser. No. 175363, dated Feb. 27, 2013, 22 pages.
Submission of Documents re Amendment in UA App. Ser. No. a2012 03132, submitted on May 22, 2012.
Submission of Documents re Claim 3 and Figure 3 for KR App. Ser. No. 10-2009-7005657, filed on Jul. 13, 2012.
Sun et al., "Design, synthesis, and evaluations of substituted 3-[(3-or 4-carboxyethylpyrrol-2- yl)methylidenyl]indolin-2-ones as inhibitors of VEGF, FGF, and PDGF receptor tyrosine kinases", Journal of Medicinal Chemistry., 42:5120-5130 (1999).
Sun et al., "Discovery of 5-[5-Fluoro-2-oxo-1,2-dihydroindol-(3Z)-ylidenemethyl]-2,4-dimethyl-1H-pyrrole-3carboxylic acid . . . Tyrosine Kinase", Journal of Medicinal Chemistry., 46:1116-1119.
Sun et al., "Synthesis and Biological Evaluations of 3-Substituted Indolin-2-ones: A novel class of Tyrosine kinase inhibitors that exhibit selectivity toward particular receptor tyrosine kinases", Journal of Medicinal Chemistry., 41:2588-2603 (1998).
Supplementary European Search Report for App. Ser. No. 01976786.2, dated Jul. 6, 2004.
Supplementary European Search Report for App. Ser. No. 08 70 4376, dated Jun. 14, 2012.
Supplementary European Search Report for App. Ser. No. 08846814.5, issued on Jun. 18, 2012.
Supplementary Observation dated Mar. 13, 2013 for CN App. Ser. No. 200980103218.7, 6 pages (with English translation).
Taguchi et al., "A novel orally active inhibitor of VEGF receptor tyrosine kinases KRN951: Anti-angiogenic and anti-tumor activity against human solid tumors," *Proceedings of the AACR Annual Meeting*, 45:595 (Mar. 2004) (XP002536608).
Takahashi et al., "A case of inoperable scirrhous gastric cancer that responded remarkably to a combination of TS-1+paclitaxel and showed complete loss of ascites," *Japanese Journal of Cancer and Chemotherapy*, 31(7):1093-1095 (2004).
Takeda et al., "AZD2171 shows potent anti-tumor activity against gastric cancer expressing variant K-SAM/FGFR2," Abstract #3785, *Proceeding of the American Association for Cancer Research*, 47:890 (2006).
Tan et al., "Randomized study of vinorelbine—gemcitabine versus vinorelbine—carboplatin in patients with advanced non-small cell lung cancer," *Lung Cancer*, 49(2):233-240 (2005).
Taniguchi et al., "Effect of c-kit Mutation on Prognosis of Gastrointestinal Stromal Tumors," *Cancer Res.*, 59:4297-4300 (1999).
The Pharmacology of Monoclonal Antibody, vol. 113, Chapter 11, Rosenburg and Moore ed., Springer Verlag (1994) pp. 269-315.
Third Office Action dated Feb. 25, 2013 for CN App. Ser. No. 200880115011.7, 6 pages (with English translation).
Thomas et al., "The Eosinophil and its Role in Asthma," *Gen. Pharmac.*, 27(4)593-597 (1996).
Thyroid Cancers, Endocrine and Metabolic Disorders, http://www.merkmanuals.com/professional/print/sec12/ch152/ch152j.html Mar. 16, 2011.
Tian et al., "Activating c-kit Gene Mutations in Human Germ Cell Tumors," *American Journal of Pathology*, 154(6):1643-1647 (1999).
Tohyama et al., "P-3111, Preclinical effect of lenvatinib on human thyroid cancer targeting angiogenesis and receptor tyrosine kinase signaling," The 71st Annual Meeting of the Japanese Cancer Association, Sep. 19-21, 2012, p. 502.
Tonary et al., "Lack of expression of c-KIT in ovarian cancers is associated with poor prognosis," *Int. J. Cancer*, 89:242-250 (2000).

(56) References Cited

OTHER PUBLICATIONS

Tong et al., "Vascular normalization by vascular endothelial growth factor receptor 2 blockade induces a pressure gradient across the vasculature and improves drug penetration in tumors," *Cancer Res.*, 64:3731-3736 (2004).
Toshiyuki et al., "Thermal recording materials with improved background stability," Database CA (Online) Chemical Abstracts Service, Columbus, OH, US (Feb. 20, 1996) (XP002443195).
Transmittal of Information Disclosure Statement, Terminal Disclaimer, Request for Continued Examination, and Response to Office Action under 37 C.F.R. §1.116 for U.S. Appl. No. 11/997,719, filed on Jul. 6, 2011.
Traxler et al., "AEE788; a dual family epidermal growth factor receptor/ErbB2 and vascular endothelial growth factor receptor tyrosine kinase inhibitor with antitumor and antiangiogenic activity," *Cancer Res.*, 64:4931-4941 (2004).
Trudel et al., "CHIR-258, a novel, multitargeted tyrosine kinase inhibitor for the potential treatment of t(4;14) multiple myeloma," *Blood*, 105:2941-2948 (2005).
Trudel et al., "Inhibition of fibroblast growth factor receptor 3 induces differentiation and apoptosis in t(4;14) myeloma," *Blood*, 103:3521-3528 (2004).
Tsou et al., "Optimization of 6,7-Disubstituted-4-(arylamino)quinoline-3-carbonitriles as Orally Active, Irreversible Inhibitors of Human Epidermal Growth Factor Receptor-2 Kinase Activity", Journal of Medicinal Chemistry., 48, 1107-1131, 2005.
U.S. Office Action for U.S. Appl. No. 10/420,466, issued on Apr. 13, 2005.
U.S. Office Action for U.S. Appl. No. 10/577,531, issued on Sep. 23, 2008.
U.S. Office Action for U.S. Appl. No. 10/797,903, issued on Apr. 1, 2010.
U.S. Office Action for U.S. Appl. No. 10/797,903, issued on Aug. 20, 2009.
U.S. Office Action for U.S. Appl. No. 10/797,903, issued on Dec. 11, 2007.
U.S. Office Action for U.S. Appl. No. 11/293,785, issued on Sep. 4, 2007.
U.S. Office Action for U.S. Appl. No. 11/347,749, issued on Feb. 9, 2009.
U.S. Office Action for U.S. Appl. No. 11/662,425, issued on May 3, 2010.
U.S. Office Action for U.S. Appl. No. 11/662,425, issued on Sep. 28, 2010.
U.S. Office Action for U.S. Appl. No. 11/997,543, issued on Feb. 23, 2011.
U.S. Office Action for U.S. Appl. No. 11/997,543, issued on May 19, 2011.
U.S. Office Action for U.S. Appl. No. 11/997,543, issued on Nov. 9, 2011.
U.S. Office Action for U.S. Appl. No. 11/997,719, issued on Apr. 6, 2011.
U.S. Office Action for U.S. Appl. No. 11/997,719, issued on Sep. 3, 2010.
U.S. Office Action for U.S. Appl. No. 12/092,539, issued on Jan. 7, 2011.
U.S. Office Action for U.S. Appl. No. 12/092,539, issued on Jun. 28, 2011.
U.S. Office Action for U.S. Appl. No. 12/092,539, issued on May 9, 2011.
U.S. Office Action for U.S. Appl. No. 12/094,492, issued on Mar. 24, 2011.
U.S. Office Action for U.S. Appl. No. 12/301,353, issued on Jan. 24, 2011.
U.S. Office Action for U.S. Appl. No. 12/400,562, issued on Mar. 31, 2010.
U.S. Office Action for U.S. Appl. No. 12/439,339, issued on Mar. 30, 2012.
U.S. Office Action for U.S. Appl. No. 12/439,339, issued on Nov. 14, 2011.
U.S. Office Action for U.S. Appl. No. 12/523,495, issued on Dec. 27, 2011.
U.S. Office Action for U.S. Appl. No. 12/523,495, issued on Sep. 27, 2011.
U.S. Office Action for U.S. Appl. No. 12/524,754, issued on Dec. 19, 2011.
U.S. Office Action for U.S. Appl. No. 12/741,682, issued on Apr. 30, 2012.
U.S. Office Action for U.S. Appl. No. 12/864,817, issued on Dec. 16, 2011.
U.S. Office Action for U.S. Appl. No. 12/864,817, issued on May 19, 2011.
U.S. Office Action for U.S. Appl. No. 12/864,817, issued on Nov. 3, 2011.
U.S. Office Action for U.S. Appl. No. 13/083,338, issued on Apr. 12, 2012.
U.S. Office Action for U.S. Appl. No. 13/083,338, issued on Jun. 8, 2012.
U.S. Office Action for U.S. Appl. No. 13/083,338, issued on Nov. 23, 2012.
U.S. Office Action for U.S. Appl. No. 13/205,328, issued on Jan. 12, 2012.
U.S. Office Action for U.S. Appl. No. 13/205,328, issued on May 1, 2012.
U.S. Office Action for U.S. Appl. No. 13/322,961, issued on Sep. 25, 2012.
Ueda et al., "VGA1155, a Novel Binding Antagonist of VEGF, Inhibits Angiogenesis in Vitro and in Vivo", Anticancer Research., 24, 3009-3017, 2004.
Ueda et al., "Deletion of the carboxyl-terminal exons of K-sam/FGFR2 by short homology-mediated recombination, generating preferential expression of specific messenger RNAs," *Cancer Res.*, 59(24):6080-6086 (1999).
Van Dijk et al. "Induction of Tumor-Cell Lysis by B-Specific Monoclonal Antibodies Recognizing Renal-Cell Carcinoma and CD3 Antigen", Int. J. Cancer 43: 344-9, 1989.
van Oers et al., "A simple and fast method for the simultaneous detection of nine fibroblast growth factor receptor 3 mutations in bladder cancer and voided urine," *Clin. Cancer Res.*, 11:7743-7748 (2005).
Vippagunta et al., "Crystalline solids," *Advanced Drug Delivery Reviews*, 48:3-26 (2001).
Vogel et al., "Sensing extracellular matrix: an update on discoidin domain receptor function," *Cell Signaling*, 18:1108-1116 (2006).
Voluntary Amendment filed on Aug. 11, 2010 for CN App. Ser. No. 200710007097.9 (with English translation).
Voluntary Amendment filed on Aug. 19, 2010 for CS App. Ser. No. 2426461.
Voluntary Amendment filed on Aug. 30, 2006 for AU App. Ser. No. 2006203099.
Voluntary Amendment filed on Feb. 16, 2012 for BR Patent App. No. BR112012003592-4 (with partial English translation).
Voluntary Amendment filed on Feb. 21, 2007 for AU App. Ser. No. 2006203099.
Voluntary Amendment filed on Feb. 27, 2007 for AU App. Ser. No. 2006236039.
Voluntary Amendment filed on Feb. 9, 2010 for AU App. Ser. No. 2005283422.
Voluntary Amendment filed on Jul. 6, 2010 for AU App. Ser. No. 2005283422.
Voluntary Amendment filed on Sep. 10, 2010 for HU App. Ser. No. P0302603 (with English translation).
Voluntary Amendment for Australian App. Ser. No. 2010285740, filed on Nov. 21, 2011.
Voluntary Amendment for Chinese counterpart of App. No. PCT/JP2010/063804, filed on Jan. 5, 2012 (with English translation).
Voluntary Amendment for Russian App. Ser. No. 2012103471, filed on Feb. 1, 2012 (with English translation).
Voluntary Amendment for Thailand App. Ser. No. 1201000221, filed on Feb. 17, 2012.
Voluntary Brief Amendments for Venezuelan App. Ser. No. 2011-000193, filed on Dec. 21, 2011 (with English translation).

(56) References Cited

OTHER PUBLICATIONS

Wakeling et al., "ZD1839 (Iressa): an orally active inhibitor of epidermal growth factor signaling with potential for cancer therapy," *Cancer Res.*, 62(20)5749-5754 (2002).
Wakui, "Chemotherapy of scirrhous gastric cancer," *Japanese Journal of Cancer and Chemotherapy*, 21(14):2398-2406 (1994) (English abstract).
Wang et al., "A Convenient Set of Bidentate Pyridine Ligands for Combinatorial Synthesis," *Tetrahedron Lett.*, 40:4779-1478 (1999).
Wang et al., "Phase II study of gemcitabine and carboplatin in patients with advanced non-small-cell lung cancer," *Cancer Chemother Pharmacol.*, 60(4):601-607 (2007).
Wang et al., "The Expression of the Proto-Oncogene C-Kit in the Blast Cells of Acute Myeloblastic Leukemia," *Leukemia*, 3(10):699-702 (1989).
Wedge et al., "ZD4190: An Orally Active Inhibitor of Vascular Endothelial Growth Factor Signaling with Broad-Spectrum Antitumor Efficacy", *Cancer Research.*, 60, 970-975, 2000.
Wedge et al., "AZD2171: a highly potent, orally bioavailable, vascular endothelial growth factor receptor-2 tyrosine kinase inhibitor for the treatment of cancer," *Cancer Res.*, 65(10):4389-4400 (2005).
Werner et al., "Gastric adenocarcinoma: pathomorphology and molecular pathology," *J. Cancer Res. Clin. Oncology*, 127:207-216 (2001) (English abstract).
Wilhelm et al., "BAY 43/9006 Exhibits Broad Spectrum Oral Antitumor Activity and Targets the RAF/MEK/ERK Pathway and Receptor Tyrosine Kinases Involved in Tumor Progression and Angiogenesis", *Cancer Research.*, 64:7099-7109 (2004).
Willett et al., "Direct evidence that the VEGF-specific antibody bevacizumab has antivascular effects in human rectal cancer," *Nat. Med.*, 10(2):145-1147 (2004).
Wisniewski et al.,"Characterization of Potent Inhibitors of the Bcr-Abl and the c-Kit Receptor Tyrosine Kinases", *Cancer Research.*, 62, 4244-4255, 2002.
Wood et al., "A Unique Structure for Epidermal Growth Factor Receptor Bound to GW572016 (Lapatinib): Relationships among Protein Conformation, Inhibitor Off-Rate, and Receptor Activity in Tumor Cells", *Cancer Research.*, 64, 6652-6659. 2004.
Wood et al., "PTK787/Zk 222584, a Novel and Potent Inhibitor of Vascular Endothelial Growth Factor Receptor Tyrosine Kinases, Impairs Vascular Endothelial Growth Factor-Induced Responses and Tumor Growth after Oral Administration", *Cancer Research.*, 60, 2178-2189, 2000.
Wozniak et al., "Randomized trial comparing cisplatin with cisplatin plus vinorelbine in the treatment of advanced non-small-cell lung cancer: a Southwest Oncology Group study," *J. Clin. Oncol.*, 16(7):2459-2465 (1998).
Written Amendment filed on Jun. 16, 2009 for JP App. Ser. No. 2009-123432 (with English translation).
Written Amendment filed on Sep. 21, 2011 for JP App. Ser. No. 2011-527665 (with English translation).
Written Statement filed on Jun. 16, 2009 for JP App. Ser. No. 2009-123432 (with English translation).
Written Statement filed on Sep. 21, 2011 for JP App. Ser. No. 2011-527665 (with English translation).
Wulff et al., "Luteal Angiogenesis: Prevention and Intervention by Treatment with Vascular Endothelial Growth Factor TrapA40", The Journal of Clinical Endocrinology & Metabolism. 86(7), 3377-3386, 2001.
Yamada et al., "New technique for staining," *Monthly Medical Technology Supplementary Volume* (Apr. 1999) (with English translation).
Yamamoto et al., "E7080 (ER-203492-00), a Novel VEGF Receptor Tyrosine Kinase Inhibitor-III. Significant prolongation of life span in mice transplanted with human ovarian carcinoma based on inhibition of VEGF signaling," Abstract #50, *AACR*, Toronto, Canada (Apr. 5-9, 2003).

Yamamoto et al., "E7080 a novel multitargeted tyrosine kinase inhibitor, has direct anti-tumor activity via inhibition of KIT signaling in small cell lung cancer," Abstract #4636, *AACR*, Orlando, FL, (Mar. 27-31, 2004).
Yamamoto et al., "E7080, an oral multi-targeted tyrosine kinase inhibitor, has direct anti-tumor efficacy via inhibition of KIT signaling in small cell lung cancer," *Proceedings of the American Association for Cancer Research*,45:1070-1071 (Mar. 2004).
Yamamoto et al., "E7080, an oral multi-targeted tyrosine kinase inhibitor, has direct anti-tumor efficacy via inhibition of KIT signaling in gastrointestinal stromal tumor (GIST)," Abstract #4038, *97th Annual Meeting AACR*, Washington, DC. (Apr. 1-5, 2006).
Yanagihara et al., "Development and biological analysis of peritoneal metastasis mouse models for human scirrhous stomach cancer," *Cancer Sci.*, 96(6):323-332 (2005).
Yigitbasi et al., "Tumor Cell and Endothelial Cell Therapy of Oral Cancer by Dual Tyrosine Kinase Receptor Blockade", Cancer Research, 64, 7977-7984, 2004.
Yu, "Amorphous Pharmaceutical Solids:Preparation Characterization and Stabilization," *Advanced Drug Delivery Reviews*, 48:27-42 (2001) (XP009065056).
Zhang et al., "Overexpression of Platelet-Derived Growth Factor Receptor a in Endothelial Cells of Hepatocellular Carcinoma Associated with High Metastatic Potential," *Clin. Cancer Res.*, 11(24):8557-8563 (2005).
Zhou et al., "Correlation Research on VEGF Testing in Primary Gastric Cancer and Clinical Pathology Factor," *Journal of Practical Oncology*, 20(2):103-105 (Apr. 25, 2006) with English translation.
Zhu et al., "Fibroblast growth factor receptor 3 inhibition by short hairpin RNAs leads to apoptosis in multiple myeloma," *Mol. Cancer Ther.*, 4(5):787-798 (2005).
Zhu et al., "Inhibition of human leukemia in an animal model with human antibodies directed against vascular endothelial growth factor receptor 2. Correlation between antibody affinity and biological activity," *Leukemia*, 17:604-611 (2003).
Zieger et al., "Role of activating fibroblast growth factor receptor 3 mutations in the development of bladder tumors," *Clin. Cancer Res.*, 11:7709-7719 (2005).
ZK304709 (Proceedings of the American Association for Cancer Research, 46, (Abstract 5842), 2005.
Amendment, Response to Office Action under 37 C.F.R. § 1.111 and Information Disclosure Statement for U.S. Appl. No. 13/624,278, filed Jun. 28, 2013, 23 pages.
Applicant Observation for CN App. Ser. No. 200780017371.9, filed May 29, 2013, 6 pages (with English translation).
Argument and Amendment for JP App. Ser. No. 2008-556208, filed Mar. 21, 2013, 15 pages (with English translation).
Argument and Amendment for JP App. Ser. No. 2008.532141, filed Nov. 29,2012, 12 pages (with English translation).
Argument and Amendment for JP App. Ser. No. 2008.516724, filed Nov. 28, 2012, 22 pages (with English translation).
Argument and Amendment for JP. App. Ser. No. 2009-123432, dated Jun. 12, 2012, 12 pages (with English translation).
Argument and Amendment for JP. App. Ser. No. 2009-529019, dated Jul. 3, 2012, 14 pages (with English translation).
Chikahisa et al, "TSU-68 KDR/flk-1 inhibitor, can modulate the anti-tumor activity of paclitaxel by the induction of endothelial cell and tumor cell apoptosis," 61st Annual Meeting of the Japanese Cancer Association, 2002, 61(1374):443, 5 total pages (with English translation).
Explanation of Circumstances Concerning Accelerated Examination and Amendment for JP App. Ser. No. 2011-527665, filed May 10, 2012, 21 pages (with English translation).
Frings, "New Molecular Targeted Therapeutic Drugs Clinical Results of Bevacizumab in Non-Small Cell Lung Cancer (NSCLC)", *Jap. J. Lung Cancer*, Jun. 2006, 46(3):277-281 (with English Translation).
Jiang, "ZD6474: an Agent That Selectively Targets Both VEGFR Tyrosine Kinase and EGFR Tyrosine Kinase", *Jap. J. Lung Cancer*, Jun. 2006, 46(3):283-288 (with English translation).
Office Action for JP App. Ser. No. P2009-551518, dated Jun. 18, 2013, 5 pages (with English translation).

(56) References Cited

OTHER PUBLICATIONS

Response to Office Action for CA App. Ser. No. 2661702, filed Jul. 16, 2013, 13 pages.
Response to Office Action under 37 C.F.R.S. 1.111 and Information Disclosure Statement for U.S. Appl. No. 11/997,719, filed Jul. 3, 2013, 26 pages.
Amended Claims filed in EP App. Ser. No. 11798224.9, filed Aug. 2, 2013, 35 pages.
Amended Claims filed in RU App. Ser. No. 2013140169, dated Aug. 29, 2013, 17 pages (with English translation).
Amendment and Response to Office Action under 37 C.F.R § 1.111 for U.S. Appl. No. 12/439,339, dated Aug. 22, 2013, 14 pages.
Amendment filed in EP App. Ser. No. 12774278.1, filed Aug. 13, 2013, 12 pages.
Amendment filed in JP App. Ser. No. 2008-532141, filed Jul. 5, 2013, 2 pages (with English translation).
Demand for Appeal Trial filed in JP App. Ser. No. 2008-532141, filed Jul. 5, 2013, 10 pages (with English translation).
Nishio et al, "Phase 1 study of lenvatinib combined with carboplatin and paclitaxel in patients with non-small-cell lung cancer", British Journal of Cancer, 2013, 109:538-544.
Notice of Allowance for U.S. Appl. No. 12/741,682, dated Jun. 19, 2013, 10 pages.
Notice of Allowance issued in IL App. Ser. No. 175363, dated Aug. 13, 2013, 2 pages (with English translation).
Office Action for IL App. Ser. No. 200090, dated Jul. 24, 2013, 5 pages (with English translation).
Office Action for U.S. Appl. No. 12/039,381, dated Sep. 12, 2013, 15 pages.
Office Action for U.S. Appl. No. 13/238,085, dated Sep. 6, 2013, 10 pages.
Response to Office Action for MX App. Ser. No. MX/a/2012/002011, dated Aug. 29, 2013, 12 pages (with English translation).
Submission Document Before the Patent Office for CL App. U.S. Appl. No. 2012-00412, dated Aug. 31, 2012, 6 pages (with English translation).
Submission Documents re New Claim Set Before the Patent Office for AR App. Ser. No. P110100513, dated Aug. 27, 2013, 8 pages (with English translation).
Submission Documents re Preliminary Amendment Before the Patent Office U.S. Appl. No. 14/002,018, dated Aug. 28, 2013, 9 pages.
Submission Documents re RCE Before the Patent Office for U.S. Appl. No. 13/083,338, dated Aug. 28, 2013, 20 pages.
Submission of Reference Materials in KR App. Ser. No. 10-2008-7013685, filed Jul. 5, 2013, 43 pages, (with English translation).
Voluntary Amendment filed in CA App. Ser. No. 2704000, filed Aug. 6, 2013, 6 pages.
Amendment filed on Aug. 13, 2013 in JP App. Ser. No. P2009-540099, 8 pages (with English translation).
Amendment filed on Aug. 29, 2013 in CN App. Ser. No. 201280010898.X, 24 pages (with English translation).
Amendment filed on Aug. 6 2013, for JP App. Ser. No. 2009-551518, 6 pages (with English translation).
Amendment filed on Oct. 1, 2013 in in App. Ser. No. 10502/CHENP/2012, 10 pages.
Amendment filed on Sep. 23, 2013 in AU App. Ser. No. 2011270165, 35 pages.
Amendment for in App. Ser. No. 7026/CHENP/2013, dated Sep. 5, 2013, 8 pages.
Amendment in Canadian App. Ser. No. 2828946, dated Aug. 30, 2013, 14 pages.
Amendment in Israeli App. Ser. No. 200090, dated Oct. 2, 2013, 10 pages (with English translation).
Amendment in Korean App. Ser. No. 10-2012-7033886, dated Sep. 27, 2013, 34 pages (with English translation).
Amendment in Mexican App. Ser. No. MX/a/2012/014776, dated Oct. 21, 2013, 5 pages.
Amendment in Russian App. Ser. No. 2012158142, dated Oct. 17, 2013, 48 pages (with English translation).
Argument filed on Aug. 13, 2013 in JP App. Ser. No. 2009-540099, 10 pages (with English translation).
Argument filed on Aug. 6, 2013 for JP Patent Application No. 2009-551518, 18 pages (with English translation).
Colombian Office Action for App. Ser. No. 12-022608, dated Oct. 7, 2013, 10 pages (with English translation).
Ezzat et al., "Dual Inhibition of RET and FGFR4 Retains Medullary Thyroid Cancer Cell Growth," Clinical Cancer Research, Feb. 2005, 11:1336-1341.
Indian Office Action in App. Ser. No. 6415/CHENP/2008, dated Oct. 3, 2013, 2 pages.
International Preliminary Report on Patentability for App. Ser. No. PCT/JP2012/057949, dated Oct. 10, 2013, 7 pages.
Korean Office Action for App. Ser. No. 10-2009-7005657, issued on Sep. 30, 2013, 27 pages (with English translation).
Korean Office Action in KR App. Ser. No. 10-2008-7029472, dated Sep. 30, 2013, 27 pages (with English translation).
Mexican Office Action in App. Ser. No. MX/a/2010/008187, dated Aug. 21, 2013, 6 pages (with English translation).
Notice of Allowance for JP App. Ser. No. P2008-532141, dated Sep. 10, 2013, 5 pages (with English translation).
Notice of Allowance for U.S. Appl. No. 11/997,719, dated Sep. 13, 2013, 20 pages.
Notice of Allowance for U.S. Appl. No. 13/083,338, dated Sep. 26, 2013, 28 pages.
Notice of Allowance for U.S. Appl. No. 13/205,328, dated Oct. 3, 2013, 11 pages.
Notice of Allowance in CA App. Ser. No. 2661702, dated Sep. 26, 2013, 1 page.
Notice of Allowance in EP App. Ser. No. 04818213.3, dated Sep. 19, 2013, 2 pages.
Notice of Allowance in U.S. Appl. No. 12/741,682, dated Oct. 21, 2013, 12 pages.
Notice of Allowance in U.S. Appl. No. 13/624,278, dated Sep. 16, 2013, 20 pages.
Notice of Allowance issued in CN App. Ser. No. 200880115011.7, dated Aug. 5, 2013, 4 pages (with English translation).
Office Action for PH App. Ser. No. 1-2011-502441 on Oct. 1, 2013, 1 page.
Request for Examination in CA App. Ser. No. 2713930, dated Oct. 21, 2013, 8 pages.
Request for Re-Examination in CN App. Ser. No. 200780017371.9, dated Oct. 11, 2013, 9 pages (with English translation).
Response and Amendment for CA App. Ser. No. 2652442, dated Sep. 5, 2013, 17 pages.
Response filed in IN App. Ser. No. 1571/CHENP/2007, dated Oct. 30, 2013, 9 pages.
Response to Restriction Requirement in U.S. Appl. No. 13/238,085, dated Oct. 4, 2013, 3 pages.
Sattler et al., "Targeting c-Kit mutations: basic science to novel therapies," Leukemia Research, 2004, 28S1:S11-S20.
St. Bernard et al., "Fibroblast Growth Factor Receptors as Molecular Targets in Thyroid Carcinoma," Endocrinology, Mar. 2005, 146(3):1145-1153.
Submission Document Before the Patent Office re Rce in U.S. Appl. No. 13/205,328, dated Sep. 10, 2013, 12 pages.
Submission Document re Petition on Oct. 2, 2013 in CL App. Ser. No. 2012-00412, 22 pages (with English translation).
Submission Document re RCE and Information Disclosure Statement on Sep. 19, 2013 in U.S. Appl. No. 12/741,682, 19 pages.
Submission Document re RCE and Information Disclosure Statement on Oct. 18, 2013, in U.S. Appl. No. 12/524,754, 17 pages.
US Office Action for U.S. Appl. No. 11/997,543, dated Sep. 30, 2013, 88 pages.
Amended Claims filed in KR App. Ser. No. 10-2010-7011023, filed Jul. 17, 2013, 15 pages (with English translation).
Amended Specification filed in AU App. Ser. No. 2012246490, filed Aug. 2, 2013, 15 pages.
Decision of Final Rejection issued in CN App. Ser. No. 200780017371.9, dated Jul. 3, 2013, 16 pages (with English translation).

(56) References Cited

OTHER PUBLICATIONS

Matsui, "Extracellular matrix of linitis plastica as a possible new therapeutic target," *Surgical Treatment*, Sep. 2003, 89(3):301-306 (with English translation).
Notice of Allowance issued in CN App. Ser. No. 201080030508.6, dated Jul. 4, 2013, 4 pages (with English translation).
Notice of Allowance issued in EP App. Ser. No. 10015141.4, dated Jul. 1, 2013, 41 pages.
Notice of Allowance issued in JP App. Ser. No. P2008-556208, dated Jul. 9, 2013, 4 pages (with English translation).
Notice of Allowance issued in U.S. Appl. No. 12/524,754, dated Jul. 19, 2013, 11 pages.
Notice of Reasons for Rejection issued in JP App. Ser. No. P2009-540099, dated Jul. 2, 2013, 7 pages (with English translation).
Office Action issued in MX App. Ser. No. MX/a/2012/002011, dated Jul. 17, 2013, 6 pages (with English translation).
Response and Amended Claims filed in EP App. Ser. No. 08846814.5, filed Aug. 1, 2013, 14 pages.
Response and Amended Claims filed in EP App. Ser. No. 10809938.3, filed Jul. 19, 2013, 7 pages.
Response filed in IL App. Ser. No. 195282, filed Jul. 11, 2013, 13 pages (with English translation).
Response to Notice Prior to Examination filed in IL App. Ser. No. 217197, filed Jul. 31, 2013, 9 pages (with English translation).
International Search Report and International Preliminary Report on Patentability for PCT Application No. PCT/JP2011/064430, Sep. 13, 2011, 8 pages.
Lennartsson and Ronnstrand, "The Stem Cell Factor Receptor/c-Kit asa Drug Target in Cancer," *Current Cancer Drug Targets*, 2006, 6:65-75.
Rosen and Goldberg, "Scatter Factor 67:257-279 and Angiogenesis," *Advances in Cancer Research*, 1995, 67:257-279.
To and Tsao, "The roles of hepatocyte growth factor/scatter factor and Met receptor in human cancers (Review)," *Oncology Reports*, 1998, 5:1013-1024.
Turner and Grose, "Fibroblast growth factor signalling: from development to cancer," *Nature Reviews Cancer*, Feb. 2010, 10:116-129.
Wells and Santoro, "Targeting the *RET* Pathway in Thyroid Cancer," *Clinical Cancer Research*, 2009, 15:7119-7123.
Additional Response in IL App. Ser. No. 188670, dated Oct. 25, 2011, 4 pages (with English translation).
Advisory Action in U.S. Appl. No. 12/315,291, dated Mar. 24, 2011, 10 pages.
Amendment in AU App. Ser. No. 2005217325, dated Aug. 9, 2006, 11 pages.
Amendment in AU App. Ser. No. 2005217328, dated Aug. 9, 2006, 10 pages.
Amendment in AU App. Ser. No. 2006282456, dated Apr. 26, 2012, 6 pages.
Amendment in AU App. Ser. No. 2006282456, dated Jan. 25, 2008, 26 pages.
Amendment in AU App. Ser. No. 2007289787, dated Apr. 7, 2009, 16 pages.
Amendment in BD App. Ser. No. 184/2006, dated May 6, 2008, 3 pages.
Amendment in BD App. Ser. No. 184/2006, dated Sep. 26, 2007, 4 pages.
Amendment in BR App. Ser. No. PI0616799/3, dated May 29, 2012, 6 pages.
Amendment in CN App. Ser. No. 200580001760.3, dated May 15, 2007, 31 pages (with English translation).
Amendment in CN App. Ser. No. 200680021939.X, dated Dec. 18, 2007, 23 pages (with English translation).
Amendment in CN App. Ser. No. 200780019520.5, dated Nov. 27, 2008, 10 pages (with English translation).
Amendment in CN App. Ser. No. 2008800045113, dated Aug. 7, 2009, 36 pages (with English translation).
Amendment in EP App. Ser. No. 05719973.9, dated Oct. 30, 2006, 2 pages.
Amendment in EP App. Ser. No. 06796594.7, dated Apr. 19, 2012, 3 pages.
Amendment in EP App. Ser. No. 06796594.7, dated Jan. 11, 2008, 3 pages.
Amendment in EP App. Ser. No. 06796594.7, dated Nov. 16, 2007, 3 pages.
Amendment in EP App. Ser. No. 07793075.8, dated Jan. 26, 2011, 12 pages.
Amendment in EP App. Ser. No. 07793075.8, dated Mar. 3, 2009, 5 pages.
Amendment in EP App. Ser. No. 08711837.8, dated Sep. 8, 2009, 23 pages.
Amendment in EP App. Ser. No. 09713617.0, dated Sep. 1, 2010, 3 pages.
Amendment in IL App. Ser. No. 188670, dated May 2, 2012, 7 pages (with English translation).
Amendment in IL App. Ser. No. 197002, dated Feb. 11, 2009, 4 pages.
Amendment in IL App. Ser. No. 200466, dated Aug. 18, 2009, 28 pages.
Amendment in IN App. Ser. No. 1424/CHENP/2008, dated Apr. 27, 2012, 4 pages.
Amendment in JO App. Ser. No. 280/2006, dated Oct. 19, 2007, 3 pages (with English translation).
Amendment in JP App. Ser. No. 2007-532099, dated Dec. 25, 2007, 6 pages (with English translation).
Amendment in JP App. Ser. No. 2007-532099, dated Sep. 25, 2007, 28 pages (with English translation).
Amendment in JP App. Ser. No. 2008-530917, dated Dec. 13, 2012, 6 pages (with English translation).
Amendment in JP App. Ser. No. 2009-554285, dated Aug. 19, 2010, 7 pages (with English translation).
Amendment in JP App. Ser. No. P2009-510543, dated Nov. 9, 2009, 25 pages (with English translation).
Amendment in KR App. Ser. No. 10-2006-7013907, dated Sep. 28, 2007, 10 pages (with English translation).
Amendment in KR App. Ser. No. 10-2006-7013940, dated Oct. 1, 2007, 43 pages (with English translation).
Amendment in KR App. Ser. No. 10-2007-7026886, dated Dec. 27, 2007, 4 pages (with English translation).
Amendment in KR App. Ser. No. 10-2007-7026886, dated Nov. 21, 2007, 9 pages (with English translation).
Amendment in KR App. Ser. No. 10-2007-7026886, dated Oct. 27, 2009, 4 pages (with English translation).
Amendment in KR App. Ser. No. 10-2008-7029577, dated Apr. 1, 2009, 6 pages (with English translation).
Amendment in KR App. Ser. No. 10-2009-7013723, dated Aug. 10, 2009, 17 pages (with English translation).
Amendment in MY App. Ser. No. PI20071922, dated Jul. 17, 2008, 243 pages.
Amendment in NO App. Ser. No. 20080460, dated May 14, 2012, 4 pages (with English translation).
Amendment in PH App. Ser. No. 1-2007-502319, dated May 14, 2012, 3 pages.
Amendment in SA App. Ser. No. 06270287, dated Oct. 22, 2007, 12 pages.
Amendment in SG App. Ser. No. 200718614/1, dated Aug. 24, 2010, 13 pages.
Amendment in TH App. Ser. No. 0601004017, dated Sep. 25, 2007, 6 pages (with English translation).
Amendment in US App. Ser. No. 11/892,785, dated Dec. 17, 2008, 17 pages.
Amendment in U.S. Appl. No. 11/065,631, dated May 28, 2008, 16 pages.
Appeal in SA App. Ser. No. 06270287, dated Jun. 23, 2010, 4 pages (with English translation).
Argument Brief in KR App. Ser. No. 10-2007-7026886, dated Oct. 27, 2009, 7 pages (with English translation).
Communication re Intention to Grant Patent in EP App. Ser. No. 07793075.8, dated Nov. 9, 2012, 97 pages.
Communication re Intention to Grant Patent in EP App. Ser. No. 07805959.9, dated Jun. 21, 2011, 70 pages.

(56) References Cited

OTHER PUBLICATIONS

Coupling Reagents, "Advanced Automated Peptide Protein Technologies," Published Aug. 3, 2007, 4 pages.
Decision of Grant in RU App. Ser. No. 2008110932, dated Feb. 6, 2009, 29 pages (with English translation).
Decision to Grant Patent in EP App. Ser. No. 05719973.9, dated Jun. 1, 2012, 1 page.
Decision to Grant Patent in EP App. Ser. No. 07805959.9, dated Nov. 4, 2011, 2 pages.
Decision to Grant Patent in JP App. Ser. No. 2007-532099, dated Jan. 8, 2008, 5 pages (with English translation).
Decision to Grant Patent in JP App. Ser. No. 2008-530917, dated Jan. 15, 2013, 6 pages (with English translation).
Decision to Grant Patent in JP App. Ser. No. 2008-532065, dated Nov. 13, 2012, 6 pages (with English translation).
Decision to Grant Patent in JP App. Ser. No. P2009-510543, dated Feb. 2, 2010, 6 pages (with English translation).
Examination Report in AU App. Ser. No. 2005217325, dated Aug. 1, 2007, 2 pages.
Examination Report in AU App. Ser. No. 2005217328, dated Aug. 1, 2007, 2 pages.
Examination Report in AU App. Ser. No. 2007288793, dated Dec. 22, 2011, 2 pages.
Examination Report in AU App. Ser. No. 2007289787, dated Nov. 25, 2011, 2 pages.
Examination Report in AU App. Ser. No. 2008217931, dated Jun. 28, 2012, 3 pages.
Examination Report in PK App. Ser. No. 155/2005, dated Mar. 11, 2009, 2 pages.
Extended European Search Report in EP App. Ser. No. 06796594.7, dated Sep. 7, 2011, 5 pages.
Extended European Search Report in EP App. Ser. No. 07793075.8, dated Sep. 8, 2010, 6 pages.
Extended European Search Report in EP App. Ser. No. 07805959.9, dated Nov. 16, 2010, 6 pages.
Extended European Search Report in EP App. Ser. No. 08711837.8, dated Mar. 28, 2011, 5 pages.
Extended European Search Report in EP App. Ser. No. 09713617.0, dated Apr. 28, 2011, 5 pages.
Haleblian, "Characterization of Habits and Crystalline Modification of Solids and Their Pharmaceutical Applications," J Pharma. Sci., Aug. 1975, 64(8):1269-1288.
International Preliminary Report in International App. Ser. No. PCT/JP2007/066635, dated Mar. 12, 2009, 9 page.
International Preliminary Report in International App. Ser. No. PCT/JP2007/066185, dated Mar. 5, 2009, 6 pages.
International Preliminary Report in International App. Ser. No. PCT/JP2008/053066, dated Sep. 11, 2009, 12 pages.
International Preliminary Report in International App. Ser. No. PCT/IB2008/003880, dated Aug. 11, 2009, 4 pages.
International Preliminary Report in International App. Ser. No. PCT/JP2008/071881, dated Jul. 14, 2011, 7 pages pages.
International Preliminary Report in International App. Ser. No. PCT/JP2009/0524001, dated Oct. 14, 2010, 5 pages.
International Preliminary Report in Patentability in International App. Ser. No. PCT/JP2006/316331, dated Feb. 26, 2008, 5 pages.
International Preliminary Report on Patentability in International App. Ser. No. PCT/JP2005/003701, dated Sep. 16, 2006, 7 pages.
International Preliminary Report on Patentability in International App. Ser. No. PCT/JP2005/003704, dated Sep. 19, 2006, 7 pages.
International Search Report and Written Opinion in International App. Ser. No. PCT/JP2008/071881, dated Jan. 27, 2009, 12 pages.
International Search Report and Written Opinion in International App. Ser. No. PCT/JP2009/0524001, dated Mar. 10, 2009, 9 pages.
International Search Report in International App. Ser. No. PCT/IB2008/003880, dated Aug. 11, 2009, 7 pages.
International Search Report in International App. Ser. No. PCT/JP2005/003701, dated May 31, 2005, 6 pages (with English translation).
International Search Report in International App. Ser. No. PCT/JP2005/003704, dated May 31, 2005, 6 pages (with English translation).
International Search Report in International App. Ser. No. PCT/JP2006/316331, dated Oct. 17, 2006, 5 pages (with English translation).
International Search Report in International App. Ser. No. PCT/JP2007/066635, dated Oct. 16, 2007, 5 pages.
International Search Report in International App. Ser. No. PCT/JP2007/066185, dated Sep. 25, 2007, 4 pages.
International Search Report in International App. Ser. No. PCT/JP2008/053066, dated May 20, 2008, 8 pages.
Interview Summary in U.S. Appl. No. 12/558,982, dated Oct. 20, 2011, 3 pages.
Issue Notification in U.S. Appl. No. 11/508,322, dated Dec. 1, 2010, 1 page.
Issue Notification in U.S. Appl. No. 12/031,568, dated Jan. 30, 2013, 4 pages (with English translation).
Issue Notification in U.S. Appl. No. 12/315,291, dated Jul. 27, 2011, 5 pages.
Issue Notification in U.S. Appl. No. 12/558,982, dated Sep. 26, 2012, 1 page.
Issued Notification in U.S. Appl. No. 11/892,785, dated Aug. 18, 2010, 1 page.
Maintenance and Response to EP Search Report in EP App. Ser. No. 06796594.7, dated Dec. 21, 2011, 43 pages.
Matsushima et al., "Preparation of pyridine and pyrimidine derivatives as inhibitors of hepatocyte growth factor receptor (HGFR)," Hcaplus, 2005, 977021.
Miller et al., "Genomic amplification of MET with boundaries within fragile site FRA7G and upregulation of MET pathways in esophageal adenocarcinoma," Oncogene, 2005, 25(3):409-418.
Nakagawa et al., "E7050: A dual c-Met and VEGFR-2 tyrosine kinase inhibitor promotes tumor regression and prolongs survival in mouse xenograft models ," Cancer Sci., 2010, 101:210-215.
Naran eta l., "Inhibition of HGF/MET as therapy for malignancy," Expert Opin. Ther. Targets, 2009, p. 569-581.
Neidle, "Cancer Drug Design and Discovery" Elsevier/Academic Press, 2008, pp. 427-431.
Nicolaus, "Symbiotic Approach to Drug Design," Decision Making Drug Res., Jan. 1983, 173-186.
Notice of Acceptance in AU App. Ser. No. 2005217325, dated Nov. 20, 2007, 3 pages.
Notice of Acceptance in AU App. Ser. No. 2005217328, dated Sep. 24, 2007, 3 pages.
Notice of Acceptance in AU App. Ser. Appl. No. 2006282456, dated Aug. 17, 2009, 1 page.
Notice of Acceptance in AU App. Ser. No. 2007288793, dated Apr. 10, 2012, 3 pages.
Notice of Acceptance in AU App. Ser. No. 2007289787, dated Mar. 16, 2012, 3 pages.
Notice of Acceptance in DB App. Ser. No. 60/2005, dated Nov. 16, 2006, 1 page.
Notice of Acceptance in NZ App. Ser. No. 547517, dated Mar. 6, 2009, 1 page.
Notice of Acceptance in NZ App. Ser. No. 566793, dated Feb. 12, 2010, 2 pages.
Notice of Allowability in PH App. Ser. No. 1-2007-502319, dated Feb. 29, 2012, 1 page.
Notice of Allowance in CA App. Ser. No. 2605854, dated Apr. 7, 2010, 1 page.
Notice of Allowance in CN App. Ser. No. 200680021939.X, dated Jan. 11, 2012, 4 pages (with English translation).
Notice of Allowance in CN App. Ser. No. 200780019200.X, dated Jan. 15, 2013, 4 pages (with English translation).
Notice of Allowance in CN App. Ser. No. 200780019520.5, dated Apr. 27, 2011, 4 pages (with English translation).
Notice of Allowance in ID App. Ser No. W-00 2008 00601, dated Oct. 17, 2012, 12 pages (with English translation).
Notice of Allowance in KR App. Ser. No. 10-2006-7013907, dated Jan. 14, 2008, 3 pages (with English translation).
Notice of Allowance in KR App. Ser. No. 10-2006-7013940, dated Jan. 14, 2008, 3 pages (with English translation).

(56) References Cited

OTHER PUBLICATIONS

Notice of Allowance in MX App. Ser. No. MX/a/2008/002156, dated Oct. 15, 2010, 3 pages (with English translation).
Notice of Allowance in MY App. Ser. No. PI20071922, dated Jan. 15, 2010, 3 pages.
Notice of Allowance in PK App. Ser. No. 1024/2006, dated Nov. 2, 2010, 1 page.
Notice of Allowance in PK App. Ser. No. 375/2008, dated Nov. 2, 2010, 1 page.
Notice of Allowance in RU App. Ser. No. 2006134254, dated Jan. 14, 2008, 30 pages (with English translation).
Notice of Allowance in TW App. Ser. No. 095130665, dated Sep. 7, 2012, 4 pages (with English translation).
Notice of Allowance in U.S. Appl. No. 11/892,785, dated Apr. 5, 2010, 23 pages.
Notice of Allowance in U.S. Appl. No. 11/508,322, dated Sep. 15, 2009, 6 pages.
Notice of Allowance in U.S. Appl. No. 12/031,568, dated Jun. 1, 2012, 23 pages.
Notice of Allowance in U.S. Appl. No. 12/031,568, dated Oct. 19, 2011, 11 pages.
Notice of Allowance in U.S. Appl. No. 12/031,568, dated Sep. 18, 2012, 6 pages.
Notice of Allowance in U.S. Appl. No. 12/315,291, dated Apr. 26, 2011, 6 pages.
Notice of Allowance in U.S. Appl. No. 12/558,982, dated Apr. 3, 2012, 11 pages.
Notice of Allowance in U.S. Appl. No. 12/558,982, dated May 25, 2012, 20 pages.
Notice of Allowance in U.S. Appl. No. 11/065,631, dated Jan. 2, 2009, 6 pages.
Notice of Allowance in U.S. Appl. No. 11/065,631, dated Sep. 9, 2008, 10 pages.
Notice of Allowance in VN App. Ser. No. 1-2008-00723, dated Aug. 19, 2010, 2 pages (with English translation).
Notice of Allowance in ZA App. Ser. No. 2007/09572, dated Mar. 12, 2009, 1 pages.
Notice of Final Rejection in KR App. Ser. No. 10-2009-7013723, dated Jul. 29, 2011, 4 pages (with English translation).
Notice of Grant in KR App. Ser. No. 10-2007-7026886, dated Dec. 31, 2009, 5 pages (with English translation).
Notice of Non-Substantive Deficiencies Prior to Allowance in IL App. Ser. No. 197141, dated Feb. 3, 2013, 16 pages (with English translation).
Notice Prior to Allowance in IL App. Ser. No. 188670, dated Sep. 12, 2011, 2 pages (with English translation).
Notice Prior to Allowance in IL App. Ser. No. 197002, dated Oct. 28, 2012, 2 pages (with English translation).
Notice Prior to Examination in IL App. Ser. No. 188670, dated Aug. 13, 2009, 3 pages (with English translation).
Notice Prior to Examination in IL App. Ser. No. 197002, dated Mar. 23, 2010, 3 pages (with English translation).
Notice Prior to Examination in IL App. Ser. No. 197141, dated Mar. 23, 2010, 3 pages (with English translation).
Notice Prior to Examination in IL App. Ser. No. 200466, dated Jun. 22, 2010, 3 pages (with English translation).
Office Action in AU App. Ser. No. 2006282456, dated Jun. 12, 2009, 1 pages.
Office Action in BD App. Ser. No. 184/2006, dated May 11, 2007, 2 pages.
Office Action in CA App. Ser. No. 2543859, dated Aug. 19, 2008, 5 pages.
Office Action in CA App. Ser. No. 2543861, dated Aug. 19, 2008, 4 pages.
Office Action in CA App. Ser. No. 2605854, dated Jul. 29, 2009, 2 pages.
Office Action in CN App. Ser. No. 200680021939.X, dated Mar. 30, 2011, 7 pages (with English translation).
Office Action in CN App. Ser. No. 200680021939.X, dated May 27, 2010, 9 pages (with English translation).
Office Action in CN App. Ser. No. 200680021939.X, dated Sep. 2, 2010, 10 pages (with English translation).
Office Action in CN App. Ser. No. 200780019200.X, dated Apr. 6, 2012, 9 pages (with English translation).
Office Action in CN App. Ser. No. 200780019520.5, dated Dec. 21, 2010, 7 pages (with English translation).
Office Action in CN App. Ser. No. 200780019520.5, dated Sep. 27, 2010, 8 pages (with English translation).
Office Action in CN App. Ser. No. 2008800045113, dated Jul. 5, 2011, 10 pages (with English translation).
Office Action in DB App. Ser. No. 60/2005, dated Jul. 25, 2006, 2 pages.
Office Action in EP App. Ser. No. 05719973.9, dated Feb. 11, 2011, 7 pages.
Office Action in EP App. Ser. No. 05719973.9, dated Nov. 2, 2011, 4 pages.
Office Action in EP App. Ser. No. 07793075.8, dated Mar. 1, 2011, 3 pages.
Office Action in ID App. Ser No. W-00 2008 00601, dated Jan. 13, 2012, 4 pages (with English translation).
Office Action in IL App. Ser. No. 188670, dated Jul. 3, 2011, 2 pages (with English translation).
Office Action in IL App. Ser. No. 197002, dated Feb. 8, 2012, 2 pages (with English translation).
Office Action in IL App. Ser. No. 197141, dated Feb. 22, 2012, 18 pages (with English translation).
Office Action in IN App. Ser. No. 1424/CHENP/2008, dated Sep. 19, 2011, 18 pages.
Office Action in JP App. Ser. No. 2008-530917, dated Oct. 23, 2012, 4 pages (with English translation).
Office Action in JP App. Ser. No. P2009-510543, dated Sep. 29, 2009, 7 pages (with English translation).
Office Action in KR App. Ser. No. 10-2006-7013907, dated Jul. 28, 2007, 7 pages (with English translation).
Office Action in KR App. Ser. No. 10-2006-7013940, dated Jul. 31, 2007, 19 pages (with English translation).
Office Action in KR App. Ser. No. 10-2007-7026886, dated Aug. 27, 2009, 5 pages (with English translation).
Office Action in KR App. Ser. No. 10-2009-7013723, dated May 19, 2011, 10 pages (with English translation).
Office Action in NZ App. Ser. Appl. No. 566793, dated Dec. 4, 2009, 1 page.
Office Action in PH App. Ser. No. 1-2007-502319, dated Dec. 16, 2011, 1 page.
Office Action in PK App. Ser. No. 1024/2006, dated Dec. 12, 2007, 3 pages.
Office Action in PK App. Ser. No. 1024/2006, dated Feb. 24, 2009, 2 pages.
Office Action in PK App. Ser. No. 1024/2006, dated Oct. 21, 2008, 2 pages.
Office Action in PK App. Ser. No. 155/2005, dated Nov. 17, 2007, 2 pages.
Office Action in PK App. Ser. No. 375/2008, dated Feb. 24, 2009, 1 page.
Office Action in PK App. Ser. No. 375/2008, dated Jul. 20, 2009, 2 pages.
Office Action in PK App. Ser. No. 375/2008, dated Oct. 21, 2008, 3 pages.
Office Action in RU App.Ser. No. 2006134254, dated Oct. 13, 2006, 4 pages (with English translation).
Office Action in RU App. Ser. No. 2006134254, dated Sep. 18, 2007, 9 pages (with English translation).
Office Action in RU App. Ser. No. 2008110932, dated Dec. 3, 2008, 6 pages (with English translation).
Office Action in TW App. Ser. No. 095130665, dated Mar. 2, 2012, 8 pages (with English translation).
Office Action in U.S. Appl. No. 11/508,322, dated Dec. 18, 2008, 19 pages.
Office Action in U.S. Appl. No. 11/508,322, dated May 29, 2009, 8 pages.
Office Action in U.S. Appl. No. 12/031,568, dated Aug. 13, 2010, 15 pages.

(56) References Cited

OTHER PUBLICATIONS

Office Action in U.S. Appl. No. 12/031,568, dated Feb. 5, 2010, 16 pages.
Office Action in U.S. Appl. No. 12/031,568, dated May 12, 2011, 26 pages.
Office Action in U.S. Appl. No. 12/315,291, dated Jan. 12, 2011, 9 pages.
Office Action in U.S. Appl. No. 12/315,291, dated Jun. 7, 2010, 20 pages.
Office Action in U.S. Appl. No. 12/558,982, dated Apr. 5, 2011, 31 pages.
Office Action in U.S. Appl. No. 12/558,982, dated Aug. 29, 2011, 13 pages.
Office Action in U.S. Appl. No. 12/867,646, dated Oct. 26, 2011, 37 pages.
Office Action in U.S. Appl. No. 11/065,631, dated Feb. 28, 2008, 12 pages.
Office Action in VN App. Ser. No. 1-2008-00723, dated Mar. 11, 2010, 4 pages (with English translation).
Official Letter in AU App. Ser. No. 2006282456, dated May 15, 2012, 1 page.
Official Letter in AU App. Ser. No. 2006282456, dated Sep. 24, 2012, 259 pages.
Official Letter in BD App. Ser. No. 184/2006, dated Feb. 2, 2012, 1 page.
Official Letter re Deficiencies in sequence listing in EP App. Ser. No. 06796594.7, dated Mar. 10, 2008, 3 pages.
Official Letter re Granting Patent in EP App. Ser. No. 06796594.7, dated Sep. 25, 2012, 270 pages.
Official Letter re Intention to Grant Patent in EP App. Ser. No. 05719973.9, dated Feb. 6, 2012, 553 pages.
Official Letter re invitation to declare maintenance in EP App. Ser. No. 06796594.7, dated Sep. 26, 2011, 1 page.
Official Letter re invitation to declare maintenance in EP App. Ser. No. 07793075.8, dated Sep. 27, 2010, 1 page.
Official Letter re invitation to declare maintenance in EP App. Ser. No. 07805959.9, dated Dec. 3, 2010, 1 page.
Official Letter re invitation to declare maintenance in EP App. Ser. No. 08711837.8, dated Apr. 14, 2011, 1 page.
Official Letter re invitation to declare maintenance in EP App. Ser. No. 09713617.0, dated May 17, 2011, 5 pages.
Petition in JP App. Ser. No. 2007-532099, dated Dec. 25, 2007, 3 pages (with English translation).
Petition in JP App. Ser. No. 2007-532099, dated Sep. 25, 2007, 3 pages (with English translation).
Petition in JP App. Ser. No. 2009-554285, dated Aug. 19, 2010, 3 pages (with English translation).
Preliminary Amendment in U.S. Appl. No. 10/577,043, dated Apr. 24, 2006, 12 pages.
Preliminary Amendment in U.S. Appl. No. 10/577,065, dated Apr. 24, 2006, 11 pages.
Preliminary Amendment in U.S. Appl. No. 11/508,322, dated May 15, 2007, 4 pages.
Preliminary Amendment in U.S. Appl. No. 11/508,322, dated May 19, 2008, 15 pages.
Preliminary Amendment in U.S. Appl. No. 11/508,322, dated Nov. 5, 2007, 28 pages.
Preliminary Amendment in U.S. Appl. No. 11/892,785, dated Apr. 7, 2008, 16 pages.
Preliminary Amendment in U.S. Appl. No. 12/031,568, dated Jun. 6, 2008, 7 pages.
Preliminary Amendment in U.S. Appl. No. 12/315,291, dated Mar. 19, 2009, 17 pages.
Preliminary Amendment in U.S. Appl. No. 12/527,633, dated Apr. 14, 2010, 58 pages.
Preliminary Amendment in U.S. Appl. No. 12/527,633, dated Aug. 18, 2009, 62 page.
Preliminary Amendment in U.S. Appl. No. 12/867,646, dated Aug. 13, 2010, 5 pages.

Registry's Letter in MT App. Ser. No. 3723, dated Oct. 29, 2007, 1 page.
Registry's Letter in MT App. Ser. No. 3723, dated Sep. 29, 2007, 1 page.
Reply to Notice of Non-Compliant Amendment in U.S. Appl. No. 12/315,291, dated Nov. 12, 2010, 3 pages.
Response in EP App. Ser. No. 06796594.7, dated Mar. 31, 2008, 3 pages.
Response to Advisory Action in U.S. Appl. No. 12/315,291, dated Mar. 31, 2011, 6 pages.
Response to EESR in EP App. Ser. No. 09713617.0, dated Sep. 2, 2011, 12 pages.
Response to Examination Report in AU App. Ser. No. 2005217325, dated Oct. 26, 2007, 33 pages.
Response to Examination Report in AU App. Ser. No. 2005217328, dated Sep. 20, 2007, 6 pages.
Response to Examination Report in AU App. Ser. No. 2007288793, dated Mar. 30, 2012, 5 pages.
Response to Extended European Search Report in EP App. Ser. No. 07793075.8, dated Nov. 8 2010, 11 pages.
Response to Extended European Search Report in EP App. Ser. No. 07805959.9, dated Mar. 29, 2011, 2 pages.
Response to Hearing Notice in IN App. Ser. No. 1424/CHENP/2008, dated Sep. 11, 2012, 14 pages.
Response to Notice of Incomplete Reply in U.S. Appl. No. 11/892,785, dated Apr. 17, 2008, 7 pages.
Response to Notice of Missing Parts and Preliminary Amendment in U.S. Appl. No. 11/892,785, dated Mar. 17, 2008, 4 pages.
Response to Notice Prior to Examination in IL App. Ser. No. 188670, dated Nov. 22, 2009, 29 pages (with English translation).
Response to Notice Prior to Examination in IL App. Ser. No. 197002, dated Oct. 13, 2010, 18 pages (with English translation).
Response to Notice Prior to Examination in IL App. Ser. No. 197141, dated Jun. 1, 2010, 22 pages (with English translation).
Response to Office Action in AU App. Ser. No. 2006282456, dated Jul. 16, 2009, 2 pages.
Response to office action in AU App. Ser. No. 2007289787, dated Feb. 16, 2012, 27 pages.
Response to Office Action in BD App. Ser. No. 184/2006, dated Dec. 13, 2007, 2 pages.
Response to Office Action in CA App. Ser. No. 2605854, dated Oct. 8, 2009, 18 pages.
Response to Office Action in CN App. Ser. No. 200680021939.X, dated Jul. 27, 2010, 44 pages (with English translation).
Response to Office Action in CN App. Ser. No. 200680021939.X, dated Oct. 28, 2010, 40 pages (with English translation).
Response to Office Action in CN App. Ser. No. 200680021939.X, dated May 20, 2011, 39 pages (with English translation).
Response to office action in CN App. Ser. No. 200780019200.X, dated Jul. 24, 2012, 49 pages (with English translation).
Response to office action in CN App. Ser. No. 200780019520.5, dated Dec. 3, 2010, 28 pages (with English translation).
Response to office action in CN App. Ser. No. 200780019520.5, dated Feb. 21, 2011, 7 pages (with English translation).
Response to office action in EP App. Ser. No. 05719973.9, dated Dec. 21, 2011, 150 pages.
Response to office action in EP App. Ser. No. 05719973.9, dated May 24, 2011, 26 pages.
Response to office action in EP App. Ser. No. 07793075.8, dated May 27, 2011, 17 pages.
Response to office action in ID App. Ser No. W-00 2008 00601, dated Jun. 18, 2012, 3 pages (with English translation).
Response to office action in IL App. Ser. No. 188670, dated Aug. 15, 2011, 43 pages (with English translation).
Response to office action in IL App. Ser. No. 197002, dated Feb. 29, 2012, 7 pages (with English translation).
Response to office action in IL App. Ser. No. 197141, dated Jun. 6, 2012, 10 pages (with English translation).
Response to office action in IN App. Ser. No. 1424/CHENP/2008, dated Jan. 18, 2012, 17 pages.
Response to office action in JP App. Ser. No. 2008-530917, dated Dec. 13, 2012, 9 pages (with English translation).

(56) References Cited

OTHER PUBLICATIONS

Response to office action in JP App. Ser. No. P2009-510543, dated Nov. 9, 2009, 12 pages (with English translation).
Response to office action in KR App. Ser. No. 10-2006-7013907, dated Sep. 28, 2007, 10 pages (with English translation).
Response to office action in KR App. Ser. No. 10-2006-7013940, dated Oct. 1, 2007, 20 pages (with English translation).
Response to office action in NZ App. Ser. No. 566793, dated Jan. 17, 2010, 17 pages.
Response to office action in PH App. Ser. No. 1-2007-502319, dated Feb. 6, 2012, 19 pages.
Response to office action in PK App. Ser. No. 1024/2006, dated Apr. 7, 2008, 17 pages.
Response to office action in PK App. Ser. No. 1024/2006, dated Apr. 20, 2009, 14 pages.
Response to office action in PK App. Ser. No. 1024/2006, dated Jan. 29, 2009, 6 pages.
Response to office action in PK App. Ser. No. 155/2005, dated Jan. 4, 2008, 34 pages.
Response to office action in PK App. Ser. No. 375/2008, dated Apr. 8, 2009, 19 pages.
Response to office action in PK App. Ser. No. 375/2008, dated Dec. 20, 2008, 1 page.
Response to office action in PK App. Ser. No. 375/2008, dated Sep. 1, 2009, 20 pages.
Response to office action in RU App. Ser. No. 2006134254, dated Dec. 15, 2006, 23 pages (with English translation).
Response to office action in RU App. Ser. No. 2006134254, dated Nov. 20, 2007, 32 pages (with English translation).
Response to office action in RU App. Ser. No. 2008110932, dated Jan. 26, 2009, 29 pages (with English translation).
Response to office action in TW App. Ser. No. 095130665, dated May 28, 2012, 379 pages (with English translation).
Response to office action in U.S. Appl. No. 11/508,322, dated Aug. 31, 2009, 11 pages.
Response to office action in U.S. Appl. No. 11/508,322, dated Mar. 18, 2009, 20 pages.
Response to office action in U.S. Appl. No. 12/031,568, dated Aug. 12, 2011, 12 pages.
Response to office action in U.S. Appl. No. 12/031,568, dated Jun. 2, 2010, 13 pages.
Response to office action in U.S. Appl. No. 12/315,291, dated Aug. 18, 2010, 8 pages.
Response to office action in U.S. Appl. No. 12/315,291, dated Feb. 28, 2011, 8 pages.
Response to office action in U.S. Appl. No. 12/558,982, dated Jul. 5, 2011, 21 pages.
Response to office action in VN App. Ser. No. 1-2008-00723, dated May 10, 2010, 7 pages (with English translation).
Response to Restriction Requirement in U.S. Appl. No. 11/892,785, dated Oct. 30, 2009, 16 pages.
Response to Restriction Requirement in U.S. Appl. No. 11/065,631, dated Nov. 26, 2007, 16 pages.
Restriction Requirement in U.S. Appl. No. 11/892,785, dated Oct. 7, 2009, 5 pages.
Restriction Requirement in U.S. Appl. No. 12/359,475, dated Mar. 7, 2011, 5 pages.
Restriction Requirement in U.S. Appl. No. 12/527,633, dated Aug. 13, 2012, 10 pages.
Restriction Requirement in U.S. Appl. No. 11/065,631, dated Oct. 25, 2007, 8 pages.
Saeki eta l., "Concurrent overexpression of Ets-1 and c-Met correlates with a phenotype of high cellular motility in human esophageal cancer," International J Cancer, 2002, 98(1):8-13.
Submission Document re RCE and Amendment in U.S. Appl. No. 12/031,568, dated Oct. 26, 2010, 23 pages.
Submission Document re RCE and Information Disclosure Statement in U.S. Appl. No. 11/065,631, dated Oct. 8, 2008, 7 pages.
Submission Document re RCE and Information Disclosure Statement in U.S. Appl. No. 12/558,982, dated May 9, 2012, 36 pages.
Submission Document re RCE in U.S. Appl. No. 12/031,568, dated Aug. 30, 2012, 12 pages.
Submission Document re RCE in U.S. Appl. No. 12/031,568, dated Jan. 18, 2012, 11 pages.
Submission Document re RCE in U.S. Appl. No. 12/558,982, dated Nov. 29, 2011, 13 pages.
Supplemental Notice of Allowance in U.S. Appl. No. 12/315,291, dated Jul. 21, 2011, 4 pages.
Supplemental Search Report in EP App. Ser. No. 05719973.9, dated Dec. 6, 2007, 3 pages.
Supplemental Search Report in EP App. Ser. No. 05719976.2, dated Dec. 6, 2007, 3 pages.
Varvoglis et al., "Chemical Transformations Induced by Hypervalent Iodine Reagents," Tetrahedron, 1997, 53(4):1179-1255.
Voluntary Amendment in BR App. Ser. No. PI0616799/3, dated May 29, 2009, 21 pages.
Voluntary Amendment in CA App. Ser. No. 2605854, dated Oct. 23, 2007, 14 pages.
Voluntary Amendment in CA App. Ser. No. 2661702, dated Feb. 24, 2009, 4 pages.
Voluntary Amendment in CA App. Ser. No. 2679602, dated Aug. 20, 2009, 6 pages.
Voluntary Amendment in IN App. Ser. No. 1424/CHENP/2008, dated Mar. 24, 2008, 257 pages.
Voluntary Amendment in IN App. Ser. No. 5625/CHENP/2009, dated Sep. 23, 2009, 147 pages.
Voluntary Amendment in LK App. Ser. No. 14703, dated Mar. 31, 2011, 256 pages.
Voluntary Amendment in TW App. Ser. No. 095130665, dated Mar. 20, 2009, 36 pages (with English translation).
Voluntary Amendments in AU App. Ser. No. 2007288793, dated May 29, 2009, 9 pages.
Voluntary Amendments in AU App. Ser. No. 2008217931, dated Nov. 18, 2009, 17 pages.
Watson et al , "Inhibition of c-Met as a therapeutic strategy for esophageal adenocarcinoma," Neoplasia, 2006, 8(11):949-955.
Written Verdict in SA App. Ser. No. 06270287, dated Feb. 17, 2013, 11 pages (with English translation).
Amendment and RCE submission documents filed in U.S. Appl. No. 12/039,381, dated Oct. 23, 2013, 13 pages.
Amendment and Response filed in U.S. Appl. No. 11/997,543, dated Dec. 19, 2013, 38 pages.
Amendment filed in BR App. Ser. No. BR112012032462-4, dated Nov. 4, 2013, 21 pages (with English translation).
Amendment filed in EP App. Ser. No. 12793322.4, dated Nov. 28, 2013, 6 pages.
Amendment filed in KR App. Ser. No. 10-2008-7029472, dated Nov. 20, 2013, 81 pages (with English translation).
Amendment filed in KR App. Ser. No. 10-2013-7020616, dated Nov. 22, 2013, 22 pages (with English translation).
International Preliminary Report on Patentability in International App. Ser. No. PCT/JP2012/060279, dated Oct. 23, 2013, 11 pages.
International Preliminary Report on Patentability in International App. Ser. No. PCT/JP2012/062509, dated Nov. 28, 2013, 11 pages.
Notice of Allowance in IL App. Ser. No. 197141, dated Oct. 27, 2013, 2 pages (with English translation).
Notice of Allowance in IL App. Ser. No. 200090, dated Nov. 18, 2013, 5 pages (with English translation).
Notice of Allowance in JP App. Ser. No. P2009-551518, dated Oct. 22, 2013, 5 pages (with English translation).
Notice of Allowance in KR App. Ser. No. 10-2008-7013685, dated Nov. 29, 2013, 3 pages (with English translation).
Notice of Allowance in U.S. Appl. No. 12/439,339, dated Nov. 7, 2013, 64 pages.
Notice of Allowance in U.S. Appl. No. 12/524,754, dated Nov. 22, 2013, 12 pages.
Office Action in CA App. Ser. No. 2652442, dated Oct. 4, 2013, 2 pages.
Office Action in CN App. Ser. No. 200680020317.5, dated Nov. 28, 2013, 8 pages (with English translation).
Office Action in CN App. Ser. No. 201180030568.2, dated Oct. 12, 2013, 11 pages (with English translation.

(56) References Cited

OTHER PUBLICATIONS

Office Action in CO App. Ser. No. 12-022608, dated Dec. 17, 2013, 12 pages (with English translation).
Office Action in IL App. Ser. No. 205512, dated Oct. 28, 2013, 5 pages (with English translation).
Office Action in IL App. Ser. No. 207089, dated Nov. 25, 2013, 6 pages (with English translation).
Office Action in IN App. Ser. No. 1571/CHENP/2007, dated Oct. 23, 2013, 2 pages.
Office Action in IN App. Ser. No. 1571/CHENP/2007, Dec. 9, 2013, 2 pages.
Office Action in KR App. Ser. No. 10-2008-7027527, dated Dec. 9, 2013, 6 pages (with English translation).
Office Action in KR App. Ser. No. 10-2008-7029577, dated Dec. 30, 2013, 7 pages (with English translation).
Office Action in MX App. Ser. No. MX/a/2010/008187, dated Dec. 5, 2013, 8 pages (with English translation).
Office Action in MX App. Ser. No. MX/a/2012/002011, dated Nov. 21, 2013, 8 pages (with English translation).
Office Action in RU App. Ser. No. 2013139556, dated Dec. 2, 2013, 6 pages (with English translation).
Office Action in U.S. Appl. No. 13/238,085, dated Nov. 12, 2013, 74 pages.
Office Action in VN App. Ser. No. 1-2011-03484, dated Dec. 31, 2013, 2 pages (with English translation).
Preliminary Amendment filed in EP App. Ser. No. 12786619.2, dated Nov. 13, 2013, 7 pages.
Preliminary Amendment filed in U.S. Appl. No. 14/117,276, dated Nov. 12, 2013, 11 pages.
Preliminary Amendment filed in U.S. Appl. No. 14/122,339, dated Nov. 26, 2013, 10 pages.
Response filed in CA App. Ser. No. 2652442, dated Jan. 8, 2014, 5 pages.
Response filed in CO App. Ser. No. 12-022608, dated Nov. 13, 2013, 13 pages (with English translation).
Response filed in KR App. Ser. No. 10-2009-7005657, dated Nov. 21, 2013, 46 pages (with English translation).
Response filed in MX App. Ser. No. MX/a/2010/008187, dated Nov. 4, 2013, 21 pages (with English translation).
Response filed in PH App. Ser. No. 1-2011-502441, dated Nov. 4, 2013, 28 pages.
Submission documents re RCE filed in U.S. Appl. No. 11/997,719, dated Dec. 11, 2013, 10 pages.
Submission documents re RCE filed in U.S. Appl. No. 13/083,338, dated Dec. 2, 2013, 5 pages.
Submission documents re RCE filed in U.S. Appl. No. 13/205,328, dated Dec. 30, 2013, 1 page.
Submission documents re RCE filed in U.S. Appl. No. 13/624,278, dated Dec. 13, 2013, 10 pages.
Voluntary Amendment filed in CA App. Ser. No. 2802644, dated Nov. 22, 2013, 25 pages.
Wang, "Drugs of Today, Everolimus in renal cell carcinoma," Journals on the Web, Aug. 2010, vol. 46, issue 8, 1 page (abstract only).
Yamori et al., "Current Treatment of Solid Tumors New Approaches of Treatment, Drug Treatment, Kinase Inhibitors/Kokeigan no Saishin Chiryo Chiryo no Aratana Torikumi Yakubutsu Ryoho Kinase Inhibitors," JP J Clin Med., Jun. 1, 2010, 68(6):1059-1066.
Amended claims in EP App. Ser. No. 04807580.8, dated Jun. 16, 2014, 7 pages.
Amended Claims in MY App. Ser. No. PI2011700172, dated in Jul. 3, 2014, 15 pages.
Besson et al., "PTEN/MMAC1/TEP1 in signal transduction and tumorigenesis," EP J Biochem., 1999, 263:605-611.
Comments re Board of Appeal in EP App. Ser. No. 04807580.8, dated Jul. 7, 2014, 3 pages.
Dankort et al., "Braf V660E cooperaties with Pten loss to induce metastic melanoma," Nature Genetics, 2009, 41(5):544-552.
Davies et al., "Mutations of the BRAF gene in human cancer," Nature, Jun. 27, 2002, 417:949-954.

Finn et al., "A multicenter, open-label, phase 3 trial to compare the efficacy and safety of lenvatinib (E7080) versus sorafenib in first-line treatment of subjects with unresectable hepatocellular carinoma," Am Soc Clin Oncol Annual Meeting Abstract, May 31, 2014, 5 pages.
Fujii et al., "Angiogenesis Inhibitor/Kekkan Shinsei Sogaiyaku," Clin Gastroenterol., May 25, 2004, 19:220-227.
Havel et al., "E7080 (lenvatinib) in addition to best supportive care (BSC) versus (BSC) alone in third-line or greater nonsquamous, non-small cell lung cancer (NSCLC)," Am Soc Clin Oncol Annual Meeting Abstract, May 31, 2014, abstract 8043, 4 pages.
Matsui et al., "Multi-Kinase Inhibitor E7080 Suppresses Lymph Node and Lung Metastases of Human Mammary Breast Tumor MDA-MB-231 via Inhibition of Vascular Endothelial Growth Factor-Receptor (VEGF-R) 2 and VEGF-R3 Kinase," Clin Cancer Res., 2008, 14:5459-5465.
Nakazawa, "Combination strategy of lenvatinib: Maximizing its anti-angiogenesis efficacy," Tsukuba Res Laboratory, Eisai Co., Ltd., Ibaraki, Japan, Jun. 27, 2014, 10 pages.
Notice of Allowance in U.S. Appl. No. 11/997,719, dated Jun. 5, 2014, 14 pages.
Notice of Allowance in U.S. Appl. No. 13/083,338, dated Jul. 10, 2014, 22 pages.
Notice of Allowance in U.S. Appl. No. 13/624,278, dated Jun. 25, 2014, 57 pages.
Office Action in CA App. Ser. No. 2771403, dated Jul. 16, 2014, 3 pages.
Office Action in EP App. Ser. No. 03791389.4, dated Jun. 10, 2014, 4 pages.
Office Action in EP App. Ser. No. 08846814.5, dated Jun. 4, 2014, 4 pages.
Office Action in MX App. Ser. No. MX/a/2010/008187, dated Apr. 28, 2014, 4 pages (with English translation).
Office Action in MX App. Ser. No. MX/a/2012/002011, dated Apr. 28, 2014, 10 pages (with English translation).
Office Action in RU App. Ser. No. 2012103471, dated May 20, 2014, 5 pages (with English translation).
Office Action in U.S. Appl. No. 11/662,425, dated Jun. 5, 2014, 30 pages.
Office Action in U.S. Appl. No. 12/039,381, dated May 29, 2014, 78 pages.
Office Action in U.S. Appl. No. 14/002,018, dated Jul. 25, 2014, 14 pages.
Office Action in U.S. Appl. No. 14/002,018, dated Jun. 9, 2014, 19 pages.
Official Notification in EP App. Ser. No. 04807580.8, dated Jun. 16, 2014, 1 pages.
Official Notification in EP App. Ser. No. 04807580.8, dated Jun. 27, 2014, 17 pages.
Request for accelerated examination in KR App. Ser. No. 10-2012-7003846, dated Jun. 18, 2014, 29 pages (with English translation).
Response to Notice of Allowance in U.S. Appl. No. 13/205,328, dated Jul. 8, 2014, 7 pages.
Response to Office Action in CA App. Ser. No. 2676796, dated Jun. 27, 2014, 18 pages.
Response to Office Action in CN App. Ser. No. 201180030568.2 filed on May 14, 2014, 10 pages (with English translation).
Response to Office Action in CN App. Ser. No. 201280010427.9, dated Jun. 12, 2014, 13 pages (with English translation).
Response to Office Action in EP App. Ser. No. 08846814.5, dated Jul. 24, 2014, 71 pages.
Response to Office Action in MX App. Ser. No. MX/a/2010/008187, dated Jun. 25, 2014, 5 pages (with English translation).
Response to Office Action in MX App. Ser. No. MX/a/2012/014776, dated Jun. 20, 2014, 16 pages (with English translation).
Response to Office Action in RU App. Ser. No. 2012103471, dated Jul. 21, 2014, 7 pages (with English translation).
Response to Office Action in U.S. Appl. No. 11/662,425, filed on May 20, 2014, 8 pages.
Response to Office Action in U.S. Appl. No. 14/002,018, filed on May 28, 2014, 7 pages.
Schlumberger et al., "A phase 3, multicenter, double-blind, placebo-controlled trial of lenvatinib (E7080) in patients with 131I-refractory

(56) References Cited

OTHER PUBLICATIONS differentiated thyroid cancer (SELECT)," Am Soc Clin Oncol., Annual Meeting Abstract LBA6008, 2012, 4 pages.
Shirai, Y., et al., ""Role of low-substituted hydroxypropylcellulose in dissociation and bioavalability of novel fine granule system for masking bitter taste,"" Biol. Pharm. Bull, 17(3): 427-431 (1994).
Submission Documents re RCE filed in U.S. Appl. No. 12/524,754, dated May 13, 2014, 1 page.
Submission in EP App. Ser. No. 04807580.8, dated Jun. 13, 2014, 18 pages.
Vergote et al., "Prognostic and prediction role of circulating angiopoietin-2 in multiple solid tumors: an analysis of approximately 500 patients treated with lenvatinib across tumor types," Am Soc Clin Oncol Annual Meeting Abstract, May 31, 2014, abstract 11061, 3 pages.
Wang et al., "KRAS, BRAF, PIK3CA mutations and Pten Expression in Human Colorectal Cancer-Relationship with Metastatic Colorectal Cancer," Ann Oncol., 2010, 21(Supp 6):V164.
Yokota, "ASCO report: Gastrointestinal Cancer field/ASCO Hokoku Shokakigan Ryoiki," Gan Bunshi Hyoteki Chiryo, 2010, 8(4):271-283.

* cited by examiner

ANTITUMOR AGENT USING COMPOUNDS HAVING KINASE INHIBITORY EFFECT IN COMBINATION

TECHNICAL FIELD

The present invention relates to an antitumor agent for combined use of compounds having a kinase inhibitory effect. Particularly, the present invention relates to an antitumor agent for combined use of a compound having a HGFR inhibitory effect and a compound having a multi-tyrosine kinase inhibitory effect.

BACKGROUND ART

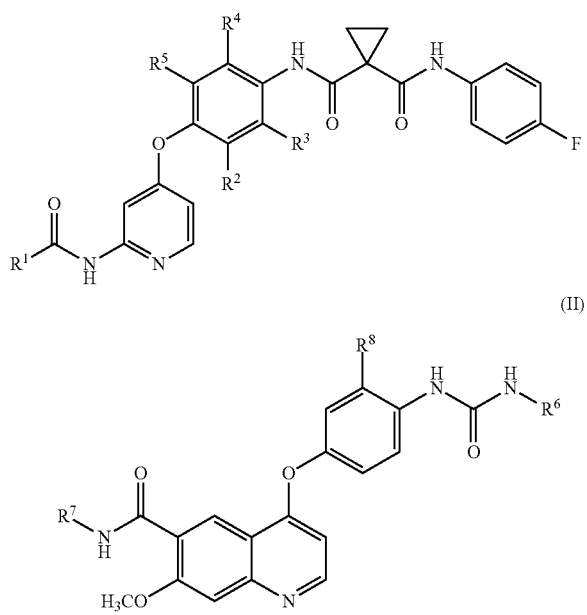

wherein $R^1$ is azetidinyl and the like, $R^2$ to $R^5$ is a hydrogen atom or a halogen atom, $R^6$ is $C_{3-8}$ cycloalkyl and the like, $R^7$ is a hydrogen atom and the like, and $R^8$ is a halogen atom and the like.

The compound represented by Formula (I) has potent inhibitory effects against hepatocyte growth factor receptor (HGFR), and thus is useful as an antitumor agent, an angiogenesis inhibitor, and a tumor metastasis inhibitor (Patent Literature 1). HGFR is known to be overexpressed in a large number of tumor cells (Non Patent Literature 1) and involved in malignant alteration of tumors. Further, HGFR is also expressed in vascular endothelial cells, and is considered to cause the proliferation of tumors by promoting angiogenesis (Non Patent Literature 2).

On the other hand, the compound represented by Formula (II) has anti-angiogenic actions (Patent Literature 2), inhibitory effects (Patent Literatures 3 to 6) against tyrosine kinases which are reported to be involved in malignant alteration of tumors (Non-Patent Literatures 3 to 5), and the like; and is known as a therapeutic agent for various tumors such as thyroid cancer, lung cancer, melanoma, endometrial cancer, gastric cancer and bladder cancer.

In general, antitumor agents are often not effective for all of the patients when they were used individually. Thus, attempts have been made so far to increase the cure rate by combination of plural antitumor agents (Patent Literatures 7 to 9).

CITATION LIST

Patent Literature

Patent Literature 1: WO 2007/023768
Patent Literature 2: WO 2002/032872
Patent Literature 3: WO 2004/080462
Patent Literature 4: WO 2007/061130
Patent Literature 5: WO 2007/136103
Patent Literature 6: WO 2008/026748
Patent Literature 7: WO 2009/140549
Patent Literature 8: US Patent Application Publication No. 2004-259834
Patent Literature 9: U.S. Pat. No. 6,217,866

Non Patent Literature

Non Patent Literature 1: Oncology Reports, 5, 1013-1024, 1998.
Non Patent Literature 2: Advances in Cancer Research, 67, 257-279, 1995.
Non Patent Literature 3: Current Cancer Drug Targets, 6, 65-75, 2006.
Non Patent Literature 4: Nature Reviews, Cancer, 10, 116-129, 2010.
Non Patent Literature 5: Clinical Cancer Research, 15, 7119-7123, 2009.

SUMMARY OF INVENTION

Technical Problem

However, the therapeutic effects, which have been reported so far, obtained by combination of plural antitumor agents were insufficient, and hence development of a novel combination therapy using antitumor agents has been expected.

Solution to Problem

In view of such circumstances, the present inventors intensively studied to discover that administration of a combination of the compounds represented by Formula (I) and Formula (II) to a patient suffering from a tumor attains an unexpectedly excellent antitumor effect, thereby completing the present invention.

That is, the present invention provides [1] to [8] below.

[1] An antitumor agent for combined use of:

a compound or pharmaceutically acceptable salt thereof represented by Formula (I):

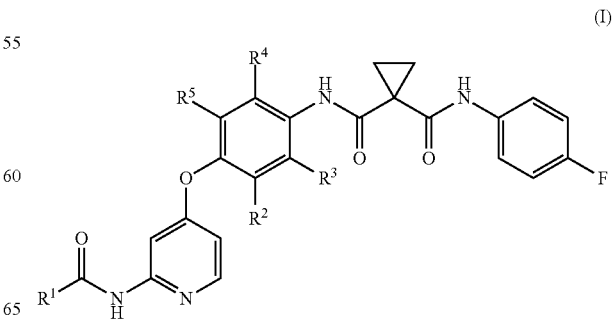

wherein R¹ is azetidinyl, piperidinyl, or a formula —NR$^{11a}$R$^{11b}$, each of which optionally have a substituent selected from Substituent group A, wherein R$^{11a}$ and R$^{11b}$ are the same or different and each is a hydrogen atom, $C_{1-6}$ alkyl, or piperidinyl optionally having $C_{1-6}$ alkyl, Substituent group A consists of hydroxyl, piperazinyl optionally having methyl, and azetidinyl optionally having dimethylamino, and R² to R⁵ are the same or different and each is a hydrogen atom or a fluorine atom; and a compound or pharmaceutically acceptable salt thereof represented by Formula (II):

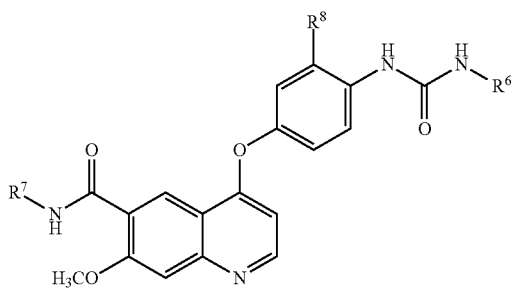

(II)

wherein R⁶ is $C_{1-6}$ alkyl or $C_{3-8}$ cycloalkyl,

R⁷ is a hydrogen atom, $C_{1-6}$ alkyl, or $C_{1-6}$ alkoxy, and

R⁸ is a hydrogen atom or a halogen atom.

[2] An antitumor agent for simultaneous or separate administration of a compound or pharmaceutically acceptable salt thereof represented by the above Formula (I), and a compound or pharmaceutically acceptable salt thereof represented by the above Formula (II).

[3] An antitumor agent comprising a compound or pharmaceutically acceptable salt thereof represented by the above Formula (I), and a compound or pharmaceutically acceptable salt thereof represented by the Formula (II).

[4] A compound or pharmaceutically acceptable salt thereof represented by the Formula (II) for therapy of a tumor by combined use with a compound or pharmaceutically acceptable salt thereof represented by the above Formula (I).

[5] A compound or pharmaceutically acceptable salt thereof represented by the Formula (I) for therapy of a tumor by combined use with a compound or pharmaceutically acceptable salt thereof represented by the above Formula (II).

[6] A method of treating a tumor, wherein a compound or pharmaceutically acceptable salt thereof represented by the above Formula (I), and a compound or pharmaceutically acceptable salt thereof represented by the Formula (II) are used in combination.

[7] A pharmaceutical composition comprising a compound or pharmaceutically acceptable salt thereof represented by the above Formula (I), a compound or pharmaceutically acceptable salt thereof represented by the Formula (II), and a vehicle.

[8] A kit comprising:

a pharmaceutical composition comprising a compound or pharmaceutically acceptable salt thereof represented by the above Formula (I) and a vehicle; and a pharmaceutical composition comprising a compound or pharmaceutically acceptable salt thereof represented by the Formula (II), and a vehicle.

The compound represented by the above Formula (I) is preferably one or more compounds selected from the group consisting of N-(2-fluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxamide:

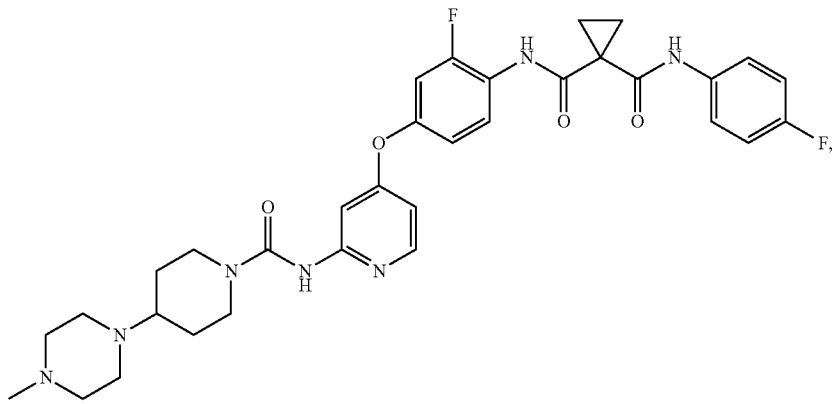 [SMILES: CN1CCN(C2CCN(C(=O)Nc3cc(Oc4ccc(NC(=O)C5(C(=O)Nc6ccc(F)cc6)CC5)c(F)c4)ccn3)CC2)CC1]

N-[4-({2-[({4-[3-(dimethylamino)azetidin-1-yl]piperidin-1-yl}carbonyl)amino)pyridin-4-yl}oxy)-2-fluorophenyl]-N'-(4-fluorophenyl)cyclopropane-1,1-dicarboxamide:

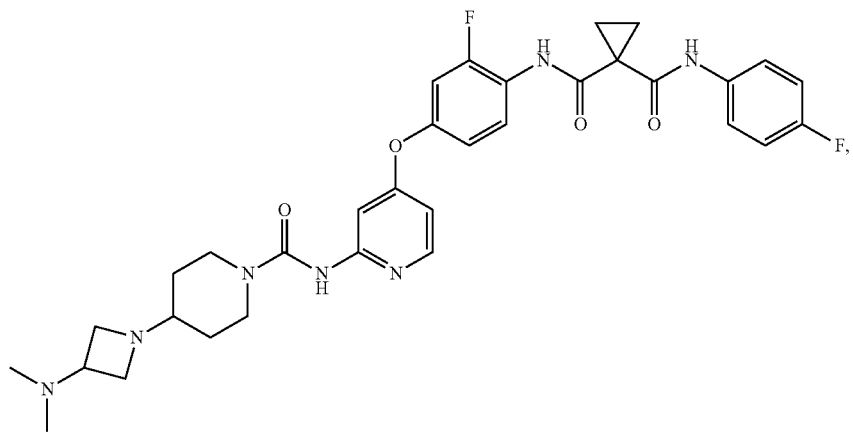 [SMILES: CN(C)C1CN(C2CCN(C(=O)Nc3cc(Oc4ccc(NC(=O)C5(C(=O)Nc6ccc(F)cc6)CC5)c(F)c4)ccn3)CC2)C1]

N-{2,5-difluoro-4-[(2-{[(3-hydroxyazetidin-1-yl)carbonyl]amino}pyridin-4-yl)oxy]phenyl}-N'-(4-fluorophenyl)cyclopropane-1,1-dicarboxamide:

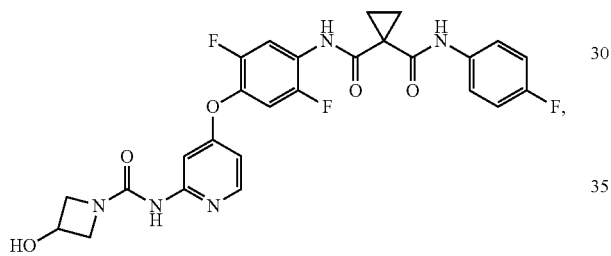

N-{2,5-difluoro-4-[(2-{[4-(4-methylpiperazin-1-yl)piperidin-1-yl]carbonyl}amino)pyridin-4-yl]oxy}phenyl)-N'-(4-fluorophenyl)cyclopropane-1,1-dicarboxamide:

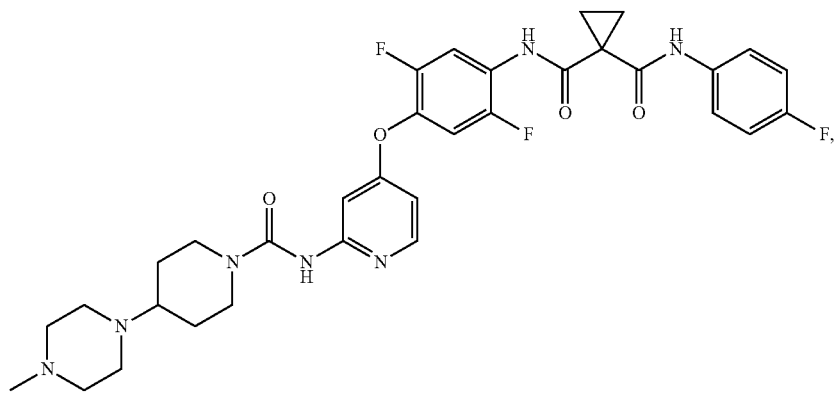 [SMILES: CN1CCN(C2CCN(C(=O)Nc3cc(Oc4cc(F)c(NC(=O)C5(C(=O)Nc6ccc(F)cc6)CC5)cc4F)ccn3)CC2)CC1]

and
N-(2,5-difluoro-4-{[2-({[methyl(1-methylpiperidin-4-yl)amino]carbonyl}amino)pyridin-4-yl]oxy}phenyl)-N'-(4-fluorophenyl)cyclopropane-1,1-dicarboxamide:

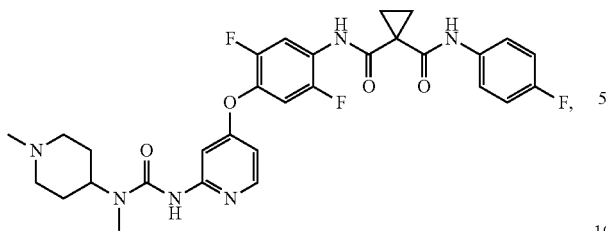
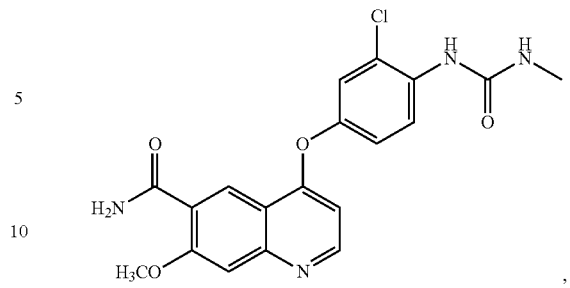

and more preferably
N-(2-fluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxamide:

4-[3-chloro-4-(ethylaminocarbonyl)aminophenoxy]-7-methoxy-6-quinolinecarboxamide:

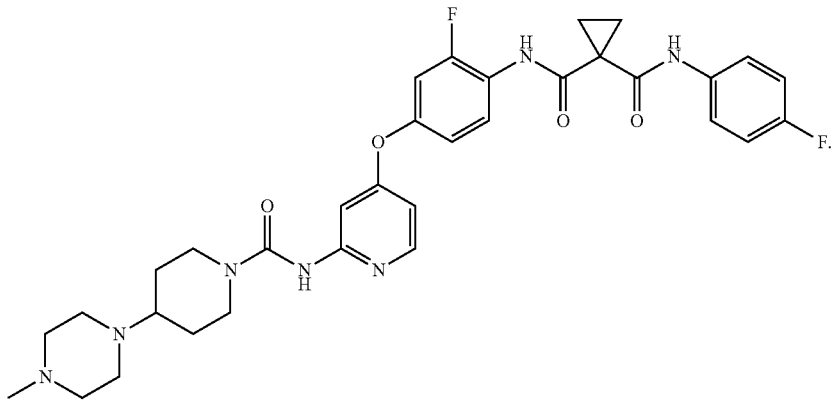 [SMILES: CN1CCN(C2CCN(C(=O)Nc3cc(Oc4ccc(NC(=O)C5(C(=O)Nc6ccc(F)cc6)CC5)c(F)c4)ccn3)CC2)CC1]

The compound represented by the above Formula (II) is preferably one or more compounds selected from the group consisting of
4-[3-chloro-4-(cyclopropylaminocarbonyl)aminophenoxy]-7-methoxy-6-quinolinecarboxamide:

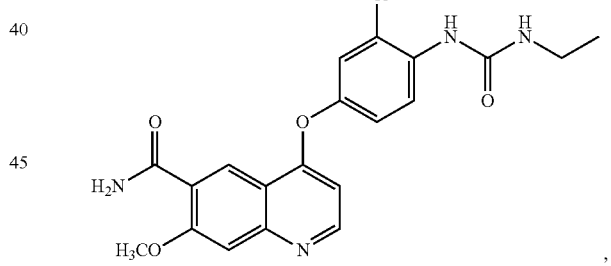

N6-methoxy-4-(3-chloro-4-{[(cyclopropylamino)carbonyl)amino]phenoxy}-7-methoxy-6-quinolinecarboxamide:

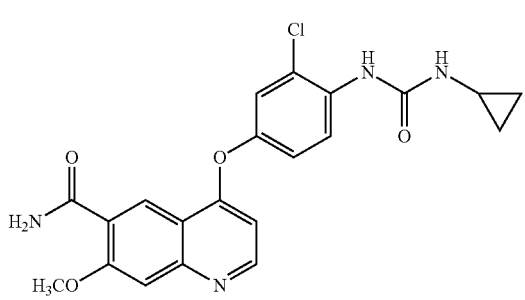 [SMILES: CCNC(=O)Nc1ccc(Oc2ccnc3cc(OC)c(C(N)=O)cc23)cc1Cl]

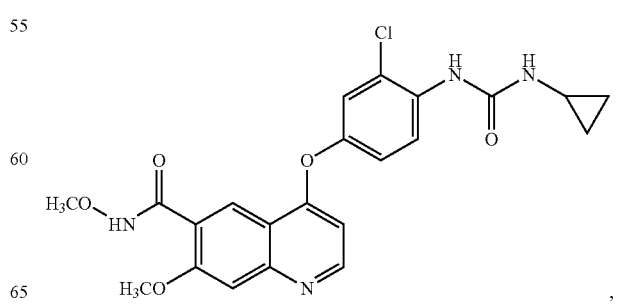

4-[3-chloro-4-(methylaminocarbonyl)aminophenoxy]-7-methoxy-6-quinolinecarboxamide:

and
N6-methoxy-4-(3-chloro-4-{[(ethylamino)carbonyl]
amino}phenoxy)-7-methoxy-6-quinolinecarboxamide:

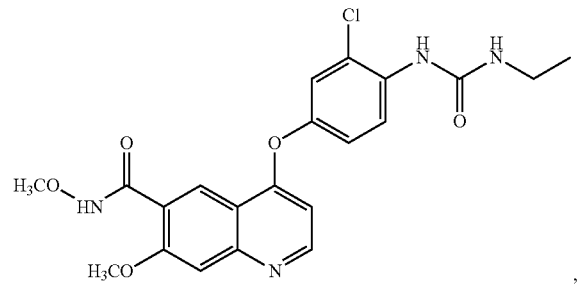 [SMILES: CCNC(=O)Nc1ccc(Oc2ccnc3cc(OC)c(C(=O)NOC)cc23)cc1Cl]

and more preferably
4-[3-chloro-4-(cyclopropylaminocarbonyl)aminophenoxy]-
7-methoxy-6-quinolinecarboxamide:

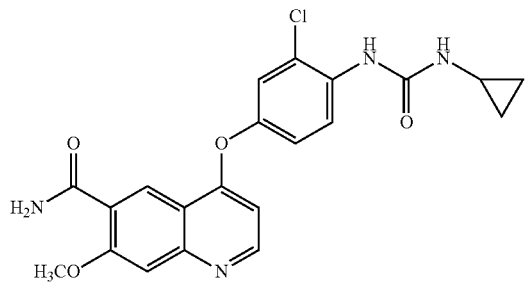

Advantageous Effects of Invention

The present invention provides an antitumor agent for combined use of a compound having a HGFR inhibitory effect and a compound having a multi-tyrosine kinase inhibitory effect. Such an antitumor agent exhibits an excellent antitumor effect compared to cases where these are individually used, and exhibits antitumor effects against various cancer types.

DESCRIPTION OF EMBODIMENTS

Figure 1:
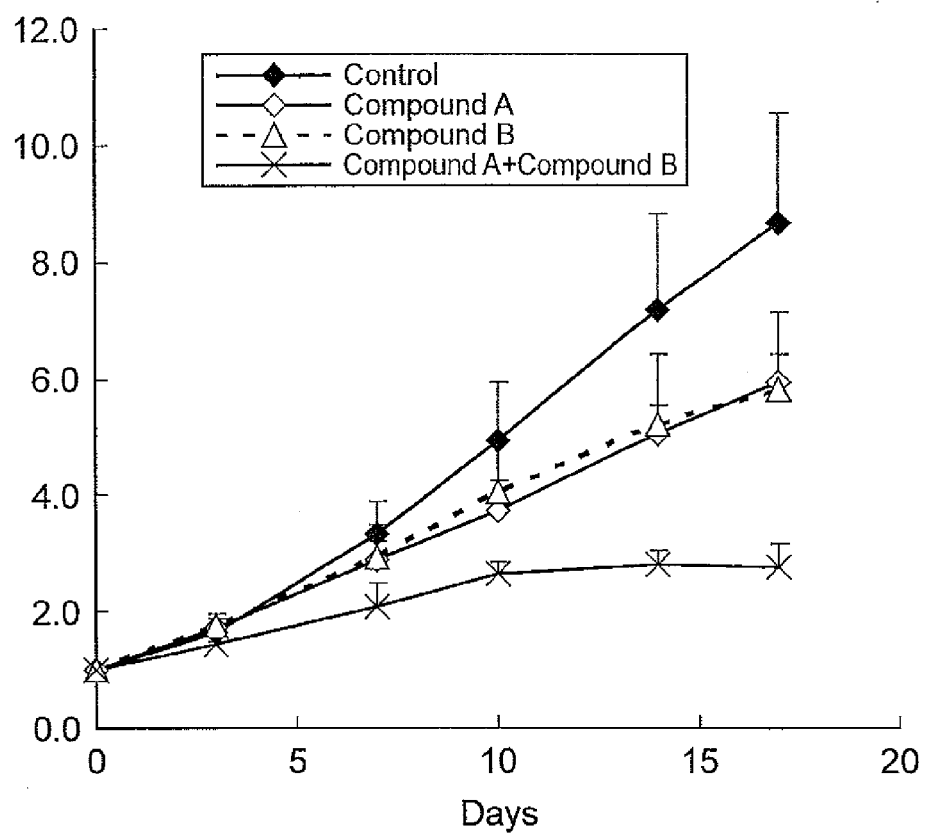
FIG. 1 is a graph showing a combined effect of Compound A and Compound B in a model animal to which human malignant melanoma cell line (SEKI) was transplanted.

The compound or pharmaceutically acceptable salt thereof represented by Formula (I) according to the present invention can be produced by the method described in Patent Literature 1. Further, the compound or pharmaceutically acceptable salt thereof represented by Formula (II) according to the present invention can be produced by the method described in Patent Literature 2.

Examples of the pharmaceutically acceptable salt include salts with inorganic acids, salts with organic acids, salts with inorganic bases, salts with organic bases, and salts with acidic or basic amino acids.

Preferred examples of the salts with inorganic acids include salts with hydrochloric acid, hydrobromic acid, sulfuric acid, nitric acid, phosphoric acid and the like. Preferred examples of the salts with organic acids include salts with acetic acid, succinic acid, fumaric acid, maleic acid, tartaric acid, citric acid, lactic acid, stearic acid, benzoic acid, methanesulfonic acid, ethanesulfonic acid, p-toluenesulfonic acid and the like.

Preferred examples of the salts with inorganic bases include alkaline metal salts such as a sodium salt and a potassium salt; alkaline earth metal salts such as a calcium salt and a magnesium salt; an aluminum salt; and an ammonium salt. Preferred examples of the salts with organic bases include salts with diethylamine, diethanolamine, meglumine, N,N-dibenzylethylenediamine and the like.

Preferred examples of the salts with acidic amino acids include salts with aspartic acid, glutamic acid and the like. Preferred examples of the salts with basic amino acids include salts with arginine, lysine, ornithine and the like.

Especially preferred pharmaceutically acceptable salts are salts with organic acids.

The antitumor agent of the present invention may be orally administered in the form of a solid formulation such as a tablet, granule, fine granule, powder or capsule, or in the form of a liquid, jelly, syrup or the like.

Further, the antitumor agent of the present invention may be parenterally administered in the form of an injection, suppository, ointment, cataplasm or the like.

The dose of the compound or pharmaceutically acceptable salt thereof represented by Formula (I) may be appropriately selected depending on the degrees of symptoms, age, sex and body weight of the patient, difference in sensitivity, route, time and interval of administration, type of pharmaceutical formulation, and/or the like. Usually, in cases where oral administration is carried out for an adult (60 kg body weight), the dose is 10 to 6000 mg, preferably 50 to 4000 mg per day. This may be administered at one time, or dividedly at 2 or 3 times per day.

The dose of the compound or pharmaceutically acceptable salt thereof represented by Formula (II) may be appropriately selected as in the case described above. Usually, in cases where oral administration is carried out for an adult (60 kg body weight), the dose is 1 to 600 mg, preferably 4 to 400 mg, more preferably 4 to 200 mg per day. This may be administered at one time, or dividedly at 2 or 3 times per day.

In cases where an oral solid formulation is prepared, a vehicle, and, as required, a binder, disintegrator, lubricant, coloring agent, flavoring agent and/or the like may be added to the principal component, that is, a compound or pharmaceutically acceptable salt thereof represented by Formula (I), and a compound or pharmaceutically acceptable salt thereof represented by Formula (II), to prepare, thereafter, a tablet, granule, fine granule, powder, capsule or the like according to a conventional method.

Examples of the vehicle include lactose, corn starch, white soft sugar, glucose, sorbitol, crystalline cellulose and silicon dioxide. Examples of the binder include polyvinyl alcohol, ethylcellulose, methylcellulose, gum Arabic, hydroxypropylcellulose and hydroxypropylmethylcellulose. Examples of the lubricant include magnesium stearate, talc and silica. Examples of the coloring agent include titanium oxide, iron sesquioxide, yellow iron sesquioxide, cochineal, carmine and riboflavin. Examples of the flavoring agent include cocoa powder, ascorbic acid, tartaric acid, peppermint oil, borneol and cinnamon powder. These tablets and granules may be coated as required.

In cases where an injection is prepared, a pH adjustor, buffering agent, suspending agent, solubilizer, stabilizer, isotonic agent, preservative and/or the like may be added as required to the principal component, to prepare an intravenous, subcutaneous or intramuscular injection, or an intravenous drip infusion. As required, these may be prepared into lyophilized products by conventional methods.

Examples of the suspending agent include methylcellulose, polysorbate 80, hydroxyethylcellulose, gum Arabic, powdered tragacanth, sodium carboxymethylcellulose and polyoxyethylene sorbitan monolaurate.

Examples of the solubilizer include polyoxyethylene hydrogenated castor oil, polysorbate 80, nicotinamide, polyoxyethylene sorbitan monolaurate, macrogol and glycerin fatty acid ester.

Examples of the stabilizer include sodium sulfite and sodium metabisulfite. Examples of the preservative include methyl parahydroxybenzoate, ethyl parahydroxybenzoate, sorbic acid, phenol, cresol and chlorocresol.

The antitumor agent of the present invention may be prepared by formulating a compound or pharmaceutically acceptable salt thereof represented by Formula (I), and a compound or pharmaceutically acceptable salt thereof represented by Formula (II) separately, and the both may be administered either at the same time or separately. Further, the two formulations may be placed in a single package, to provide the so called kit formulation. Further, the both compounds may be contained in a single formulation.

The type of the tumor to be treated with the antitumor agent of the present invention is not restricted, and examples thereof include fibroma, adipoma, myxoma, chondroma, osteoma, angioma, lymphoma, myeloma, melanoma, myoma, neuroma, glioma, osteosarcoma, myosarcoma, fibrosarcoma, papilloma, adenoma, brain tumor, and cancers such as cervical cancer, esophagus cancer, tongue cancer, lung cancer, breast cancer, pancreatic cancer, gastric cancer, small intestinal cancer in duodenum, jejunum, ileum and the like, large bowel cancer in colon, caecum, rectum and the like, bladder cancer, renal cancer, liver cancer, gallbladder cancer, prostate cancer, uterine cancer, ovarian cancer, thyroid cancer and pharyngeal cancer; and mixed tumors thereof.

EXAMPLES

The present invention is described in more detail by way of Examples below.
[List of Abbreviations]
FBS: Fetal bovine serum
EDTA: Ethylene diamine tetra acetic acid
TV: Tumor volume
RTV: Relative tumor volume
Compound A: 4-(3-chloro-4-(cyclopropylaminocarbonyl) aminophenoxy)-7-methoxy-6-quinolinecarboxamide mesylate
Compound B: N-(2-fluoro-4-{[2-({[4-(4-methylpiperazin-1-yl)piperidin-1-yl]carbonyl}amino)pyridin-4-yl] oxy}phenyl)-N'-(4-fluorophenyl)cyclopropane-1,1-dicarboxamide tartrate Example 1

A Combined Effect of Compound A and Compound B in a Model Animal to which Human Malignant Melanoma Cell Line (SEKI) was Transplanted The human malignant melanoma cell line SEKI (JCRB Cell bank) was cultured using a 10% FBS-containing RPM 1640 medium (SIGMA) in a 5% $CO_2$ incubator under the condition of 37° C. When the cells reached a state of approximately 80% confluency, the cells were collected using trypsin-EDTA. To these cells, a Hanks' Balanced Salt Solution containing 50% Matrigel was added to prepare a suspension at $5.0 \times 10^7$ cells/mL. The cell suspension thus obtained was subcutaneously transplanted at the lateral side of the body of a nude mouse (CAnN.Cg-Foxn1nu/CrlCrlj, Charles River Laboratories Japan, Inc.) in an amount of 0.1 mL, where each group contained six mice. From 11 days after the transplantation, Compound A (10 mg/kg, once daily, for 17 days) and Compound B (100 mg/kg, once daily, for 17 days) were orally administered, either individually or both in a row.

Setting the initial day of administration at Day 0, the major axis and the minor axis of a tumor developed in each mouse were measured using Digimatic caliper (Mitsutoyo Corporation) thereafter on Day 3, 7, 10, 14, and 17.

The tumor volume and the relative tumor volume were calculated according to the equations below.

TV=major axis (mm)×minor axis$^2$ (mm$^2$)/2

RTV=TV on the day of measurement/TV on the initial day of administration

The results of RTV were summarized in Table 1 and FIG. 1. The numbers in the Table indicate an average value±standard deviation (the same will apply to the following Tables). Compared to cases where Compound A and Compound B were each administered individually, the combined use of Compound A and Compound B exhibited a remarkably excellent antitumor effect. Also, as a result of performing two-way ANOVA with respect to log-transformed RTV by setting Compound A and Compound B as the factors, RTV on Day 17 was found to be statistically significant ($p<0.05$), whereby the synergistic effect of Compound A and Compound B was confirmed.

TABLE 1

|  | Day 3 | Day 7 | Day 10 |
| --- | --- | --- | --- |
| Control group | 1.63 ± 0.10 | 3.35 ± 0.56 | 4.95 ± 1.00 |
| Compound A group | 1.71 ± 0.19 | 2.88 ± 0.35 | 3.74 ± 0.53 |
| Compound B group | 1.76 ± 0.22 | 2.93 ± 0.57 | 4.06 ± 0.85 |
| Combination group of Compound A and Compound B | 1.43 ± 0.06 | 2.10 ± 0.38 | 2.66 ± 0.19 |

|  | Day 14 | Day 17 |
| --- | --- | --- |
| Control group | 7.18 ± 1.66 | 8.65 ± 1.89 |
| Compound A group | 5.06 ± 0.49 | 5.92 ± 0.50 |
| Compound B group | 5.23 ± 0.20 | 5.80 ± 1.35 |
| Combination group of Compound A and Compound B | 2.80 ± 0.27 | 2.77 ± 0.38 |

Example 2

A Combined Effect of Compound A and Compound B in a Model Animal to which Human Pancreatic Cancer Cell Line (KP-4) was Transplanted The human pancreatic cancer cell line KP-4 (acquired from National Hospital Organization Kyushu Cancer Center) was cultured using a 10% FBS-containing RPMI 1640 medium (SIGMA) in a 5% $CO_2$ incubator under the condition of 37° C. When the cells reached a state of approximately 80% confluency, the cells were collected using trypsin-EDTA. To these cells, a Hanks' Balanced Salt Solution containing 50% Matrigel was added to prepare a suspension at $5.0 \times 10^7$ cells/mL. The cell suspension thus obtained was subcutaneously transplanted at the lateral side of the body of a nude mouse (CAnN.Cg-Foxn1nu/CrlCrlj, Charles River Laboratories Japan, Inc.) in an amount of 0.1 mL, where each group contained six mice. From 11 days after the transplantation, Compound A (10 mg/kg, once daily, for 17 days) and Compound B (100 mg/kg, once daily, for 17 days) were orally administered, either individually or both in a row.

Setting the initial day of administration at Day 0, the major axis and the minor axis of a tumor developed in each mouse were measured using Digimatic caliper (Mitsutoyo Corporation) thereafter on Day 3, 7, 10, 14, and 17.

The tumor volume and the relative tumor volume were calculated according to the equations below.

TV=major axis (mm)×minor axis$^2$ (mm$^2$)/2

RTV=TV on the day of measurement/TV on the initial day of administration

Figure 2:
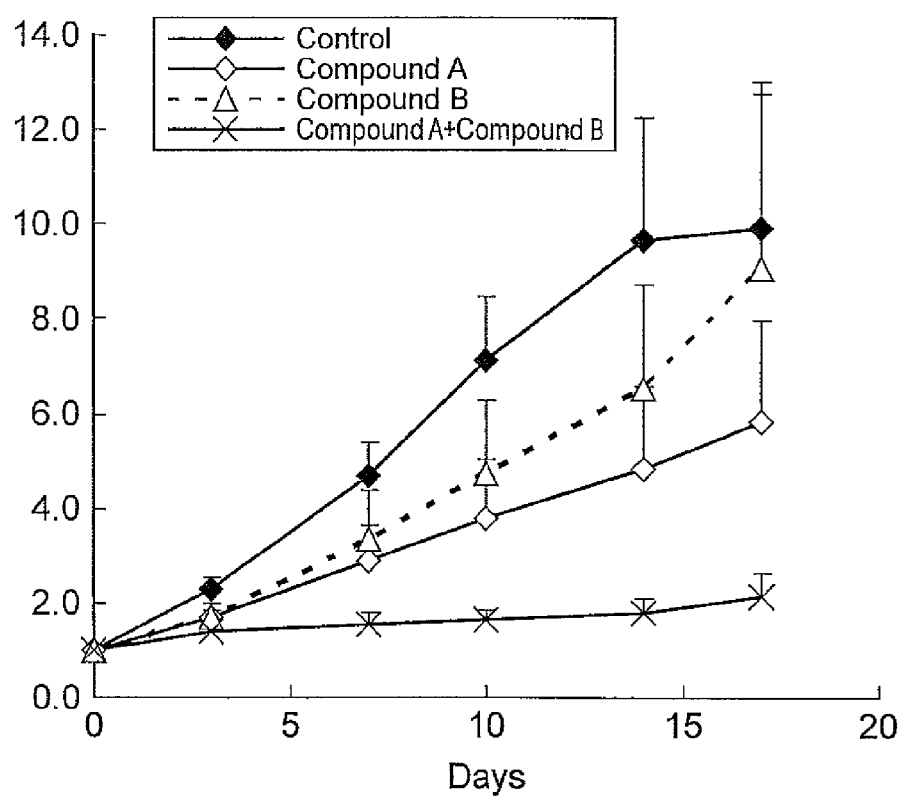
FIG. 2 is a graph showing a combined effect of Compound A and Compound B in a model animal to which human pancreatic cancer cell line (KP-4) was transplanted.

The results of RTV were summarized in Table 2 and FIG. 2. Compared to cases where Compound A and Compound B were each administered individually, the combined use of Compound A and Compound B exhibited a remarkably excellent antitumor effect. Also, as a result of performing two-way ANOVA with respect to log-transformed RTV by setting Compound A and Compound B as the factors, RTV on Day 17 was found to be statistically significant (p<0.05), whereby the synergistic effect of Compound A and Compound B was confirmed.

TABLE 2

|  | Day 3 | Day 7 | Day 10 |
| --- | --- | --- | --- |
| Control group | 2.27 ± 0.25 | 4.68 ± 0.70 | 7.12 ± 1.35 |
| Compound A group | 1.67 ± 0.16 | 2.89 ± 0.74 | 3.77 ± 1.26 |
| Compound B group | 1.71 ± 0.26 | 3.33 ± 1.06 | 4.72 ± 1.55 |
| Combination group of Compound A and Compound B | 1.40 ± 0.14 | 1.54 ± 0.24 | 1.64 ± 0.23 |

|  | Day 14 | Day 17 |
| --- | --- | --- |
| Control group | 9.65 ± 2.61 | 9.92 ± 3.07 |
| Compound A group | 4.83 ± 1.75 | 5.81 ± 2.17 |
| Compound B group | 6.53 ± 2.19 | 9.05 ± 3.71 |
| Combination group of Compound A and Compound B | 1.79 ± 0.32 | 2.13 ± 0.52 |

Example 3

A Combined Effect of Compound A and Compound B in a Model Animal to Which Human Gastric Cancer Cell Line (IM95m) was Transplanted The human gastric cancer cell line IM95m (Health Science Research Resources Bank) was cultured using a DMEM medium (Wako Pure Chemical Industries, Ltd) containing 4500 mg/mL glucose, 10% FBS, and 10 μg/mL insulin in a 5% $CO_2$ incubator under the condition of 37° C. When the cells reached a state of approximately 80% confluency, the cells were collected using trypsin-EDTA. To these cells, a Hanks' Balanced Salt Solution containing 50% Matrigel was added to prepare a suspension at $1.0 \times 10^8$ cells/mL. The cell suspension thus obtained was subcutaneously transplanted at the lateral side of the body of a nude mouse (CAnN.Cg-Foxn1nu/CrlCrlj, Charles River Laboratories Japan, Inc.) in an amount of 0.1 mL, where each group contained six mice. From 13 days after the transplantation, Compound A (10 mg/kg, once daily, for 21 days) and Compound B (100 mg/kg, once daily, for 21 days) were orally administered continuously, either individually or both in a row.

Setting the initial day of administration at Day 0, the major axis and the minor axis of a tumor developed in each mouse were measured using Digimatic caliper (Mitsutoyo Corporation) thereafter on Day 4, 7, 11, 14, 18 and 21.

The tumor volume and the relative tumor volume were calculated according to the equations below.

TV=major axis (mm)×minor axis$^2$ (mm$^2$)/2

RTV=TV on the day of measurement/TV on the initial day of administration

Figure 3:
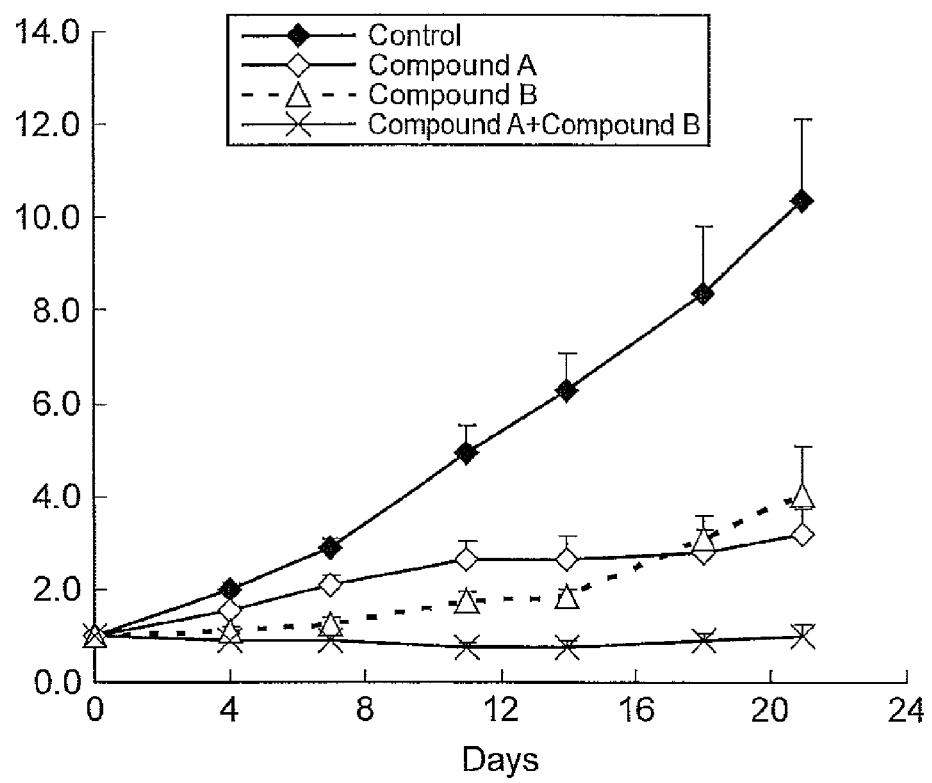
FIG. 3 is a graph showing a combined effect of Compound A and Compound B in a model animal to which human gastric cancer cell line (IM95m) was transplanted.

The results of RTV were summarized in Table 3 and FIG. 3. Compared to cases where Compound A and Compound B were each administered individually, the combined use of Compound A and Compound B exhibited a remarkably excellent antitumor effect. Although no statistical significance was shown by two-way ANOVA, an effect of complete inhibition of tumor proliferation was confirmed by the combined use of Compound A and Compound B.

TABLE 3

|  | Day 4 | Day 7 | Day 11 |
| --- | --- | --- | --- |
| Control group | 1.97 ± 0.16 | 2.87 ± 0.20 | 4.91 ± 0.64 |
| Compound A group | 1.53 ± 0.12 | 2.10 ± 0.18 | 2.65 ± 0.37 |
| Compound B group | 1.12 ± 0.08 | 1.24 ± 0.15 | 1.75 ± 0.17 |
| Combination group of Compound A and Compound B | 0.92 ± 0.12 | 0.89 ± 0.22 | 0.76 ± 0.09 |

|  | Day 14 | Day 18 | Day 21 |
| --- | --- | --- | --- |
| Control group | 6.27 ± 0.83 | 8.38 ± 1.41 | 10.36 ± 1.74 |
| Compound A group | 2.65 ± 0.49 | 2.80 ± 0.47 | 3.18 ± 0.57 |
| Compound B group | 1.85 ± 0.16 | 3.09 ± 0.48 | 4.02 ± 1.05 |
| Combination group of Compound A and Compound B | 0.73 ± 0.15 | 0.91 ± 0.14 | 1.00 ± 0.25 |

Example 4

A Combined Effect of Compound A and Compound B in a Model Animal to Which Human Ovarian Cancer Cell Line (A2780) was Transplanted The human ovarian cancer cell line A2780 (ATCC) was cultured using a 10% FBS-containing RPMI 1640 medium (SIGMA) in a 5% $CO_2$ incubator under the condition of 37° C. When the cells reached a state of approximately 80% confluency, the cells were collected using trypsin-EDTA. To these cells, a Hanks' Balanced Salt Solution containing 50% Matrigel was added to prepare a suspension at a concentration of $5.0 \times 10^7$ cells/mL. The cell suspension thus obtained was subcutaneously transplanted at the lateral side of the body of a nude mouse (CAnN.Cg-Foxn1nu/CrlCrlj, Charles River Laboratories Japan, Inc.) in an amount of 0.1 mL, where each group contained six mice. Compound A (10 mg/kg, once daily, for 10 days) and Compound B (100 mg/kg, once daily, for 10 days) were orally administered, either individually or both in a row.

Setting the initial day of administration at Day 0, the major axis and the minor axis of a tumor developed in each mouse were measured using Digimatic caliper (Mitsutoyo Corporation) thereafter on Day 3, 5, 8, and 10.

The tumor volume and the relative tumor volume were calculated according to the equations below.

TV=major axis (mm)×minor axis$^2$ (mm$^2$)/2

RTV=TV on the day of measurement/TV on the initial day of administration

Figure 4:
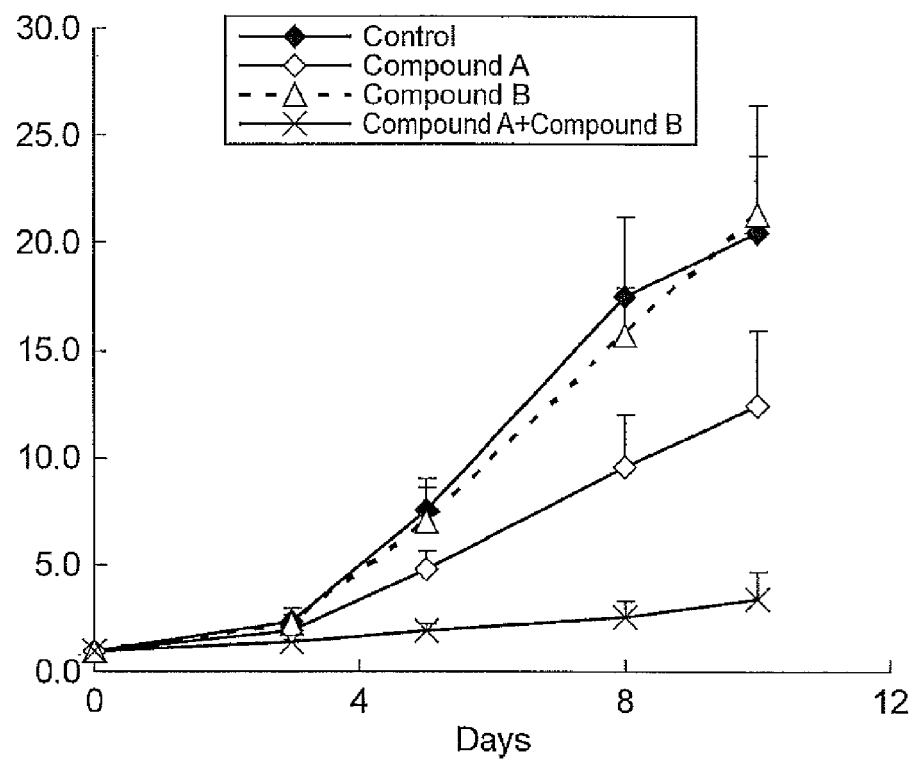
FIG. 4 is a graph showing a combined effect of Compound A and Compound B in a model animal to which human ovarian cancer cell line (A2780) was transplanted.

The results of RTV were summarized in Table 4 and FIG. 4. Compared to cases where Compound A and Compound B were each administered individually, the combined use of Compound A and Compound B exhibited a remarkably excellent antitumor effect. Also, as a result of performing two-way ANOVA with respect to log-transformed RTV by setting Compound A and Compound B as the factors, RTV on Day 10 was found to be statistically significant ($p<0.05$), whereby the synergistic effect of Compound A and Compound B was confirmed.

TABLE 4

|  | Day 3 | Day 5 |
|---|---|---|
| Control group | 2.37 ± 0.60 | 7.52 ± 1.45 |
| Compound A group | 1.92 ± 0.17 | 4.77 ± 0.85 |
| Compound B group | 2.23 ± 0.42 | 7.01 ± 1.54 |
| Combination group of Compound A and Compound B | 1.38 ± 0.12 | 1.95 ± 0.27 |

|  | Day 8 | Day 10 |
|---|---|---|
| Control group | 17.47 ± 3.75 | 20.41 ± 6.02 |
| Compound A group | 9.51 ± 2.44 | 12.37 ± 3.53 |
| Compound B group | 15.70 ± 2.27 | 21.29 ± 2.76 |
| Combination group of Compound A and Compound B | 2.50 ± 0.76 | 3.34 ± 1.30 |

Example 5

A Combined Effect of Compound A and Compound B in a Model Animal to Which Human Glioblastoma Cell Line (U87MG) was Transplanted The human glioblastoma cell line (U87MG) (ATCC) was cultured using a 10% FBS-containing E-MEM medium (SIGMA) in a 5% $CO_2$ incubator under the condition of 37° C. When the cells reached a state of approximately 80% confluency, the cells were collected using trypsin-EDTA. To these cells, a Hanks' Balanced Salt Solution containing 50% Matrigel was added to prepare a suspension at a concentration of $5.0 \times 10^7$ cells/mL. The cell suspension thus obtained was subcutaneously transplanted at the lateral side of the body of a nude mouse (CAnN.Cg-FOXn1nu/CrlCrlj, Charles River Laboratories Japan, Inc.) in an amount of 0.1 mL, where each group contained six mice. Compound A (10 mg/kg, once daily, for 21 days) and Compound B (100 mg/kg, once daily, for 21 days) were orally administered, either individually or both in a row.

Setting the initial day of administration at Day 0, the major axis and the minor axis of a tumor developed in each mouse were measured using Digimatic caliper (Mitsutoyo Corporation) thereafter on Day 2, 5, 7, 9, 12, 14, 16, 19, and 21.

The tumor volume and the relative tumor volume were calculated according to the equations below.

TV=major axis (mm)×minor axis² (mm²)/2

RTV=TV on the day of measurement/TV on the initial day of administration

Figure 5:
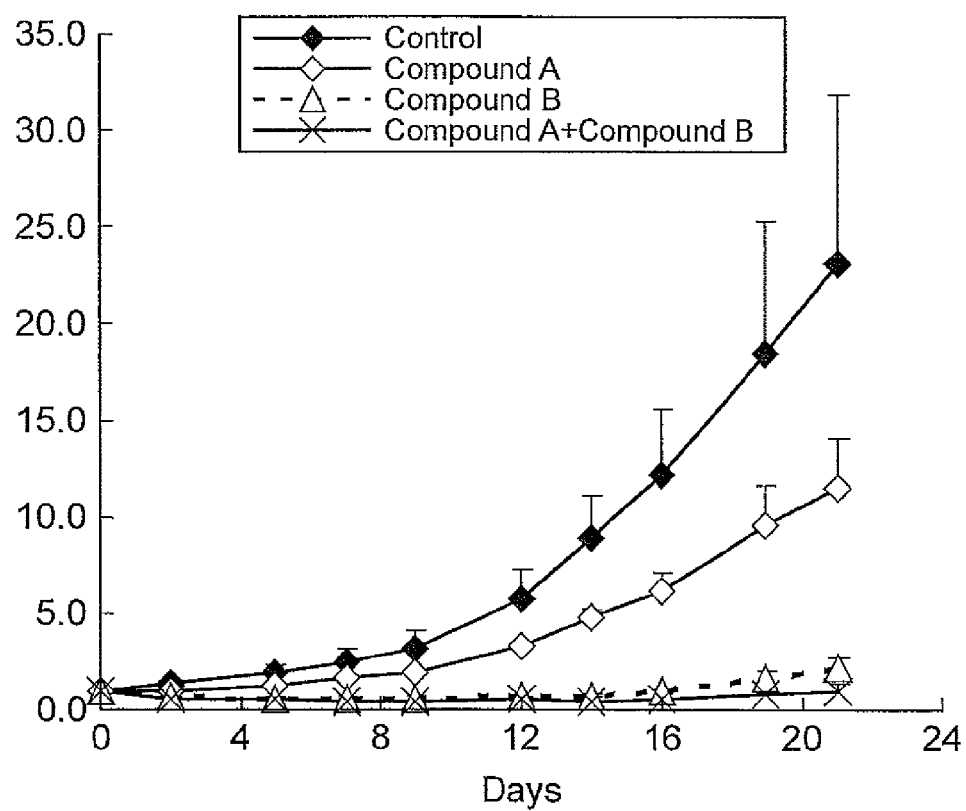
FIG. 5 is a graph showing a combined effect of Compound A and Compound B in a model animal to which human glioblastoma cell line (U87MG) was transplanted.

The results of RTV were summarized in Table 5 and FIG. 5. Compared to cases where Compound A and Compound B were each administered individually, the combined use of Compound A and Compound B exhibited a remarkably excellent antitumor effect. Also, although no statistical significance was shown by two-way ANOVA performed with respect to log-transformed RTV by setting Compound A and Compound B as the factors, an effect of complete inhibition of tumor proliferation was confirmed by the combined use of Compound A and Compound B.

TABLE 5

|  | Day 2 | Day 5 | Day 7 |
|---|---|---|---|
| Control group | 1.30 ± 0.19 | 1.86 ± 0.45 | 2.45 ± 0.71 |
| Compound A group | 0.95 ± 0.08 | 1.27 ± 0.07 | 1.59 ± 0.16 |
| Compound B group | 0.69 ± 0.05 | 0.61 ± 0.05 | 0.56 ± 0.10 |
| Combination group of Compound A and Compound B | 0.59 ± 0.05 | 0.49 ± 0.10 | 0.44 ± 0.09 |

|  | Day 9 | Day 12 | Day 14 |
|---|---|---|---|
| Control group | 3.19 ± 0.89 | 5.71 ± 1.58 | 8.88 ± 2.26 |
| Compound A group | 1.85 ± 0.13 | 3.29 ± 0.32 | 4.76 ± 0.49 |
| Compound B group | 0.57 ± 0.07 | 0.65 ± 0.08 | 0.73 ± 0.12 |
| Combination group of Compound A and Compound B | 0.36 ± 0.11 | 0.48 ± 0.16 | 0.46 ± 0.17 |

|  | Day 16 | Day 19 | Day 21 |
|---|---|---|---|
| Control group | 12.13 ± 3.46 | 18.47 ± 6.88 | 23.08 ± 8.72 |
| Compound A group | 6.19 ± 0.95 | 9.60 ± 1.99 | 11.53 ± 2.57 |
| Compound B group | 0.93 ± 0.13 | 1.65 ± 0.37 | 2.23 ± 0.51 |
| Combination group of Compound A and Compound B | 0.59 ± 0.20 | 0.78 ± 0.26 | 0.95 ± 0.38 |

The invention claimed is:

1. A method of treating a tumor, comprising administering to a patient in need thereof a combination of:

a compound represented by Formula (I) or a pharmaceutically acceptable salt thereof:

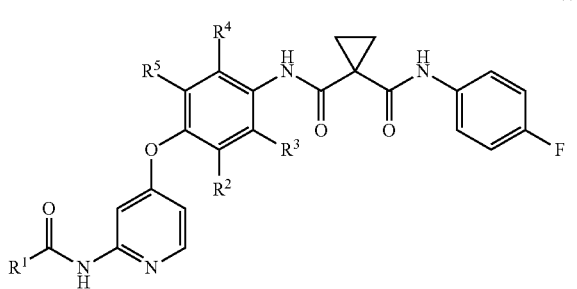

(I)

wherein $R^1$ is azetidinyl, piperidinyl, or a formula $-NR^{11a}R^{11b}$, each of which optionally have a substituent selected from Substituent group A, wherein $R^{11a}$ and $R^{11b}$ are the same or different and each is a hydrogen atom, $C_{1-6}$ alkyl, or piperidinyl optionally having $C_{1-6}$ alkyl, Substituent group A consists of hydroxyl, piperazinyl optionally having methyl, and azetidinyl optionally having dimethylamino, and $R^2$ to $R^5$ are the same or different and each is a hydrogen atom or a fluorine atom; and a compound represented by Formula (II) or a pharmaceutically acceptable salt thereof:

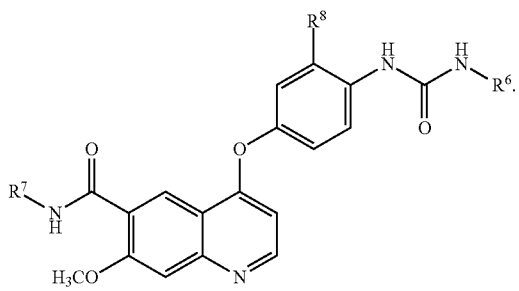

(II)

wherein R⁶ is $C_{1-6}$ alkyl or $C_{3-8}$ cycloalkyl,
R⁷ is a hydrogen atom, $C_{1-6}$ alkyl, or $C_{1-6}$ alkoxy, and
R⁸ is a hydrogen atom or a halogen atom.

2. The method of claim 1, wherein the compound represented by Formula (I) is selected from the group consisting of:

N-(2-fluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxamide:

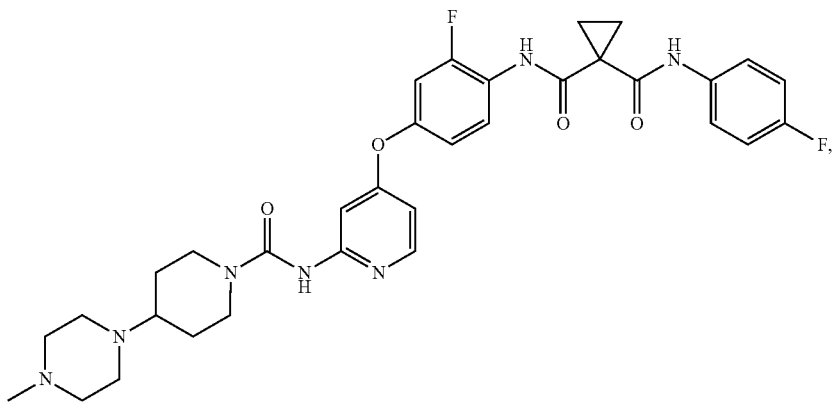 [SMILES: CN1CCN(C2CCN(C(=O)Nc3cc(Oc4ccc(NC(=O)C5(C(=O)Nc6ccc(F)cc6)CC5)c(F)c4)ccn3)CC2)CC1]

N-[4-({2-[({4-[3-(dimethylamino)azetidin-1-yl]piperidin-1-yl}carbonyl)amino]pyridin-4-yl}oxy)-2-fluorophenyl]-N'-(4-fluorophenyl)cyclopropane-1,1-dicarboxamide:

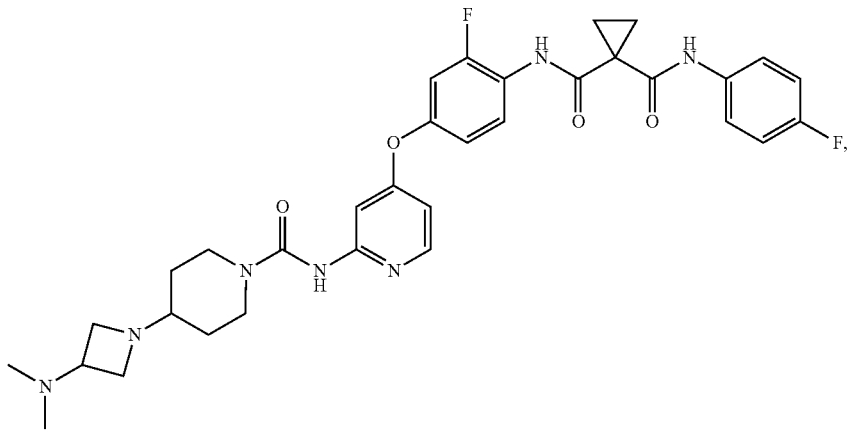 [SMILES: CN(C)C1CN(C2CCN(C(=O)Nc3cc(Oc4ccc(NC(=O)C5(C(=O)Nc6ccc(F)cc6)CC5)c(F)c4)ccn3)CC2)C1]

N-{2,5-difluoro-4-[(2-{[(3-hydroxyazetidin-1-yl)carbonyl]amino}pyridin-4-yl)oxy]phenyl}-N'-(4-fluorophenyl)cyclopropane-1,1-dicarboxamide:

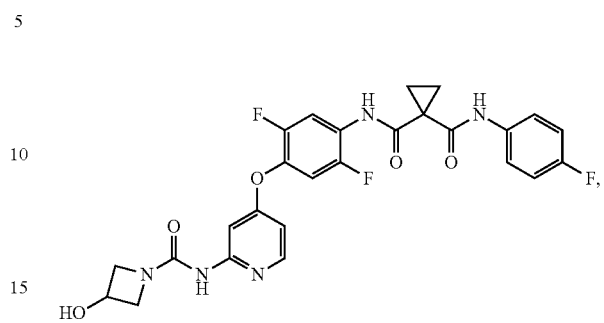

N-{2,5-difluoro-4-[(2-{[4-(4-methylpiperazin-1-yl)piperidin-1-yl]carbonyl}amino)pyridin-4-yl]oxy}phenyl)-N'-(4-fluorophenyl)cyclopropane-1,1-dicarboxamide:

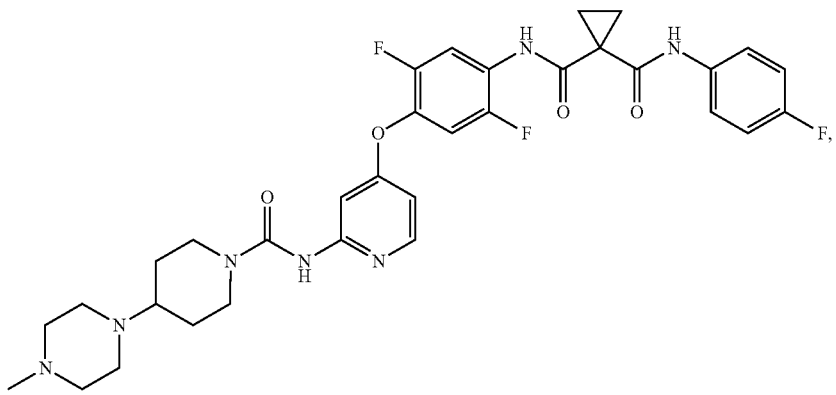 [SMILES: CN1CCN(C2CCN(C(=O)Nc3cc(Oc4cc(F)c(NC(=O)C5(C(=O)Nc6ccc(F)cc6)CC5)cc4F)ccn3)CC2)CC1]

and
N-(2,5-difluoro-4-{[2-({[methyl(1-methylpiperidin-4-yl)amino]carbonyl}amino)pyridin-4-yl]oxy}phenyl)-N'-(4-fluorophenyl)cyclopropane-1,1-dicarboxamide:

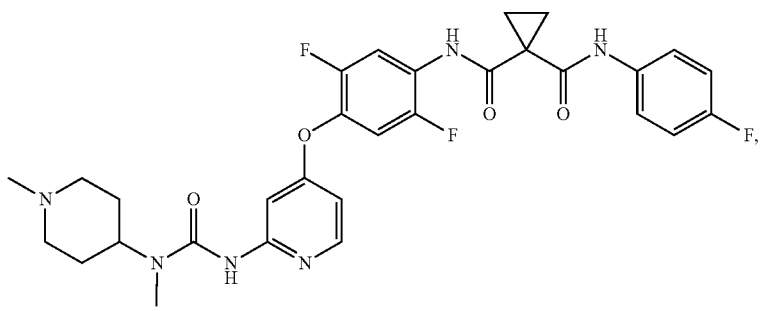 [SMILES: CN1CCC(N(C)C(=O)Nc2cc(Oc3cc(F)c(NC(=O)C4(C(=O)Nc5ccc(F)cc5)CC4)cc3F)ccn2)CC1]

and the compound represented by Formula (II) is selected from the group consisting of:
4-[3-chloro-4-(cyclopropylaminocarbonyl)aminophenoxy]-7-methoxy-6-quinolinecarboxamide:

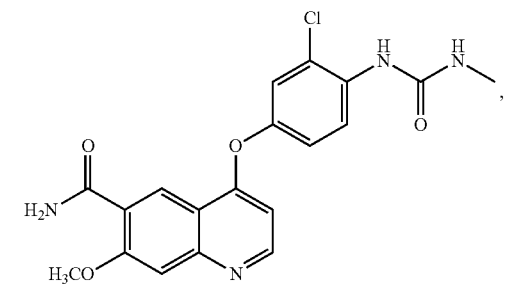 [SMILES: CNC(=O)Nc1ccc(Oc2ccnc3cc(OC)c(C(N)=O)cc23)cc1Cl]

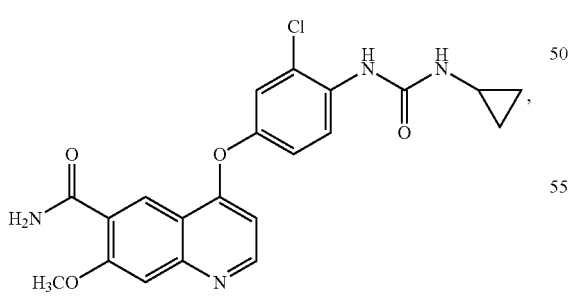

4-[3-chloro-4-(ethylaminocarbonyl)aminophenoxy]-7-methoxy-6-quinolinecarboxamide:

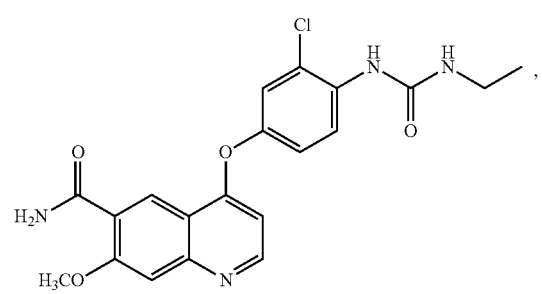 [SMILES: CCNC(=O)Nc1ccc(Oc2ccnc3cc(OC)c(C(N)=O)cc23)cc1Cl]

4-[3-chloro-4-(methylaminocarbonyl)aminophenoxy]-7-methoxy-6-quinolinecarboxamide:

N6-methoxy-4-(3-chloro-4-{[(cyclopropylamino)carbonyl]amino]phenoxy}-7-methoxy-6-quinolinecarboxamide:

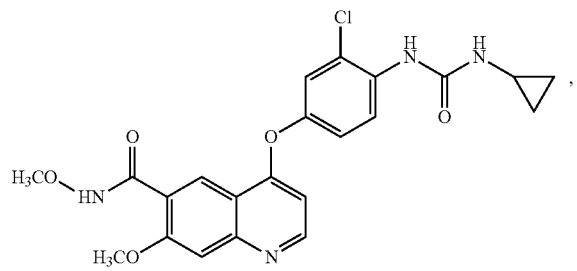 [SMILES: CONC(=O)c1cc2c(Oc3ccc(NC(=O)NC4CC4)c(Cl)c3)ccnc2cc1OC]

and
N6-methoxy-4-(3-chloro-4-{[(ethylamino)carbonyl]amino}phenoxy)-7-methoxy-6-quinolinecarboxamide:

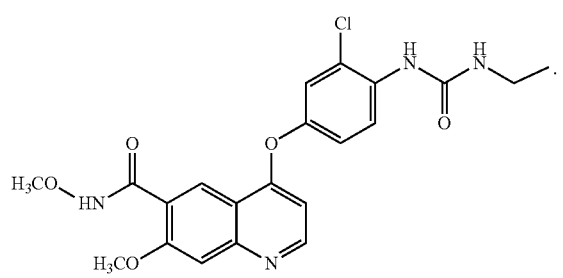 [SMILES: CCNC(=O)Nc1ccc(Oc2ccnc3cc(OC)c(C(=O)NOC)cc23)cc1Cl]

3. The method of claim 1, wherein the compound represented by Formula (I) is N-(2-fluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxamide:

and the compound represented by Formula (II) is 4-[3-chloro-4-(cyclopropylaminocarbonyl)aminophenoxy]-7-methoxy-6-quinolinecarboxamide:

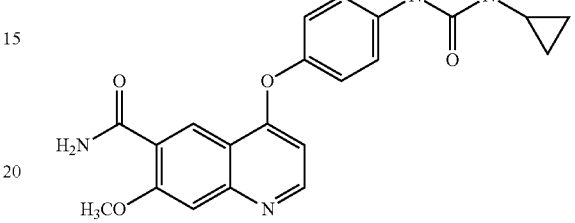

4. The method of claim 1, comprising simultaneous administration of the compound represented by Formula (I), or a pharmaceutically acceptable salt thereof, and the compound represented by Formula (II), or a pharmaceutically acceptable salt thereof.

5. The method of claim 1, comprising separate administration of the compound represented by Formula (I), or a pharmaceutically acceptable salt thereof, and the compound represented by Formula (II), or a pharmaceutically acceptable salt thereof.

6. The method of claim 1, wherein the tumor is melanoma, pancreatic cancer, gastric cancer, ovarian cancer, or glioblastoma.

7. A pharmaceutical composition comprising:
a compound represented by Formula (I) or a pharmaceutically acceptable salt thereof:

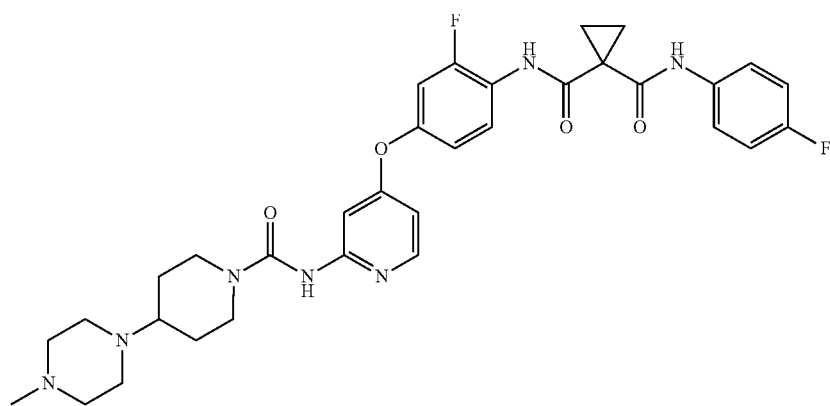

(I)

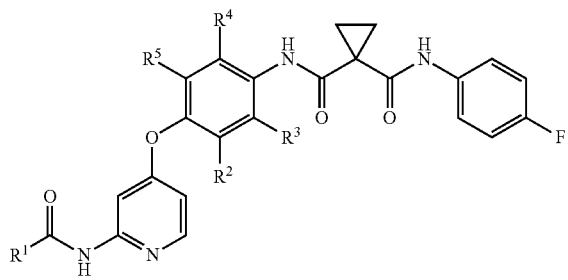

wherein R¹ is azetidinyl, piperidinyl, or a formula —NR$^{11a}$R$^{11b}$, each of which optionally have a substituent selected from Substituent group A, wherein R$^{11a}$ and R$^{11b}$ are the same or different and each is a hydrogen atom, C$_{1-6}$ alkyl, or piperidinyl optionally having C$_{1-6}$ alkyl, Substituent group A consists of hydroxyl, piperazinyl optionally having methyl, and azetidinyl optionally having dimethylamino, and R² to R⁵ are the same or different and each is a hydrogen atom or a fluorine atom; and a compound represented by Formula (II) or a pharmaceutically acceptable salt thereof:

(II)

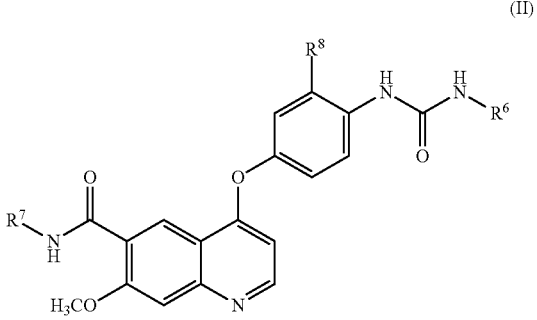

wherein R⁶ is C$_{1-6}$ alkyl or C$_{3-8}$ cycloalkyl,
R⁷ is a hydrogen atom, C$_{1-6}$ alkyl, or C$_{1-6}$ alkoxy, and
R⁸ is a hydrogen atom or a halogen atom.

8. The pharmaceutical composition of claim 7, wherein the compound represented by Formula (I) is selected from the group consisting of:

N-(2-fluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxamide:

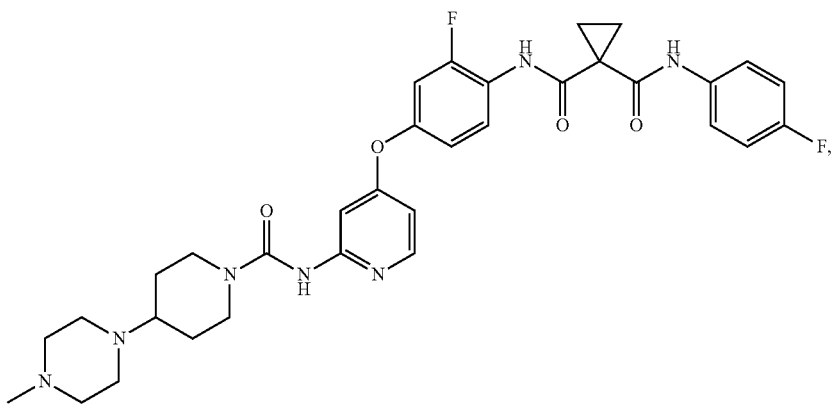 [SMILES: CN1CCN(C2CCN(C(=O)Nc3cc(Oc4ccc(NC(=O)C5(C(=O)Nc6ccc(F)cc6)CC5)c(F)c4)ccn3)CC2)CC1]

N-[4-({2-[({4-[3-(dimethylamino)azetidin-1-yl]piperidin-1-yl}carbonyl)amino]pyridin-4-yl}oxy)-2-fluorophenyl]-N'-(4-fluorophenyl)cyclopropane-1,1-dicarboxamide:

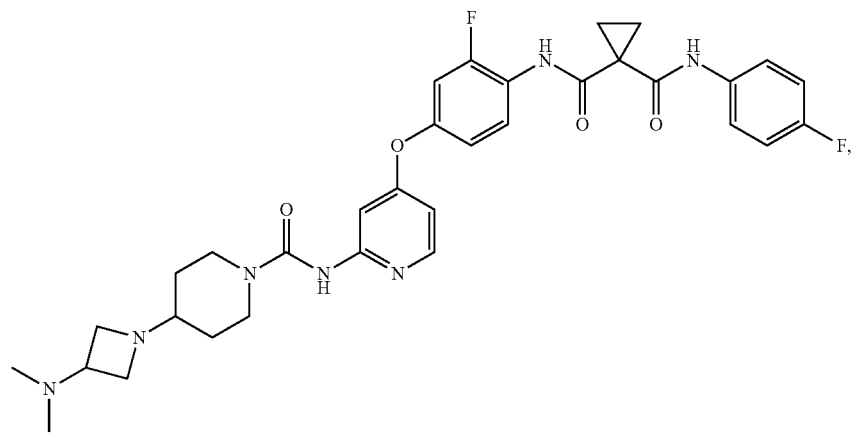 [SMILES: CN(C)C1CN(C2CCN(C(=O)Nc3cc(Oc4ccc(NC(=O)C5(C(=O)Nc6ccc(F)cc6)CC5)c(F)c4)ccn3)CC2)C1]

N-{2,5-difluoro-4-[(2-{[(3-hydroxyazetidin-1-yl)carbonyl]amino}pyridin-4-yl)oxy]phenyl}-N'-(4-fluorophenyl)cyclopropane-1,1-dicarboxamide:

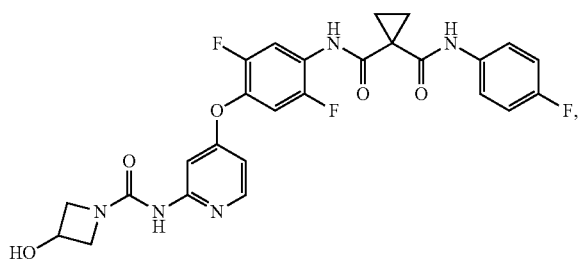 [SMILES: O=C(Nc1cc(Oc2cc(F)c(NC(=O)C3(C(=O)Nc4ccc(F)cc4)CC3)cc2F)ccn1)N1CC(O)C1]

N-{2,5-difluoro-4-[(2-{[4-(4-methylpiperazin-1-yl)piperidin-1-yl]carbonyl}amino)pyridin-4-yl]oxy}phenyl)-N'-(4-fluorophenyl)cyclopropane-1,1-dicarboxamide:

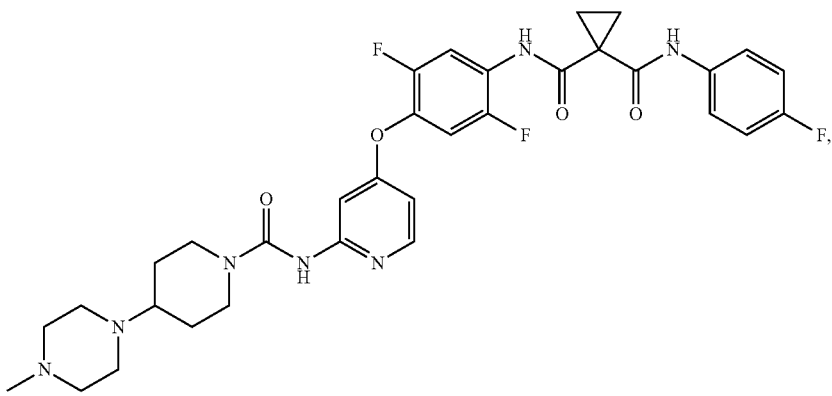 [SMILES: CN1CCN(C2CCN(C(=O)Nc3cc(Oc4cc(F)c(NC(=O)C5(C(=O)Nc6ccc(F)cc6)CC5)cc4F)ccn3)CC2)CC1]

and
N-(2,5-difluoro-4-{[2-({[methyl(1-methylpiperidin-4-yl)amino]carbonyl}amino)pyridin-4-yl]oxy}phenyl)-N'-(4-fluorophenyl)cyclopropane-1,1-dicarboxamide:

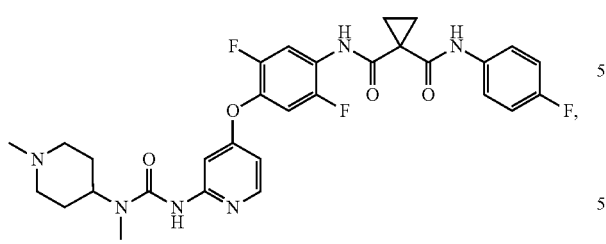

and the compound represented by Formula (II) is selected from the group consisting of:
4-[3-chloro-4-(cyclopropylaminocarbonyl)aminophenoxy]-7-methoxy-6-quinolinecarboxamide:

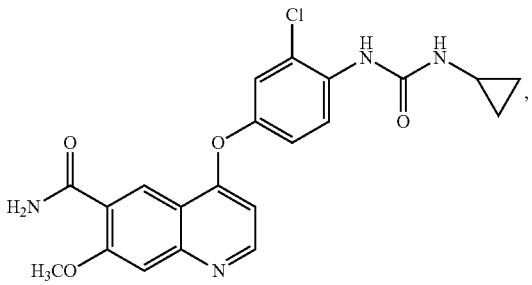 [SMILES: COc1cc2nccc(Oc3ccc(NC(=O)NC4CC4)c(Cl)c3)c2cc1C(N)=O]

4-[3-chloro-4-(methylaminocarbonyl)aminophenoxy]-7-methoxy-6-quinolinecarboxamide:

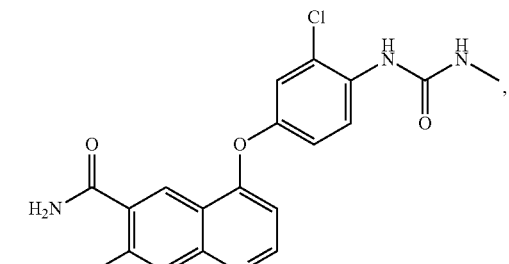

4-[3-chloro-4-(ethylaminocarbonyl)aminophenoxy]-7-methoxy-6-quinolinecarboxamide:

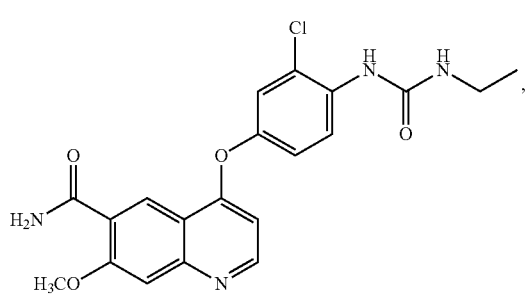 [SMILES: CCNC(=O)Nc1ccc(Oc2ccnc3cc(OC)c(C(N)=O)cc23)cc1Cl]

N6-methoxy-4-(3-chloro-4-{[(cyclopropylamino)carbonyl)amino]phenoxy}-7-methoxy-6-quinolinecarboxamide:

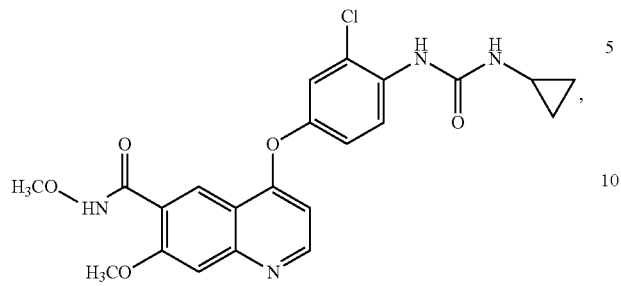

and
N6-methoxy-4-(3-chloro-4-{[(ethylamino)carbonyl]amino}phenoxy)-7-methoxy-6-quinolinecarboxamide:

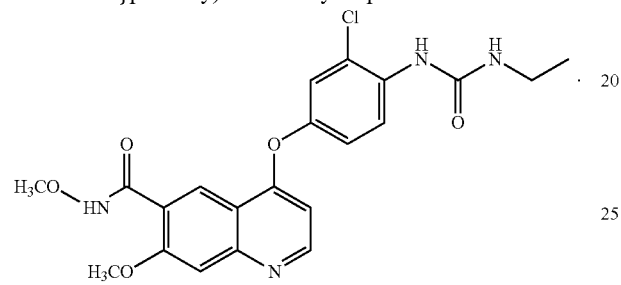

9. The pharmaceutical composition of claim 7, wherein the compound represented by Formula (I) is N-(2-fluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxamide:

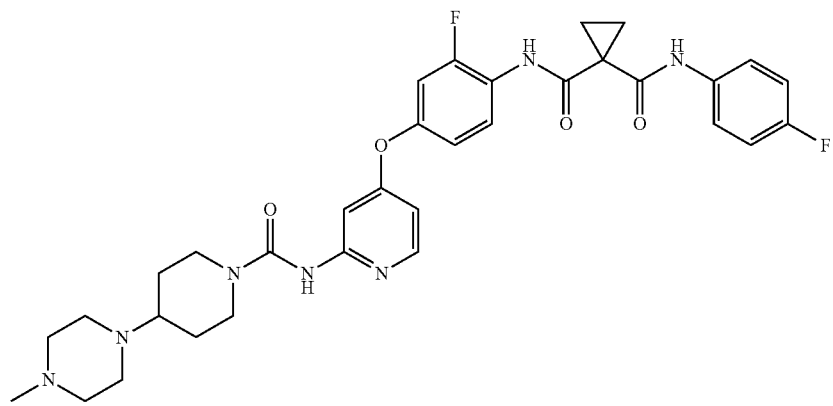 [SMILES: CN1CCN(C2CCN(C(=O)Nc3cc(Oc4ccc(NC(=O)C5(C(=O)Nc6ccc(F)cc6)CC5)c(F)c4)ccn3)CC2)CC1]

and the compound represented by Formula (II) is 4-[3-chloro-4-(cyclopropylaminocarbonyl)aminophenoxy]-7-methoxy-6-quinolinecarboxamide:

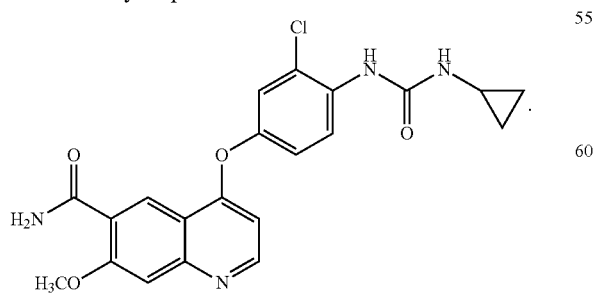

* * * * *

UNITED STATES PATENT AND TRADEMARK OFFICE
CERTIFICATE OF CORRECTION

PATENT NO.        : 9,012,458 B2                              Page 1 of 1
APPLICATION NO.   : 13/805826
DATED             : April 21, 2015
INVENTOR(S)       : Takayuki Nakagawa et al.

It is certified that error appears in the above-identified patent and that said Letters Patent is hereby corrected as shown below:

IN THE CLAIMS

Column 17, Claim 1

Lines 1-15, delete

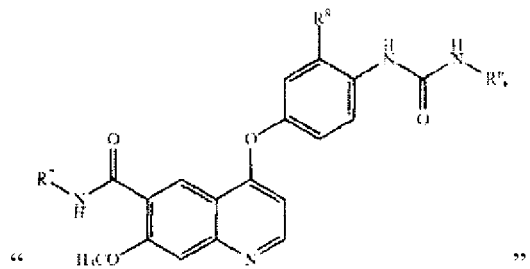

" "

and insert

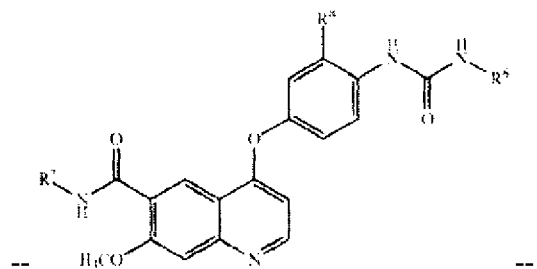

-- --

Signed and Sealed this
Fifteenth Day of December, 2015

Michelle K. Lee
*Director of the United States Patent and Trademark Office*